United States Patent [19]
Shimizu et al.

[11] Patent Number: 6,025,385
[45] Date of Patent: Feb. 15, 2000

[54] TAXANE DERIVATIVES AND DRUGS CONTAINING THE SAME

[75] Inventors: Hideaki Shimizu; Atsuhiro Abe; Takashi Yaegashi; Seigo Sawada; Hiroshi Nagata, all of Tokyo, Japan

[73] Assignee: Kabushiki Kaisha Yakult Honsha, Tokyo, Japan

[21] Appl. No.: 09/147,521

[22] PCT Filed: Jul. 14, 1997

[86] PCT No.: PCT/JP97/02431

§ 371 Date: Jan. 14, 1999

§ 102(e) Date: Jan. 14, 1999

[87] PCT Pub. No.: WO98/02426

PCT Pub. Date: Feb. 22, 1998

[30]     Foreign Application Priority Data

Jul. 15, 1996  [JP]  Japan ..................... 8-184741
Jul. 15, 1996  [JP]  Japan ..................... 8-184742

[51] Int. Cl.[7] ...................... C07D 305/14; A61K 31/335
[52] U.S. Cl. ..................... 514/449; 514/232.8; 514/253; 514/316; 514/320; 544/130; 544/369; 544/375; 544/510; 546/187; 546/196
[58] Field of Search ............................ 549/510; 546/187, 546/196; 544/369, 375, 130

[56]     References Cited

U.S. PATENT DOCUMENTS 5,880,131  3/1999  Greenwald ........................... 514/449

*Primary Examiner*—Robert Gerstl
*Attorney, Agent, or Firm*—Oblon, Spivak, McClelland, Maier & Neustadt, P.C.

[57]     ABSTRACT

This invention relates to a taxane derivative represented by the following formula (1):

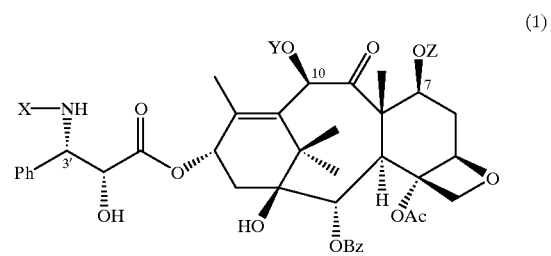

wherein at least one of X and Y represents a group —CO—A—B in which A represents a single bond, an alkylenecarbonyl group or the like and B represents a substituted or unsubstituted piperidino group or the like, the other represents a tert-butoxycarbonyl group or the like, and Z represents a hydrogen atom or a triethylenesilyl group, and also to a drug containing the same.

This compound has high solubility in water and also has excellent antitumor activities.

5 Claims, No Drawings

TAXANE DERIVATIVES AND DRUGS CONTAINING THE SAME

TECHNICAL FIELD

This invention relates to taxane derivatives or salts thereof having excellent solubility in water, and also to drugs containing the same.

BACKGROUND ART

Taxol (registered trademark) (i) represented by the following formula (i):

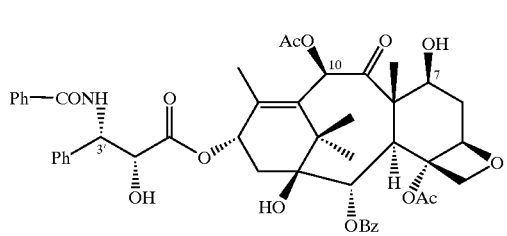

is a diterpenoid available by extraction from the bark of the Pacific yew tree, *Taxus brevifolia*, and was isolated and determined in structure for the first time by Wall, et al. (J. Am. Chem. Soc., 93, 2325, 1971). It has been reported to exhibit high efficacy against ovarian cancer and breast cancer (Ann. int. Med. 111, 273, 1989).

Formulation of Taxol into an injection however requires a special solvent, as it is a compound sparingly soluble in water. Taxol is therefore accompanied by problems in that the production of an injection is difficult and side effects may be induced by a solvent.

A great deal of work has therefore been conducted in recent years with a view to developing a water-soluble derivative of Taxol (Nicolaou, et al., Nature 364, 464, 1993). Under the current circumstances, however, no derivatives have been found yet to be equipped with satisfactory properties.

Accordingly, an object of the present invention is to provide a novel taxane derivative having improved water solubility and high antitumor activities.

DISCLOSURE OF THE INVENTION

With the foregoing circumstances in view, the present inventors have proceed with extensive research. As a result, it has been found that a compound represented by the below-described formula (1) and containing specific substituent(s) introduced at the 3'-position and/or 10-position of taxane (general name of the Taxol skeleton) has excellent antitumor activities, has water solubility extremely higher than Taxol and is hence useful as a drug, leading to the completion of the present invention.

The present invention therefore provides a taxane derivative represented by the following formula (1):

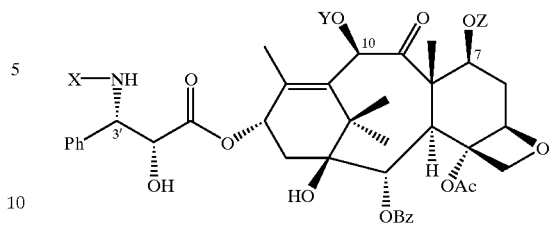

wherein at least one of X and Y represents a group —CO—A—B in which A represents a single bond, a group —R—CO—, a group —R—OCO— or a group —R—NHCO—, R representing a lower alkylene group or a phenylene group, B represents a group

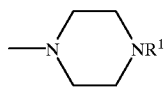

in which $R^1$ represents a hydrogen atom, a substituted or unsubstituted alkyl group or an aralkyloxycarbonyl group, of a group

in which $R^2$ represents an amino group, a mono or di-alkylamino group, a piperidino group, a pyrrolidino group or a morpholino group, or a group

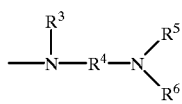

in which $R^3$ $R^5$ and $R^6$ each independently represent a hydrogen atom or a lower alkyl group and $R^4$ represents a lower alkylene group, and the other represents a hydrogen atom, a lower alkanoyl group, a benzoyl group, an alkoxycarbonyl group or a trihalogenoalkoxycarbonyl group; Z represents a hydrogen atom, a trialkylsilyl group or a trihalogenoalkoxycarbonyl group; Ac represents an acetyl group, Bz represents a benzoyl group, and Ph represents a phenyl group; or a salt thereof.

Further, the present invention also provides a drug comprising the taxane derivative represented by the formula (1) or the salt thereof as an active ingredient.

Still further, the present invention also provides a drug composition comprising the taxane derivative represented by the formula (1) or the salt thereof and a pharmaceutically acceptable carrier.

Moreover, the present invention also provides use of the taxane derivative represented by the formula (1) or the salt thereof as a drug.

In addition, the present invention also provides a method for the treatment of a tumor, which comprises administering taxane derivative represented by the formula (1) or the salt thereof.

BEST MODES FOR CARRYING OUT THE INVENTION

The taxane derivative according to the present invention is characterized in that as is represented by the formula (1), one or both of the 31-amino group and the 10-oxy group are a group —CO—A—B or groups —CO—A—B. In each —CO—A—B, the lower alkylene group represented by R in A may be a linear or branched alkylene group having 1–6 carbon atoms, examples of which can include methylene, ethylene, trimethylene, propylene and tetramethylene, with methylene, ethylene and trimethylene being particularly preferred. Particularly preferred examples of the group represented by A can include a single bond, —$C_2H_4$—CO—, —$C_2H_4$—NHCO—, $CH_2$—OCO— and —$C_2H_4$—OCO—.

The alkyl group represented by $R^1$ as a substituent on the piperazino group among the groups represented by B may be an alkyl group having 1–10 carbon atoms, examples of which can include methyl, ethyl, n-propyl, i-propyl, n-butyl, i-butyl, sec-butyl, tert-butyl, n-pentyl, n-hexyl, n-heptyl, n-nonyl and n-decyl. Of these alkyl groups, those having 1–6 carbon atoms, especially those having 1–3 carbon atoms are preferred. Illustrative of substituent or substituents of the alkyl group are monoalkylaminocarbonyl groups and dialkylaminocarbonyl groups. $C_{1-6}$ alkylaminocarbonyl groups can be mentioned as more preferred monoalkylaminocarbonyl groups, and di-$C_{1-6}$ alkylaminocarbonyl groups can be mentioned as more preferred dialkylaminocarbonyl groups. As the aralkyloxycarbonyl group, a phenyl-$C_{1-6}$ alkyloxycarbonyl group is preferred, with a benzyloxycarbonyl group being particularly preferred. As examples of the alkyl moiety of the alkylamino group represented by the substituent $R^2$ on the piperidino group, alkyl groups similar to those described above as examples of the alkyl group represented by $R^1$ can be mentioned, with methyl, ethyl, n-propyl and i-propyl being preferred. The lower alkyl groups as the substituents $R^3$, $R^5$ and $R^6$ in the group —N($R^3$)$R^4$—N($R^5$)$R^6$ may be alkyl groups having 1–6 carbon atoms, examples of which can include methyl, ethyl, n-propyl, i-propyl, n-butyl, i-butyl, sec-butyl and tert-butyl, with methyl being particularly preferred. Further, the lower alkylene group represented by $R^4$ may be a linear or branched alkylene group having 1–6 carbon atoms, examples of which can include methylene, ethylene, trimethylene, propylene and tetramethylene, with ethylene being particularly preferred. Particularly preferred examples of the group represented by B can include piperidinopiperidino, pyrrolidinopiperidino, morpholinopiperidino, dialkylaminopiperidino and N-alkylpiperazino.

It is particularly preferred that this group —CO—A—B is bonded as one of X and Y.

When only one of X and Y is the group —CO—A—B, the other is a hydrogen atom, a lower alkanoyl group, a benzoyl group, an alkoxycarbonyl group or a trihalogenoalkoxycarbonyl group. Here, the lower alkanoyl group may be an alkanoyl group having 2–6 carbon atoms, preferred examples of which can include acetyl and propionyl. The alkoxycarbonyl group may be a $C_{1-6}$ alkoxycarbonyl group, preferred examples of which can include methoxycarbonyl and tert-butoxycarbonyl. Further, the trihalogenoalkoxycarbony group may be a trihalogeno-$C_{1-6}$ alkoxycarbonyl group, preferred examples of which can include 2,2,2-trichloroethoxycarbonyl. Particularly preferred examples of groups represented by X and Y, other than —CO—A—B, can include, hydrogen atom, acetyl, 2,2,2-trichloroethoxycarbonyl, benzoyl and tert-butoxycarbonyl.

The group represented by Z is a hydrogen atom, a trialkylsilyl group, or a trihalogenoalkylcarbonyl group. Of these, a hydrogen atom, a tri($C_{1-6}$ alkyl)silyl group or trihalogeno($C_{1-6}$ alkoxy)carbonyl group is preferred, with hydrogen atom, triethylsilyl or 2,2,2-trichloroethoxycarbonyl being particularly preferred.

Illustrative of the salt of the taxane derivative (1) according to the present invention are pharmacologically acceptable salts, for example, anion salts such as acid salts, hydroiodide, tartrate, acetate, methanesulfonate, maleate, succinate, glutarate, and salts with amino acids such as arginine, lysine and alanine. Further, the taxane derivative or the salt thereof according to the present invention may exist in the form of a hydrate. The hydrate is also embraced in the present invention.

The taxane derivative (1) or the salt thereof according to the present invention can be prepared, for example, in accordance with the following reaction scheme (1) or reaction scheme (2).

<Reaction Scheme (1)>

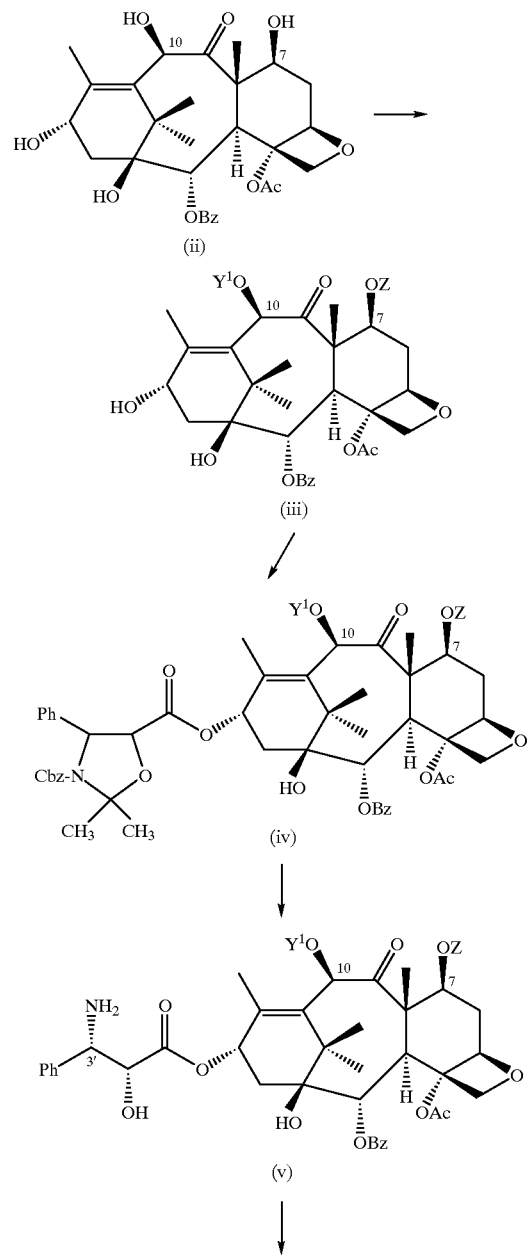

-continued

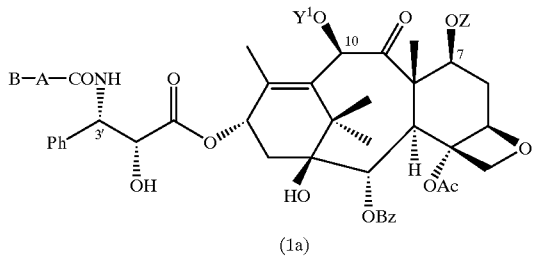

(1a)

wherein A, B, Z, Ac, Bz and Ph have the same meanings as defined above, $Y^1$ represents a hydrogen atom, a lower alkanoyl group, a benzoyl group, an alkoxycarbonyl group or a trihalogenoalkoxycarbonyl group, and Cbz represents a benzyloxycarbonyl group.

Described specifically, a taxane derivative (1a) according to the present invention is obtained by (ii) providing 10-deacetylbaccatin III, a known compound, as a raw material, (iii) protecting its 7- and 10-hydroxyl groups with suitable protecting groups, (iv) oxazolidinylating the 13-hydroxyl group, (v) subjecting the oxazolidinylated compound to ring opening, and then introducing a water-solubility-imparting B—A—CO group.

The protection of the 7- and 10-hydroxyl groups of 10-deacetylbaccatin III can be carried out by reacting an alkanoyl halide, trialkylsilyl halide, trichloroethoxycarbonyl halide or the like with 10-deacetylbaccatin III. The protecting groups may be selected as desired from conventionally-known protecting groups for a hydroxyl group, but triethylsilyl (TES), acetyl groups (Ac), trichloroethoxycarbonyl 1S groups or the like are preferred.

The 13-hydroxyl group is then oxazolidinylated to obtain the compound (iv). The oxazolidinylation may be conducted, for example, by reacting a derivative of oxazolidinecarboxylic acid, e.g., N-benzyloxycarbonyl(Cbz)-2,2-dimethyl-4-phenyl-oxazolidinecarboxylic acid, DCC, dimethylaminopyridine (DMAP) or the like with the compound (iii).

Next, concerning the ring opening of the oxazolidine ring, the object can be achieved by treating the oxazolidinylated compound (iv) with an acid in a solvent such as ethanol, deprotecting (TES), and then conducting catalytic reduction in the presence of palladium on charcoal.

The 3'-amino group of the resultant compound (v) is acylated by a suitable method, and the side chain (B—A—CO—) having a function to impart water solubility, which features the present invention, is then introduced, whereby the taxane derivative (1a) according to the present invention is successfully prepared.

Examples of the acylating method can include a method making use of an acid derivative in the presence of a suitable base and a method making use of a condensing agent.

Illustrative of an acylating reagent usable for the above acylation are acid chlorides, acid anhydrides and acid esters, and derivatives equivalent to these acylating reagents.

As a specific method for introducing the group (B—A—CO—), 4-dimethylaminopiperidinocarbonylation, for example, can be achieved by conducting treatment with 4-dimethylaminopiperidinocarbonyl chloride in the presence of a suitable base (for example, n-butyl-lithium) while using a solvent such as THF.

<Reaction Scheme (2)>

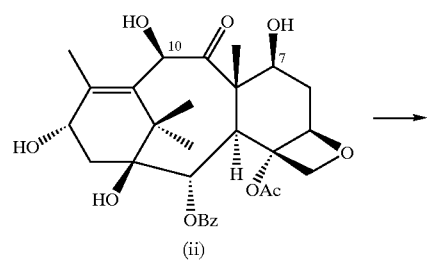

(ii)

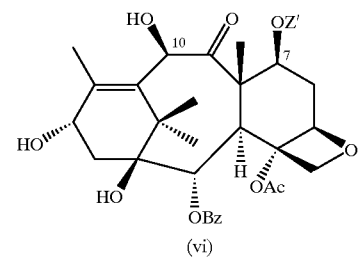

(vi)

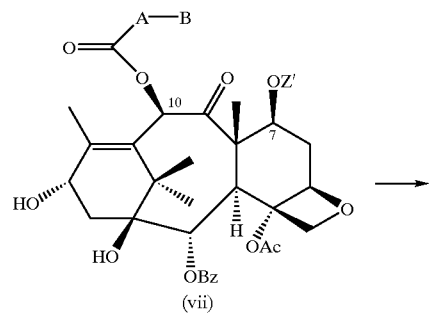

(vii)

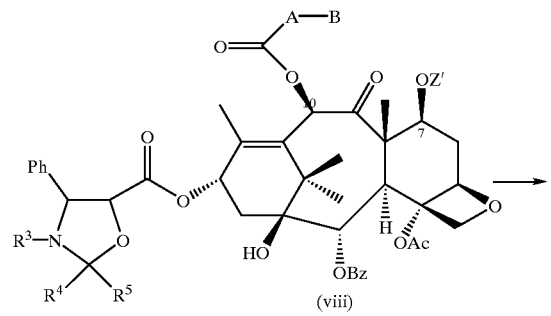

(viii)

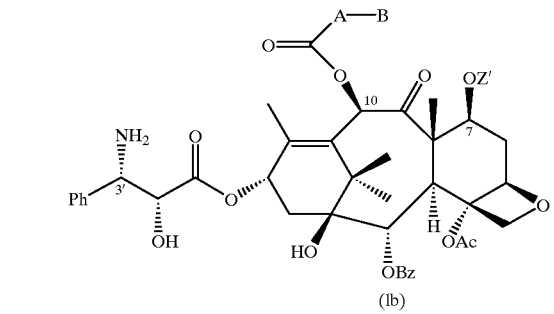

(1b)

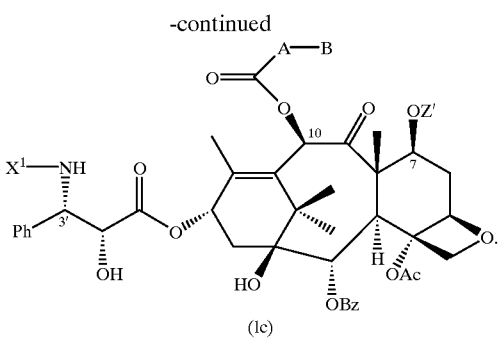

(1c)

wherein A, B, Ac, Bz and Ph have the same meanings as defined above, $X^1$ represents a group —CO—A—B, a lower alkanoyl group, a benzoyl group, an alkoxycarbonyl group and a trihalogenoalkoxycarbonyl group, $R^7$ represents a hydrogen atom, an alkoxycarbonyl group or an aralkyloxycarbonyl group, $R^8$ and $R^9$ each independently represent a hydrogen atom, an alkyl group, a halogenoalkyl group or an alkoxyphenyl group with the proviso that $R^8$ and $R^9$ do not represent hydrogen atoms at the same time and, when one of $R^8$ and $R^9$ is a halogenoalkyl group or an alkoxyphenyl group, the other is a hydrogen atom, and Z' represents a trialkylsilyl group (TES) or an alkoxycarbonyl group.

Described specifically, a target taxane derivative (1c) is obtained by (ii) providing lo-deacetylbaccatin III, a known compound, as a raw material, (vi) protecting its 7-hydroxyl group with a trialkylsilyl group or the like, (vii) acylating the resultant compound with a view to introducing a water-solubility-imparting B—A—CO— group into the 10-hydroxyl group, whereby the water-solubility-imparting B—A—CO— group is introduced, (viii) oxazolidinylating the 13-hydroxyl group, subjecting the oxazolidinylated compound to ring opening to obtain the compound (1b), and then introducing a water-solubility-imparting B—A—CO group or another acyl group.

The protection of the 7-hydroxyl group of 10-deacetylbaccatin III is carried by a method known in the art. Specifically, it can be achieved by conducting treatment with a trialkylsilyl chloride or alkoxycarbonyl chloride in pyridine. The protecting group may preferably be a trialkylsilyl group, with a tri($C_{1-6}$ alkyl)silyl group being more preferred and a triethylsilyl group being especially preferred.

The 10-hydroxyl group of the compound (vi) is then acylated, so that the side chain (B—A—CO—) having a function to impart water solubility is introduced.

As a method for conducting the acylation, the acylation may be carried out in a similar manner as in the above-described reaction scheme (1).

The 13-hydroxyl group is then oxazolidinylated to obtain the compound (vii). The oxazolidinylation may be conducted in a similar manner as in the above-described reaction scheme (1).

The compound (vii) so obtained is treated with an acid optionally in a solvent such as ethanol, whereby the compound (vii) is deprotected (de-TES or the like), and catalytic reduction is then conducted in the presence of palladium on charcoal to achieve ring opening of the oxazolidino ring, whereby the compound (1b) can be obtained.

The compound (1b) can be converted into the compound (1c) according to the present invention by substituting its amino group with B—A—COO—, alkoxycarbonylating the amino group or protecting the amino group with a benzoyl group. Here, the alkoxycarbonyl may be $C_{1-6}$ alkoxycarbonyl, with t-butoxycarbonyl being Si: particularly preferred. The t-butoxycarbonylation can be attained by conducting treatment, for example, with t-butoxycarbonyl-4,6-dimethyl-2-mercaptopyrimidine and triethylamine or the like. The benzoyl protection can be achieved by reacting benzoic anhydride or the like.

The compound—which is employed in the preparation steps of the compound (1) according to the present invention and is represented by the following formula (2):

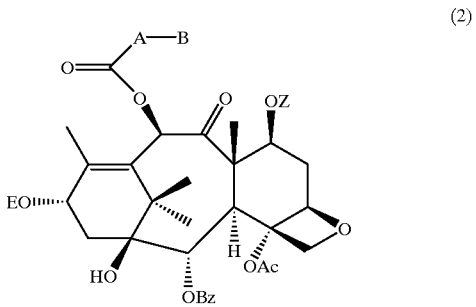

(2)

wherein A, B, Z, Ac and Bz have the same meanings as defined above and E represents a hydrogen atom or a group:

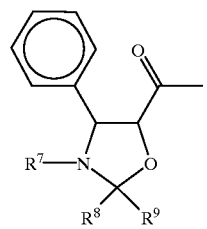

wherein $R^7$ represents a hydrogen atom, an alkoxycarbonyl group or an aralkyloxycarbonyl group, $R^8$ and $R^9$ each independently represent a hydrogen atom, an alkyl group, a halogenoalkyl group or an alkoxyphenyl group with the proviso that $R^8$ and $R^9$ do no represent hydrogen atoms at the same time and, when one of $R^8$ and $R^9$ is a halogenoalkyl group or an alkoxyphenyl group, the other is a hydrogen atom—is a novel compound and is a compound useful as a synthesis intermediate for the compound (1).

The alkyl groups represented by $R^8$ and $R^9$ may be an alkyl group having 1–10 carbon atoms, especially 1–6 carbon atoms, with methyl being more preferred. Further, the halogenoalkyl group may preferably be a halogeno($C_{1-6}$ alkyl) group, with trichloromethyl being particularly preferred. The alkoxyphenyl group may preferably be a $C_{1-6}$ alkoxyphenyl group, with a 4-$C_{1-6}$ alkoxyphenyl group being more preferred, and 4-methoxyphenyl being especially preferred.

The taxane derivative (1) according to the present invention was confirmed to have excellent antitumor activities in a test which was conducted by using, as an index, growth inhibition effects against a cell strain KB.

As the taxane derivative and the salt thereof according to the present invention have very high solubility in water (1,000-fold or higher compared with Taxol), they can be used as drugs such as injections without using any special solvent. As drug preparations, injections such as intravenous injections or intramuscular injections are preferred. In addition to such injections, they can also be formulated into liquid preparations such as inhalations, syrups or emulsions; solid preparations such as tablets, capsules or granules; or external preparations such ointments or suppositories.

These preparations may generally contain pharmacologically acceptable carriers, such as dissolution aids, stabilizers, humectants, emulsifiers, absorption enhancers and surfactants, as needed. Illustrative of these carriers are injection-grade distilled water, Ringer's injection, glucose, sucrose syrup, gelatin, edible oil, cacao butter, magnesium stearate, and talc.

The amount of the taxane derivative (1) contained in each of the above-described respective drug preparation varies depending on the conditions of a patient to whom the drug preparation is administered, its preparation form and the like. In general, however, its amount per unit dosage form may desirably range from about 0.5 to 100 mg in the case of injections, from about 5 to 1,000 mg in the case of oral preparations, from about 5 to 1,000 mg in the case of suppositories. Further, the daily dosage of the drug having the above-described dosage forms varies depending on the condition, body weight, age, sex and the like of each patient and cannot be determined in a wholesale manner. Nonetheless, the daily dosage may generally be about 0.1–50 mg/kg, preferably about 1–20 mg/kg per adult. It is preferred to administer this dosage as a single dose or in divided dosage forms, two to four times a day.

EXAMPLES

The present invention will next be described in further detail by Examples. It should however be borne in mind that the present invention is not limited to them.

Example 1

10-O-(4-Dimethylaminopiperidinocarbonyl)-7-O-triethylsilyl-10-deacetylbaccatin III (Compound 1)

1) Triphosgene (1.78 g, 6 mmol) was dissolved in benzene (120 ml), followed by the addition of a solution of 4-dimethylaminopiperidine (1.96 g, 15.3 mmol) in benzene and triethylamine (1.82 g, 18 mmol). The resulting mixture was stirred overnight at room temperature. Chloroform was added to the reaction mixture, and the resulting mixture was washed with water. The organic layer was dried over anhydrous magnesium sulfate, the solvent was distilled off under reduced pressure, and the residue was then purified by chromatography on a silica gel (chloroform-acetone mixed solvent [1:2]), whereby 4-dimethylaminopiperidinocarbonyl chloride (465 mg, 16%) was obtained.

$^1$H-NMR (CDCl$_3$)δ: 1.49(2H,m), 1.86(2H,d,J=10 Hz), 2.27(6H,s), 2.37(1H,m), 2.92(1H,t,J=11 Hz), 3.10(1H,t,J=13 Hz), 4.30(2H,d,J=13 Hz).

2) 7-O-Triethylsilyl-10-deacetylbaccatin III (135 mg, 0.20 mmol) was dissolved in THF. The resulting solution was stirred for 15 minutes over an acetone bath of −40° C. and a solution (0.24 mmol) of n-butyl-lithium in hexane was then added, followed by stirring for 30 minutes. A solution of 4-dimethylaminopiperidinocarbonyl chloride (127 mg, 0.67 mmol) in THF was to the thus-obtained solution, and the temperature was raised from −40° C. to room temperature, at which the contents were stirred overnight. A saturated aqueous solution of ammonium chloride was added to the reaction mixture. The resulting mixture was stirred, followed by the addition of chloroform. The mixture so obtained was washed with a saturated aqueous solution of sodium hydrogencarbonate. The organic layer was dried over anhydrous magnesium sulfate, the solvent was distilled off under reduced pressure, and the residue was purified by chromatography on a silica gel column (chloroform-methanol mixed solvent [9:1]), whereby the title compound (146 mg, 90%) was obtained.

$^1$H-NMR (CDCl$_3$)δ: 0.59(6H,m), 0.91(9H,t,J=8 Hz), 1.03 (3H,s), 1.14(3H,s), 1.60(3H,s), 2.20(3H,s), 2.27(3H,s), 1.41–2.30(8H,m), 2.38–3.05(9H,m), 3.87(1H,d,J=7 Hz,C3-H), 4.13(1H,d,J=8 Hz,C20-H), 4.29(1H,d,J=9 Hz,C20-H), 4.38(2H,br), 4.67(1H,dd,J=10,7 Hz,C7-H), 4.83(1H,br,C13-H), 4.94(1H,d,J=8 Hz,C5-H), 5.61(1H,d,J=7 Hz,C2-H), 6.38 (1H,s,C10-H), 7.46(2H,t,J=8 Hz), 7.59(1H,t,J=7 Hz), 8.09 (2H,d,J=7 Hz).

Example 2

13-O-(3-Benzyloxycarbonyl-2,2-dimethyl-4-phenyl-5-oxazolidinecarbonyl)-10-O-(4-dimethylaminopiperidinocarbonyl)-7-O-triethylsilyl-10-deacetylbaccatin III (Compound 2)

The compound (146 mg, 0.18 mmol) of Example 1 was dissolved in toluene, followed by the addition of 3-benzyloxycarbonyl-2,2-dimethyl-4-phenyl-5-oxazolidinecarboxylic acid (160 mg, 0.45 mmol), DCC (93 mg, 0.45 mmol) and DMAP (2 mg). The resulting mixture was stirred at room temperature for 20 hours. The reaction mixture was filtered. After the filtrate was concentrated, chloroform was added to the residue. The thus-obtained mixture was washed with a saturated aqueous solution of sodium hydrogencarbonate. The organic layer was dried over anhydrous magnesium sulfate, the solvent was distilled off under reduced pressure, and the residue was purified by chromatography on a silica gel column (chloroform-methanol mixed solvent [19:1]), whereby the title compound (207 mg, 100%) was obtained.

$^1$H-NMR (CDCl$_3$)δ: 0.56(6H,m), 0.90(9H,t,J=8 Hz), 1.17 (6H,s), 1.65(3H,s), 1.74(3H,s), 1.80(3H,s), 1.89(3H,s), 2.07 (3H,s), 1.32–2.20(8H,m), 2.27–3.05(8H,m), 3.77(1H,d,J=7 Hz,C3-H), 4.08(1H,d,J=8 Hz,C20-H), 4.23(1H,d,J=9 Hz,C20-H), 4.30(2H,br), 4.43(1H,dd,J=10,7 Hz,C7-H), 4.49 (1H,d,J=6 Hz), 4.86(1H,d,J=8 Hz,C5-H), 4.81–5.18(2H,m), 5.21(1H,s), 5.63(1H,d,J=8 Hz,C2-H), 6.21(1H,br,C13-H), 6.36(1H,s,C10-H), 6.73(1H,br), 7.22–7.40(9H,m), 7.47(2H, t,J=7 Hz), 7.59(1H,t,J=7 Hz), 8.02(2H,d,J=7 Hz).

Example 3

13-O-[3-(tert-Butoxycarbonylamino)-2-hydroxy-3-phenylpropionyl]-10-O-(4-dimethylaminopiperidinocarbonyl)-10-deacetylbaccatin III (Compound 3)

The compound (106 mg, 0.092 mmol) of the compound of Example 2 was dissolved in ethanol (5 ml), followed by the addition of 0.1 N hydrochloric acid (10 ml). The resulting mixture was stirred at room temperature for 17 hours. The solvent was distilled off under reduced pressure, and chloroform was added to the residue. The thus-obtained mixture was washed with a saturated aqueous solution of sodium hydrogencarbonate. The organic layer was dried over anhydrous magnesium sulfate, and the solvent was distilled off under reduced pressure. Methanol (10 ml), water (1 ml) and 10% palladium-charcoal (50 mg) were added to the residue, followed by stirring for 2 hours at room temperature and atmospheric pressure under a hydrogen gas atmosphere. The reaction mixture was filtered through a glass filter with Celite distributed thereon. After the filtrate was concentrated, methylene chloride (10 ml) was added to the residue so that the residue was dissolved. To the solution so obtained, S-tert-butoxycarbonyl-4,6-dimethyl-2-mercaptopyrimidine (24 mg, 0.10 mmol) and triethylamine (10 mg, 0.10 mmol) were added. The resulting mixture was stirred at room temperature for 3 days and further at 40° C. for 2 days.

Chloroform was added to the reaction mixture, and the resulting mixture was washed with a saturated aqueous solution of sodium hydrogencarbonate. The organic layer was dried over anhydrous magnesium sulfate, the solvent was distilled off under reduced pressure, and the residue was preliminarily purified by chromatography on a silica gel column (chloroform-methanol mixed solvent [9:1]). Further purification was conducted by reverse-phase high-performance column chromatography (eluent: 10 mM potassium dihydrogen-phosphate-acetonitrile [1:1]), whereby the title compound (43 mg, 49%) was obtained.

$^1$H-NMR (CDCl$_3$)δ: 1.05(3H,s), 1.20(3H,s), 1.27(9H,s), 1.64(3H,s), 1.80(3H,s), 2.36(3H,s), 1.23–2.50(8H,m), 2.74 (6H,s), 2.89(1H,br), 3.12–3.43(2H,m), 3.38(1H,s), 3.71(1H, d,J=7 Hz,C3-H), 4.10(1H,d,J=8 Hz,C20-H), 4.24(1H,d,J=8 Hz,C20-H), 4.22–4.43(3H,m), 4.56(1H,s,C2'-H), 4.89(1H, d,J=10 Hz,C5-H), 5.23(1H,br), 5.28(1H,d,J=10 Hz,C3'-H), 5.59(1H,d,J=7 Hz,C2-H), 6.18(1H,br,C13-H), 6.20(1H,s, C10-H), 7.31(5H,m), 7.43(2H,t,J=8 Hz), 7.55(1H,t,J=7 Hz), 8.04(2H,d,J=7 Hz). SI-MS m/z: 962 [M+H]$^+$

Example 4

10-O-(4-Dipropylaminopiperidinocarbonyl)-7-O-triethylsilyl-10-deacetylbaccatin III (Compound 4)

7-O-Triethylsilyl-10-deacetylbaccatin III (100 mg, 0.15 mmol) was dissolved in tetrahydrofuran (5 ml), followed by the addition of a 1.6 M solution of n-butyllithium in hexane (0.13 ml, 0.195 mmol) at –40° C. under an argon gas atmosphere. The resulting mixture was stirred for 1 hour. Further, a solution of 4-dipropylaminopiperidinocarbonyl chloride (28 mg, 0.17 mmol) in tetrahydrofuran (1 ml) was added. The thus-obtained mixture was stirred at –20° C. The temperature of the mixture was then raised gradually to room temperature, at which the mixture was stirred overnight. An aqueous solution of ammonium chloride (50 ml) was then added to the reaction mixture, and the resulting mixture was extracted with ethyl acetate. The organic layer was washed with a saturated aqueous solution of sodium chloride, dried over anhydrous sodium sulfate, and then concentrated to dryness under reduced pressure. The residue was purified by chromatography on a silica gel column (chloroform-methanol [96:4]). Eluted TLC single-spot fractions were combined together and then concentrated to dryness under reduced pressure, whereby the title compound (63 mg, 50%) was obtained as colorless crystals.

$^1$H-NMR (CDCl$_3$)δ: 0.56–0.64(6H,m,Si—CH$_2$X3), 0.87–0.95(15H,m,-MeX3 and propyl-MeX2), 1.05(3H,s,C-16 or C17-Me), 1.18(3H,s,C16 or C-17-Me), 1.44(3H,br-s), 1.60(3H,br-s), 1.68(3H,s,C19-Me), 1.75–1.89(2H,m), 1.84–1.90(1H,m,C6-H), 2.25(3H,s,C18-Me), 2.25–2.30(2H, m,C14-H), 2.28(3H,s,C4-OAc), 2.41(2H,s), 2.52(3H,m), 2.61–2.87(3H,m), 3.90(1H,d,J=7 Hz,C3-H), 4.15(1H,d,J=8 Hz,C20-H), 4.27(1H,br-s), 4.30(1H,d,J=9 Hz,C20-H), 4.47 (1H,br-s), 4.49(1H,dd,J=7,11 Hz,C7-H), 4.84(1H,m,C13-H), 4.96(1H,d,J=8 Hz,C5-H), 5.64(1H,d,J=7 Hz,C2-H), 6.39 (1H,s,C10-H), 7.46–7.49(2H,m,ArH), 7.58–7.62(1H,m, ArH), 8.11(2H,d,J=7 Hz,ArH). SI-MS m/z: 869 [M+H]$^+$ Example 5

10-O-(Dipropylaminopiperidinocarbonyl)-13-O-(4-phenyl-2-trichloromethyl-5-oxazolidinecarbonyl)-7-O-triethylsilyl-10-deacetylbaccatin III (Compound 5)

The compound (22 mg, 0.025 mmol) of Example 4 and 4-phenyl-2-trichloromethyl-5-oxazolidinecarboxylic acid (31 mg, 0.1 mmol) were dissolved in toluene (5 ml), followed by the addition of DCC (23 mg, 0.11 mmol) and dimethylaminopyridine (1 mg). The resulting mixture was stirred at room temperature for 2 hours under an argon gas atmosphere. A precipitate in the reaction mixture was filtered off, and a saturated aqueous solution of sodium hydrogencarbonate was added to the filtrate. The thus-obtained mixture was extracted with ethyl acetate. The organic layer was washed with a saturated aqueous solution of sodium chloride, dried over anhydrous sodium sulfate, and then concentrated to dryness under reduced pressure. The residue was purified by chromatography on a silica gel column (chloroform-methanol mixed solvent (95:5)). Eluted TLC single-spot fractions were combined together and then concentrated to dryness under reduced pressure, whereby the title compound (20 mg, 70%) was obtained as colorless crystals.

$^1$H-NMR (CDCl$_3$)δ: 0.57–0.61(6H,m,Si—CH$_2$X3), 0.85–0.92(15H,m,-MeX3 and propyl-MeX2), 1.21(6H,s, C16-Me and C17-Me), 1.37–1.87(9H,m), 1.65(3H,s,C19-Me), 1.78(3H,s,C18-Me), 2.11(3H,s,C4-OAc), 2.11–2.14 (2H,m,C14-H), 2.38–3.00(8H,m), 3.27(1H,t,J=6 Hz,-NH—), 3.77(1H,d,J=7 Hz,C3-H), 4.09(1H,d,J=8 Hz,C20-H), 4.23(1H,d,J=8 Hz,C20-H), 4.26(1H,br-s), 4.42(1H,br-s), 4.45(1H,dd,J=7 Hz,10 Hz,C7-H), 4.67–4.69(1H,m), 4.74–4.78(1H,m), 4.87(1H,d,J=8 Hz,C5-H), 5.52(1H,d,J=6 Hz), 5.65(1H,d,J=7 Hz,C2-H), 6.29(1H,t,J=8 Hz,C13-H), 6.37(1H,s,C10-H), 7.37–7.41(3H,m,ArH), 7.49–7.57(4H,m, ArH), 7.63–7.67(1H,m,ArH), 8.03–8.05(2H,m,ArH).

Example 6

13-O-[3-(tert-Butoxycarbonylamino)-2-hydroxy-3-phenylpropionyl]-10-O-(4-dipropylaminopiperidinocarbonyl)-10-deacetylbaccatin III (Compound 6)

The compound (22 mg, 0.019 mmol) of Example 5 was dissolved in methanol (4 ml), followed by the addition of methanesulfonic acid (20 mg, 0.20 mmol). The resulting mixture was stirred overnight at room temperature under an argon gas atmosphere. A saturated aqueous solution of sodium hydrogencarbonate was added to the reaction mixture, followed by extraction with ethyl acetate. The organic layer was washed with a saturated aqueous solution of sodium chloride, dried over anhydrous sodium sulfate, and then concentrated to dryness under reduced pressure, whereby a colorless oil was obtained.

The oil was then dissolved in tetrahydrofuran (20 ml), followed by the addition of di-tert-butyl dicarbonate (5.3 mg, 0.024 mmol) and sodium hydrogen-carbonate (2 mg). The thus-obtained mixture was stirred at room temperature for 60 hours under an argon gas atmosphere. Water was added to the reaction mixture, and the resulting mixture was extracted with ethyl acetate. The organic layer was washed with a saturated aqueous solution of sodium chloride, dried over anhydrous sodium carbonate, and then concentrated to dryness under reduced pressure. The residue was purified by chromatography on a silica gel column (chloroform-methanol mixed solvent [94:6]). Eluted TLC single-spot fractions were combined together and then concentrated to dryness under reduced pressure, whereby a colorless oil (11 mg) was obtained. The oil was purified further by reverse-phase high-performance liquid column chromatography (eluent: 10 mM potassium dihydrogenphosphate-acetonitrile mixed solvent [1:1]).

Eluted HPLC single-peak fractions were combined together and then concentrated under reduced pressure. The concentrate was extracted with chloroform. The organic layer was washed with a saturated aqueous solution of sodium chloride, dried over anhydrous sodium sulfate, and then concentrated to dryness under reduced pressure, whereby the title compound (3 mg, 16%) was obtained as colorless crystals.

$^1$H-NMR (CDCl$_3$)δ: 0.97(6H,m), 1.14(3H,s), 1.27(3H,s), 1.33(9H,s,t-Bu), 1.41–2.18(8H,m), 1.66(3H,s), 1.86(3H,s), 1.86–1.92(1H,m), 2.29(2H,m,C14-H), 2.38(3H,s,C4-OAc), 2.53(1H,m,C6-H), 2.55–3.60(7H,m), 3.79(1H,d,J=7 Hz,C3-H), 4.17(1H,d,J=9 Hz,C20-H), 4.21–4.31(2H,m), 4.30(1H,d,J=9 Hz,C20-H), 4.44(1H,s,C7-H), 4.63(1H,s,C2'-H), 4.96 (1H,d,J=9 Hz,C5-H), 5.27(1H,m), 5.38(1H,d,J=10 Hz,C3'-H), 5.66(1H,d,J=7 Hz,C2-H), 6.25(1H,s,C13-H), 6.26(1H,s,C10-H), 7.31–7.42(5H,m,ArH), 7.48–7.52(2H,m,ArH), 7.60–7.63(1H,m,ArH), 8.10–8.12(2H,m,ArH). SI-MS m/z: 1018 [M+H]$^+$

Example 7

10-O-(4-Piperidinopiperidinocarbonyl)-7-O-triethylsilyl-10-deacetylbaccatin III (Compound 7)

Using 7-O-triethylsilyl-10-deacetylbaccatin III (100 mg, 0.15 mmol) and 4-piperidinopiperidinocarbonyl chloride (45 mg, 0.19 mmol), reactions and post-treatment were conducted as in Example 4, whereby the title compound (90 mg, 70%) was obtained as colorless crystals.

$^1$H-NMR (CDCl$_3$)δ: 0.56–0.62(6H,m,Si—CH$_2$X3), 0.92 (9H,t,J=8 Hz,-MeX3), 1.03(3H,s,C16 or C17-Me), 1.17(3H,s,C16 or C17-Me), 1.44(3H,m), 1.60(3H,m), 1.68(3H,s,C19-Me), 1.80–1.89(4H,m), 2.19–2.34(2H,m,C14-H), 2.23 (3H,s,C18-Me), 2.27(3H,s,C4-OAc), 2.52(6H,m), 2.79(3H,m), 3.89(1H,d,J=7 Hz,C3-H), 4.10–4.50(2H,br-s), 4.14(1H,d,J=8 Hz,C20-H), 4.29(1H,d,J=8 Hz,C20-H), 4.49(1H,dd,J=7,11 Hz,C7-H), 4.80(1H,m,C13-H), 4.96(1H,d,J=8 Hz,C5-H), 5.62(1H,d,J=7 Hz,C2-H), 6.38(1H,s,C10-H), 7.45–7.49 (2H,m,ArH), 7.57–7.61(1H,m,ArH), 8.10(2H,d,J=7 Hz,ArH). SI-MS m/z: 853 [M+H]$^+$

Example 8

13-O-(4-Phenyl-2-trichloromethyl-5-oxazolidinecarbonyl)-10-O-(4-piperidinopiperidinocarbonyl)-7-O-triethylsilyl-10-deacetylbaccatin III (Compound 8)

Using the compound (21 mg, 0.025 mmol) of Example 7, reactions and post-treatment were conducted as in Example 5, whereby the title compound (22 mg, 78%) was obtained as colorless crystals.

$^1$H-NMR (CDCl$_3$)δ: 0.57–0.61(6H,m,Si—CH$_2$X3), 0.92 (9H,t,J=8 Hz,-MeX3), 1.21(6H,s,C16-Me and C17-Me), 1.42–1.51(3H,m), 1.62–1.71(3H,m), 1.65(3H,s,C19-Me), 1.78(3H,s,C18-Me), 1.77–1.90(4H,m), 2.10(3H,s,C4-OAc), 2.11–2.16(2H,m,C14-H), 2.48(1H,m,C6-H), 2.48–2.98(8H,m), 3.28(1H,t,J=6 Hz,-NH—), 3.77(1H,d,J=7 Hz,C3-H), 4.09(1H,d,J=8 Hz,C20-H), 4.23(1H,d,J=8 Hz,C20-H), 4.25 (2H,br-s), 4.44(1H,dd,J=7 Hz,11 Hz,C7-H), 4.65–4.69(1H,m), 4.74–4.78(1H,m), 4.86(1H,d,J=8 Hz,C5-H), 5.52(1H,d,J=6 Hz), 5.65(1H,d,J=7 Hz,C2-H), 6.28(1H,t,J=8 Hz,C13-H), 6.37(1H,s,C10-H), 7.38–7.42(3H,m,ArH), 7.49–7.57 (4H,m,ArH), 7.63–7.67(1H,m,ArH), 8.04(2H,d,J=7 Hz,ArH).

Example 9

13-O-[3-(tert-Butoxycarbonylamino)-2-hydroxy-3-phenylpropionyl]-10-O-(4-piperidinopiperidinocarbonyl)-10-deacetylbaccatin III (Compound 9) Using the compound (22 mg, 0.019 mmol) of Example 8, reactions and post-treatment were conducted as in Example 6, whereby the title compound (3 mg, 17%) was obtained as a colorless oil.

$^1$H-NMR (CDCl$_3$)δ: 1.14 (3H,s, C16 or C17-Me), 1.27 (3H,s,C16 or C17-Me), 1.33(9H,s,t-Bu), 1.41–2.20(9H,m), 1.67(3H,s,C19-Me), 1.81(4H,m,C18-Me and C6-H), 2.25–2.42(2H,m,C14-H), 2.37(3H,s,C4-OAc), 2.40–3.10 (8H,m), 2.50–2.57(1H,m,C6-H), 3.16(1H,s), 3.79(1H,d,J=7 Hz,C3-H), 4.17(1H,d,J=8 Hz,C20-H), 4.17–4.28(2H,m), 4.30(1H,d,J=8 Hz,C20-H), 4.44(1H,dd,J=7,11 Hz,C7-H), 4.63(1H,d,J=3 Hz,C2'-H), 4.96(1H,d,J=8 Hz,C5-H), 5.28 (1H,m), 5.36(1H,d,J=10 Hz,C3'-H), 5.66(1H,d,J=7 Hz,C2-H), 6.25(2H,m,C10-H and C13-H), 7.29–7.44(5H,mu,ArH), 7.47–7.55(2H,m,ArH), 7.59–7.64(1H,m,ArH), 8.08–8.13 (2H,m,ArH). SI-MS m/z: 1002 [M+H]$^+$

Example 10

10-O-(4-Pyrrolidinopiperidinocarbonyl)-7-O-triethylsilyl-10-deacetylbaccatin III (Compound 10)

1) Triphosgene (742 mg, 2.5 mmol) was dissolved in benzene (60 ml), followed by the addition of a solution of 4-pyrrolidinopiperidine (1.00 g, 6.5 mmol) in benzene and triethylamine (7.5 mmol). The resulting mixture was stirred at room temperature for 17 hours. Chloroform was added to the reaction mixture, and the thus-obtained mixture was washed with water. The organic layer was dried over anhydrous magnesium sulfate, and the solvent was distilled off under reduced pressure. The residue was purified by chromatography on a silica gel column (chloroform-acetone mixed solvent [1:2]), whereby 4-pyrrolidinopiperidinocarbonyl chloride (158 mg, 11%) was obtained.

$^1$H-NMR (CDCl$_3$)δ: 1.50–2.15(10H,m), 2.30–2.90(5H,m), 3.02(1H,t,J=11 Hz), 3.18(1H,t,J=12 Hz), 4.25(2H,d,J=12 Hz).

2) Using 4-pyrrolidinopiperidinocarbonyl chloride (95 mg, 0.44 mmol), reactions and post-treatment were conducted as in Example 1, whereby the title compound (169 mg, 100%) was obtained.

$^1$H-NMR (CDCl$_3$)δ: 0.57(6H,m), 0.90(9H,t,J=8 Hz), 1.04 (3H,s), 1.13(3H,s), 1.65(3H,s), 2.20(3H,s), 2.27(3H,s), 1.50–2.37(13H,m), 2.51(1H,m), 2.70–3.12(4H,m), 3.87(1H,d,J=7 Hz,C3-H), 4.13(1H,d,J=8 Hz,C20-H), 4.29(1H,d,J=8 Hz,C20-H), 4.40(2H,br), 4.47(1H,dd,J=10,7 Hz,C7-H), 4.85 (1H,br,C13-H), 4.94(1H,d,J=8 Hz,C5-H), 5.61(1H,d,J=7 Hz,C2-H), 6.38(1H,s,C10-H), 7.46(2H,t,J=8 Hz), 7.59(1H,t,J=7 Hz), 8.09(2H,d,J=7 Hz).

Example 11

13-O-(3-Benzyloxycarbonyl-2,2-dimethyl-4-phenyl-5-oxazolidinecarbonyl)-10-O-(4-pyrrolidinopiperidinocarbonyl)-7-O-triethylsilyl-10-deacetylbaccatin III (Compound 11)

Using the compound (169 mg, 0.20 mmol) of Example 10, reactions and post-treatment were conducted as in Example 2, whereby the title compound (170 mg, 95%) was obtained.

$^1$H-NMR (CDCl$_3$)δ: 0.56(6H,m), 0.89(9H,t,J=8 Hz), 1.15 (3H,s), 1.17(3H,s), 1.63(3H,s), 1.75(3H,s), 1.80(3H,s), 1.89 (3H,s), 2.05(3H,s), 1.45–2.28(11H,m), 2.47(1H,m), 2.70–3.23(4H,m), 3.77(1H,d,J=7 Hz,C3-H), 3.50–3.75(2H,m), 4.08(1H,d,J=9 Hz,C20-H), 4.23(1H,d,J=9 Hz,C20-H), 4.40(2H,br), 4.43(1H,dd,J=10 Hz,7 Hz,C7-H), 4.49(1H,d,J=6 Hz), 4.85(1H,d,J=9 Hz,C5-H), 4.78–5.36(3H,m), 5.62 (1H,d,J=7 Hz,C2-H), 6.20(1H,br,C13-H), 6.35(1H,s,C10-H), 6.74(1H,br), 7.05–7.40(9H,m), 7.47(2H,t,J=8 Hz), 7.61 (1H,t,J=7 Hz), 8.02(2H,d,J=7 Hz).

Example 12

13-O-[3-(tert-Butoxycarbonylamino)-2-hydroxy-3-phenylpropionyl]-10-O-(4-pyrrolidinopiperidinocarbonyl)-10-deacetylbaccatin III (Compound 12)

The compound (85 mg, 0.07 mmol) of Example 11 was dissolved in ethanol (5 ml), followed by the addition of 0.1 N hydrochloric acid (10 ml). The resulting mixture was stirred at room temperature for 18 hours. The solvent was distilled off under reduced pressure, and chloroform was added to the residue. The thus-obtained mixture was washed with a saturated aqueous solution of sodium hydrogencarbonate. The organic layer was dried over anhydrous magnesium sulfate, the solvent was distilled off, and methanol (10 ml), water (1 ml) and 10% palladium on charcoal (40 mg) were then added to the residue. The resulting mixture was stirred for 2 hours at room temperature and atmospheric pressure under a hydrogen atmosphere. The reaction mixture was filtered through a glass filter with Celite distributed thereon. After the filtrate was concentrated, methylene chloride (10 ml) was added to the residue so that the residue was dissolved. To the solution, S-tert-butoxycarbonyl-4,6-dimethyl-2-mercaptopyrimidine (18 mg, 0.075 mmol) and triethylamine (7.5 mg, 0.075 mmol) were added. The resulting mixture was stirred at room temperature for 19 hours and then at 40° C. for 6 days.

Chloroform was added to the reaction mixture, and the resulting mixture was washed with a saturated aqueous solution of sodium hydrogencarbonate. The organic layer was dried over anhydrous magnesium sulfate, and the solvent was distilled off under reduced pressure. The residue was preliminarily purified by chromatography on a silica gel column (chloroform-methanol [9:1]). Further purification was conducted by reverse-phase high-performance column chromatography (eluent: 10 mM potassium dihydrogenphosphate-acetonitrile [3:4]), whereby the title compound (16 mg, 23%) was obtained.

$^1$H-NMR (CDCl$_3$)δ: 1.10(3H,s), 1.24(3H,s), 1.31(9H,s), 1.64(3H,s), 1.85(3H,s), 2.36(3H,s), 1.75–2.59(12H,m), 2.72–3.20(5H,m), 3.39(1H,br), 3.77(1H,d,J=6 Hz,C3-H), 3.38–3.80(2H,m), 4.14(1H,d,J=8 Hz,C20-H), 4.28(1H,d,J=8 Hz,C20-H), 4.29(2H,br), 4.41(1H,br), 4.61(1H,s,C2'-H), 4.94(1H,d,J=8 Hz,C5-H), 5.18–5.42(2H,m), 5.63(1H,d,J=7 Hz,C2-H), 6.23(1H,br,C13-H), 6.24(1H,s,C10-H), 7.36(5H, m), 7.48(2H,t,J=7 Hz), 7.59(1H,t,J=8 Hz), 8.09(2H,d,J=7 Hz). SI-MS m/z: 988 [M+H]$^+$

Example 13

10-O-(4-Morpholinopiperidinocarbonyl)-7-O-triethylsilyl-10-deacetylbaccatin III (Compound 13)

Using 7-O-triethylsilyl-10-deacetylbaccatin III (100 mg, 0.15 mmol) and 4-morpholinopiperidinocarbonyl chloride (40 mg, 0.17 mmol), reactions and post-treatment were conducted as in Example 4, whereby the title compound (125 mg, 96%) was obtained as colorless crystals.

$^1$H-NMR (CDCl$_3$)δ: 0.55–0.63(6H,m,Si—CH$_2$X3), 0.92 (9H,t,J=8 Hz,-MeX3), 1.04(3H,s,C16 or C17-Me), 1.18(3H, s,C16 or C17-Me), 1.40–1.50(1H,m), 1.66(3H,s,C19-Me), 1.82–1.93(3H,m), 2.22–2.30(2H,m,C14-H), 2.25(3H,s,C18-Me), 2.28(3H,s,C4-OAc), 2.30–3.10(8H,m), 2.49–2.55(1H, m,C6-H), 3.74(4H,br-s), 3.90(1H,d,J=7 Hz,C3-H), 4.15(1H, d,J=8 Hz,C20-H), 4.20–4.50(2H,m), 4.30(1H,d,J=8 Hz,C20-H), 4.47(1H,dd,J=7,11 Hz,C7-H), 4.82(1H,t,C13-H), 4.96(1H,d,J=8 Hz,C5-H), 5.63(1H,d,J=7 Hz,C2-H), 6.38 (1H,s,C10-H), 7.46–7.49(2H,m,ArH), 7.58–7.62(1H,m, ArH), 8.10–8.12(2H,m,ArH).

Example 14

10-O-(4-Morpholinopiperidinocarbonyl)-13-O-(3-benzyloxycarbonyl-2,2-dimethyl-4-phenyl-5 -oxazolidinecarbonyl)-7-O-triethylsilyl-10-deacetylbaccatin III (Compound 14)

The compound (210 mg, 0.24 mmol) of Example 13 was dissolved in toluene, followed by the addition of 3-benzyloxycarbonyl-2,2-dimethyl-4-phenyl-5-oxazolidinecarboxylic acid (366 mg, 1.0 mmol), DCC (234 mg, 1.1 mmol) and DMAP (20 mg). The resulting mixture was stirred at room temperature for 2 hours. Post-treatment was conducted as in Example 2, whereby the title compound (280 mg, 91%) was obtained.

$^1$H-NMR (CDCl$_3$)δ: 0.57–0.61(6H,m,Si—CH$_2$X3), 0.92 (9H,t,J=8 Hz,-MeX3), 1.19(6H,s,C16 and C17-Me), 1.40–1.50(1H,m), 1.66(3H,s,C19-Me), 1.67–2.00(4H,m), 1.76(3H,s), 1.82(3H,s), 1.91(3H,s), 2.11(3H,s,C4-OAc), 2.15–2.17(2H,m,C14-H), 2.45–2.52(1H,m,C6-H), 2.49–3.10(7H,m), 3.75(4H,br-s), 3.80(1H,d,J=7 Hz,C3-H), 4.11(1H,d,J=8 Hz,C20-H), 4.12–4.55(2H,m), 4.25(1H,d,J=8 Hz,C20-H), 4.44(1H,dd,J=7,11 Hz,C7-H), 4.51(1H,d,J=6 Hz), 4.88(1H,d,J=8 Hz,C5-H), 4.98(2H,br-s), 5.24(1H,br-s), 5.65(1H,d,J=7 Hz,C2-H), 6.23(1H,t,J=8 Hz,C13-H), 6.38 (1H,s,C10-H), 6.76(1H,br-s,ArH), 7.10–7.45(9H,m,ArH), 7.46–7.50(2H,m,ArH), 7.60–7.64(1H,m,ArH), 8.03–8.05 (2H,m,ArH).

Example 15

13-O-[3-(tert-Butoxycarbonylamino)-2-hydroxy-3-phenylpropionyl]-10-O-(4-morpholinopiperidinocarbonyl)-10-deacetylbaccatin III (Compound 15)

The compound (270 mg, 0.22 mmol) of Example 14 was dissolved in ethanol (70 ml), followed by the addition of 0.1 N hydrochloric acid (22 ml, 2.2 mmol). The resulting mixture was stirred at room temperature for 3 days. A saturated aqueous solution of sodium hydrogencarbonate was added to the reaction mixture, followed by extraction with ethyl acetate. The organic layer was washed with a saturated aqueous solution of sodium chloride, dried over anhydrous sodium sulfate, and then concentrated to dryness under reduced pressure, whereby a colorless oil (230 mg) was obtained.

The compound (210 mg, 0.195 mmol) was then dissolved in methanol-water mixed solvent (10:1, 22 ml), followed by the addition of 10% palladium on charcoal (80 mg). The resulting mixture was stirred for 2.5 hours at room temperature and atmospheric pressure under a hydrogen gas atmosphere. The reaction mixture was filtered and the filtrate was concentrated to dryness under reduced pressure, whereby a colorless oil (160 mg) was obtained.

This compound (70 mg, 0.077 mmol) was dissolved in tetrahydrofuran (20 ml), followed by the addition of di-tert-butyl dicarbonate (20.1 mg, 0.092 mmol) and sodium hydrogencarbonate (50 mg). The resulting mixture was stirred overnight at room temperature under an argon gas atmosphere. Water was added to the reaction mixture, followed by extraction with ethyl acetate. The organic layer was washed with a saturated aqueous solution of sodium chloride, dried over anhydrous sodium sulfate, and then concentrated to dryness under reduced pressure. The residue was purified by chromatography on a silica gel column (chloroform-methanol mixed solvent [96:4]). TLC single-spot fractions were combined together and then concentrated to dryness under reduced pressure, whereby a colorless oil (63 mg, 82%) was obtained.

$^1$H-NMR (CDCl$_3$)δ: 1.14(3H,s,C16 or C17-Me), 1.27 (3H,s,C16 or C17-Me), 1.33(9H,s,t-Bu), 1.56–2.00(5H,m), 1.67(3H,s,C19-Me), 1.87(3H,s,C18-Me), 2.23–2.35(2H,m, C14-H), 2.37(3H,s,C4-OAc), 2.40–3.15(7H,m), 2.49–2.58 (1H,m,C6-H), 3.17(1H,m), 3.70–3.89(4H,m), 3.79(1H, J=7 Hz,C3-H), 4.16–4.26(2H,m), 4.17(1H,d,J=9 Hz,C20-

H), 4.30(1H,d,J=9 Hz,C20-H), 4.44(1H,m,C7-H), 4.62(1H, s,C2'-H), 4.96(1H,d,J=9 Hz,C5-H), 5.27(1H,m,), 5.37(1H, d,J=10 Hz,C3'-H), 5.66(1H,d,J=7 Hz,C2-H), 6.24(1H,m, C13-H), 6.25(1H,s,C10-H), 7.30–7.42(5H,m,ArH), 7.48–7.52(2H,m,ArH), 7.59–7.63(1H,m,ArH), 8.10–8.12 (2H,m,ArH). SI-MS m/z: 1004 [M+H]$^+$

Example 16

13-O-(3-Benzoylamino-2-hydroxy-3-phenylpropionyl)-10-O-(4-morpholinopiperidinocarbonyl)-10-deacetylbaccatin III (Compound 16)

Using the compound (270 mg, 0.22 mol) of Example 14, hydrolysis was conducted with 0.1 N hydrochloric acid in a similar manner as in Example 15. Catalytic reduction was then carried out with 10% palladium on charcoal, and post-treatment was conducted, whereby a colorless oil (160 mg) was obtained.

This compound (70 mg, 0.077 mmol) was dissolved in tetrahydrofuran (20 ml), followed by the addition of benzoic anhydride (21 mg, 0.092 mmol) and sodium hydrogencarbonate (50 mg). The resulting mixture was stirred overnight at room temperature under an argon gas atmosphere. Water was added to the reaction mixture, followed by extraction with ethyl acetate. The organic layer was washed with a saturated aqueous solution of sodium chloride, dried over anhydrous sodium sulfate, and then concentrated to dryness under reduced pressure. The residue was purified by chromatography on a silica gel column (chloroform-methanol mixed solvent (96:41). TLC single-spot fractions were combined together and concentrated to dryness under reduced pressure, whereby a colorless oil (65 mg, 84%) was obtained.

$^1$H-NMR (CDCl$_3$)δ: 1.13(3H,s,C16 or C17-Me), 1.24 (3H,s,C16 or C17-Me), 1.56–1.95(5H,m), 1.67(3H,s,C19-Me), 1.76(1H,s), 1.81(3H,s,C18-Me), 2.27–2.37(2H,m,C14-H), 2.39(3H,s,C4-OAc), 2.40–3.17(7H,m), 2.50–2.58(1H, m,C6-H), 3.14(1H,m), 3.57(1H,d,J=6 Hz), 3.69–3.83(4H, m), 3.79(1H,d,J=7 Hz,C3-H), 4.11–4.24(2H,m), 4.20(1H,d, J=9 Hz,C20-H), 4.30(1H,d,J=9 Hz,C20-H), 4.43(1H,m,C7-H), 4.79(1H,s,C'2-H), 4.96(1H,d,J=9 Hz,C5-H), 5.66(1H,d, J=7 Hz,C2-H), 5.79(1H,d,J=10 Hz,C3'-H), 6.24(1H,s,C10-H), 6.25(1H,m,C13-H), 6.99(1H,d,J=9 Hz,C3'-NH), 7.34–7.55(10H,m,ArH), 7.58–7.63(1H,m,ArH), 7.72–7.77 (2H,m,ArH), 8.11–8.15(2H,m,ArH). SI-MS m/z: 1008 [M+H]$^+$

Example 17

10-O-[3-(4-Piperidinopiperidinocarbonyl)propionyl]-7-O-triethylsilyl-10-deacetylbaccatin III (Compound 17)

1) 3-(4-Piperidinopiperidinocarbonyl)propionic acid (0.26 g, 0.97 mmol) and DCC (0.25 g, 1.2 mmol) were dissolved in methylene chloride, followed by the addition of 4-nitrothiophenol (0.23 g, 1.2 mmol). The resulting mixture was stirred for 16 hours at 4° C. and then overnight at room temperature. The reaction mixture was filtered. After the filtrate was concentrated, the residue was purified by chromatography on a silica gel column (chloroform-acetone mixed solvent [10:1→5:1], whereby S-4-nitrophenyl 3-(4-piperidinopiperidinocarbonyl)propanethioate (196 mg, 50%) was obtained.

$^1$H-NMR (CDCl$_3$)δ: 1.44(4H,m), 1.59(4H,m), 1.86(2H,t, J=13 Hz), 2.55(6H,m), 2.73(2H,t,J=7 Hz), 3.06(3H,m), 3.89 (1H,d,J=13 Hz), 4.63(1H,d,J=13 Hz), 7.62(2H,d,J=9 Hz), 8.23(2H,d,J=9 Hz), 2) 7-O-Triethylsilyl-10-deacetylbaccatin III (105 mg, 0.16 mmol) was dissolved in THF, followed by stirring for 15 minutes over an acetone bath of −40° C. A solution of n-butyllithium (0.20 mmol) in hexane was added, and the resulting mixture was stirred further for 30 minutes. To the thus-obtained solution, a solution of the above-described thioester (94 mg, 0.23 mmol) in THF was added. The temperature of the mixture was raised from −40° C. to room temperature, at which the mixture was stirred overnight. Chloroform was added to the reaction mixture, and the thus-obtained mixture was washed with a saturated aqueous solution of ammonium chloride and hen with a saturated aqueous solution of sodium hydrogencarbonate. The organic layer was dried over anhydrous magnesium sulfate, the solvent was distilled off under reduced pressure, and the residue was then purified by chromatography on a silica gel column (chloroform-methanol mixed solvent [10:1]), whereby the title compound (98 mg, 93%) was obtained.

$^1$H-NMR (CDCl$_3$)δ: 0.59(6H,m), 0.92(9H,t,J=8 Hz), 1.05 (3H,d,J=6 Hz), 1.17(3H,d,J=3 Hz), 1.67(3H,s), 1.86(1H,m), 1.35–2.04(10H,m), 2.19(3H,s), 2.29(3H,s), 2.45–2.90(10H, m), 3.05(1H,brs), 3.87(1H,d,J=7 Hz,C3-H), 4.01(1H,brs), 4.13(1H,d,J=9 Hz,C20-H), 4.29(1H,d,J=8 Hz,C20-H), 4.45 (1H,dd,J=10,6 Hz,C7-H), 4.76(1H,brs), 4.85(1H,s,C13-H), 4.95(1H,d,J=9 Hz,C5-H), 5.62(1H,d,J=7 Hz,C2-H), 6.45 (1H,s,C10-H), 7.47(2H,t,J=8 Hz), 7.60(1H,t,J=8 Hz), 8.10 (2H,d,J=8 Hz).

Example 18

13-O-(3-Benzyloxycarbonyl-2,2-dimethyl-4-phenyl-5-oxazolidinecarbonyl)-10-O-[3-(4-piperidinopiperidinocarbonyl)propionyl]-7-O-triethylsilyl-10-deacetylbaccatin III (Compound 18)

The compound (151 mg, 0.17 mmol) of Example 17 was dissolved in toluene, followed by the addition of 3-benzyloxycarbonyl-2,2-dimethyl-4-phenyl-5-oxazolidinecarboxylic acid (123 mg, 0.35 mmol), DCC (72 mg, 0.35 mmol) and DMAP (5 mg). The resulting mixture was stirred overnight at room temperature. The reaction mixture was filtered. After the filtrate was concentrated, chloroform was added to the residue. The thus-obtained mixture was washed with a saturated aqueous solution of sodium hydrogencarbonate. The organic layer was dried over anhydrous magnesium sulfate, the solvent was distilled off under reduced pressure, and the residue was purified by chromatography on a silica gel column (chloroform-methanol mixed solvent [19:1]), whereby the title compound (196 mg, 94%) was obtained.

$^1$H-NMR (CDCl$_3$)δ: 0.56(6H,m), 0.91(9H,t,J=8 Hz), 1.19 (6H,s), 1.66(3H,s), 1.77(3H,s), 1.82(3H,s), 1.89(3H,s), 2.04 (3H,s), 1.40–2.10(11H,m), 2.15(3H,d,J=8 Hz), 2.48–3.03 (8H,br), 3.78(1H,d,J=7 Hz,C3-H), 4.09(1H,d,J=9 Hz,C20-H), 4.01(1H,br), 4.24(1H,d,J=8 Hz,C20-H), 4.44(1H,dd,J= 11,7 Hz,C7-H), 4.51(1H,d,J=6 Hz), 4.88(1H,d,J=10 Hz,C5-H), 4.65–4.96(3H,br), 5.23(1H,s), 5.63(1H,d,J=7 Hz,C2-H), 6.21(1H,t,J=9 Hz,C13-H), 6.40(1H,s,C10-H), 6.77(1H,br), 7.22–7.40(9H,m), 7.48(2H,t,J=8 Hz), 7.62(1H,t,J=7 Hz), 8.03(2H,d,J=7 Hz).

Example 19

13-O-[3-(tert-Butoxycarbonylamino)-2-hydroxy-3-phenylpropionyl]-10-O-[3-(4-piperidinopiperidinocarbonyl)propionyl]-10-deacetylbaccatin III (Compound 19)

The compound (98 mg, 0.079 mmol) of Example 18 was dissolved in ethanol (5 ml), followed by the addition of 0.1 N hydrochloric acid (8.5 ml). The resulting mixture was stirred at room temperature for 22 hours. After the solvent was distilled off under reduced pressure, chloroform was added to the residue, and the thus-obtained mixture was washed with a saturated aqueous solution of sodium hydrogencarbonate. The organic layer was dried over anhydrous magnesium sulfate, and the solvent was distilled off under reduced pressure. Methanol (10 ml), water (1 ml) and 10% palladium on charcoal (40 mg) were added to the residue, followed by stirring for 4 hours at room temperature and atmospheric pressure under a hydrogen. gas atmosphere. The resulting mixture was filtered through a glass filter with Celite distributed thereon. After the filtrate was concentrated, methylene chloride (10 ml) was added to the residue so that the residue was dissolved. S-tert-Butoxycarbonyl-4,6-dimethyl-2-mercaptopyrimidine (19 mg, 0.08 mmol) and triethylamine (8 mg, 0.08 mmol) were added, followed by stirring at room temperature for 6 days.

Chloroform was added to the reaction mixture, and the resulting mixture was washed with a saturated aqueous solution of sodium hydrogencarbonate. The organic layer was dried over anhydrous magnesium sulfate, and the solvent was distilled off under reduced pressure. The residue was preliminarily purified by chromatography on a silica gel column (chloroform-methanol mixed solvent [9:1]). Further purification was conducted by reverse-phase high-performance column chromatography (eluent: 10 mM potassium dihydrogen-phosphate-acetonitrile [3:4]), whereby the title compound (7 mg, 8%) was obtained.

$^1$H-NMR (CDCl$_3$)δ: 1.15(3H,s), 1.26(3H,s), 1.34(9H,s), 1.67(3H,d,J=8 Hz), 1.86(3H,s), 1.35–2.05(11H,m), 2.37(3H, s), 2.25–3.10(10H,m), 3.35(1H,s), 3.80(1H,d,J=7 Hz,C3-H), 4.15(1H,br), 4.16(1H,d,J=9 Hz,C20-H), 4.30(1H,d,J=8 Hz, C20-H), 4.39(1H,m,C7-H), 4.63(1H,s,C2'-H), 4.82(1H,br), 4.94(1H,d,J=8 Hz,C5-H), 5.26(1H,s), 5.36(1H,d,J=10 Hz, C3'-H), 5.66(1H,d,J=7 Hz,C2-H), 6.22(1H,br,C13-H), 6.30 (1H,s,C10-H), 7.36(5H,m), 7.50(2H,t,J=8 Hz), 7.61(1H,t,J= 7 Hz), 8.11(2H,d,J=7 Hz). SI-MS m/z: 1058 [M+H]$^+$

Example 20

10-O-(4-(4-Piperidinopiperidinocarbonyl)butyryl]-7-O-triethylsilyl-10-deacetylbaccatin III (Compound 20)

1) From 4-(4-piperidinopiperidinocarbonyl)butyric acid (0.49 g, 1.7 mmol), DCC (433 mg, 2.1 mmol) and 4-nitrothiophenol (407 mg, 2.1 mmol), S-4-nitrophenyl 4-(4-piperidinopiperidinocarbonyl)butanethioate (355 mg, 50%) was obtained by conducting a reaction and post-treatment as in Example 17, 1).

$^1$H-NMR (CDCl$_3$)δ: 1.35–2.04(10H,m), 2.04(2H,m), 2.40(2H,t,J=7 Hz), 2.51(6H,m), 2.82(2H,t,J=7 Hz), 2.98 (1H,t,J=12 Hz), 3.87(1H,d,J=13 Hz), 4.66(1H,d,J=10 Hz), 7.58(2H,d,J=9 Hz), 8.23(2H,d,J=9 Hz).

2) From 7-O-triethylsilyl-10-deacetylbaccatin III (131 mg, 0.20 mmol), a solution of n-butyllithium (0.24 mmol) and the above-described thioester (114 mg, 0.31 mmol), the title compound (169 mg, 100%) was obtained by conducting reactions and post-treatment as in Example 17, 2).

$^1$H-NMR (CDCl$_3$)δ: 0.56(6H,m), 0.90(9H,t,J=8 Hz), 1.03 (3H,d,J=3 Hz), 1.15(3H,s), 1.65(3H,s), 2.16(3H,s), 2.27(3H, s), 2.20–2.90(12H,m), 2.97(1H,m), 3.85(1H,d,J=7 Hz,C3-H), 4.02(1H,m), 4.12(1H,d,J=8 Hz,C20-H), 4.28(1H,d,J=9 Hz,C20-H), 4.48(1H,dd,J=10,7 Hz,C7-H), 4.72(1H,br), 4.83 (1H,br,C13-H), 4.94(1H,d,J=9 Hz,C5-H), 5.60(1H,d,J=7 Hz,C2-H), 6.48(1H,s,C10-H), 7.45(2H,t,J=8 Hz), 7.58(1H, t,J=7 Hz), 8.08(2H,d,J=8 Hz).

Example 21

13-O-(3-Benzyloxycarbonyl-2,2-dimethyl-4-phenyl-5-oxazolidinecarbonyl)-10-O-[4-(4-piperidino-piperidinocarbonyl)butyryl]-7-O-triethylsilyl-10-deacetylbaccatin III (Compound 21)

The compound (169 mg, 0.18 mmol) of Example 20 was dissolved in toluene, followed by the addition of 3-benzyloxycarbonyl-2,2-dimethyl-4-phenyl-5-oxazolidinecarboxylic acid (151 mg, 0.42 mmol), DCC (87 mg, 0.42 mmol) and DMAP (5 mg). The resulting mixture was stirred overnight at room temperature. Post-treatment was conducted as in Example 18, whereby the title compound (218 mg, 96%) was obtained.

$^1$H-NMR (CDCl$_3$)δ: 0.55(6H,m), 0.89(9H,t,J=8 Hz), 1.17 (6H,s), 1.62(3H,s), 1.75(3H,s), 1.81(3H,s), 1.86(3H,s), 1.86 (3H,s), 2.00(3H,s), 1.25–2.10(16H,m), 2.14(3H,d,J=9 Hz), 2.18–2.83(11H,m), 3.02–3.58(4H,m), 3.78(1H,d,J=7 Hz,C3-H), 4.09(1H,d,J=8 Hz,C20-H), 4.13(1H,br), 4.23 (1H,d,J=8 Hz,C20-H), 4.44(1H,m,C7-H), 4.49(1H,d,J=6 Hz), 4.85(1H,d,J=9 Hz,C5-H), 4.78–5.05(3H,m), 5.19(1H, s), 5.61(1H,d,J=7 Hz,C2-H), 6.19(1H,br,C13-H), 6.45(1H, s,C10-H), 6.72(1H,br), 7.09–7.45(9H,m), 7.47(2H,t,J=8 Hz), 7.61(1H,t,J=7 Hz), 8.03(2H,d,J=7 Hz).

Example 22

13-O-[3-(tert-Butoxycarbonylamino)-2-hydroxy-3-phenylpropionyl]-10-O-[4-(4-piperidinopiperidinocarbonyl)butyryl]-10-deacetylbaccatin III (Compound 22)

The compound (70 mg, 0.056 mmol) of Example 21 was dissolved in ethanol (5 ml), followed by the addition of 0.1 N hydrochloric acid (7 ml). The resulting mixture was stirred at room temperature for 18 hours. The solvent was distilled off under reduced pressure, chloroform was added to the residue, and the thus-obtained mixture was washed with a saturated aqueous solution of sodium hydrogencarbonate. The organic layer was dried over anhydrous magnesium sulfate, the solvent was distilled off under reduced pressure, and methanol (10 ml), water (1 ml) and 10% palladium on charcoal (40 mg) were then added to the residue. The resulting mixture was stirred for 2 hours at room temperature and atmospheric pressure under a hydrogen gas atmosphere. The resulting mixture was filtered through a glass filter with Celite distributed thereon. After the filtrate was concentrated, methylene chloride (10 ml) was added to the residue so that the residue was dissolved. S-tert-Butoxycarbonyl-4,6-dimethyl-2-mercaptopyrimidine (17 mg, 0.07 mmol) and triethylamine (7 mg, 0.07 mmol) were added, followed by stirring at []room temperature for 12 hours and further at 40° C. for 5 days. Post-treatment was conducted as in Example 19, whereby the title compound (16 mg, 27%) was obtained.

$^1$H-NMR (CDCl$_3$)δ: 1.12(3H,s), 1.23(3H,s), 1.32(9H,s), 1.66(3H,d,J=8 Hz), 1.85(3H,s), 1.38–2.15(13H,m), 2.34 (3H,s), 2.18–2.85(9H,m), 2.98(1H,m), 3.79(1H,d,J=7 Hz,C3-H), 4.01(1H,br), 4.14(1H,d,J=8 Hz,C20-H), 4.28 (1H,d,J=8 Hz,C20-H), 4.37(1H,m,C7-H), 4.61(1H,s,C2'-H), 4.73(1H,br), 4.93(1H,d,J=9 Hz,C5-H), 5.25(1H,br), 5.36 (1H,d,J=9 Hz,C3'-H), 5.64(1H,d,J=7 Hz,C2-H), 6.20(1H,br, C13-H), 6.32(1H,s,C10-H), 7.36(5H,m), 7.49(2H,t,J=8 Hz), 7.59(1H,t,J=7 Hz), 8.08(2H,d,J=8 Hz).

SI-MS m/z: 1072 [M+H]$^+$

Example 23

10-O-[(4-Piperidinopiperidinocarbonyloxy)acetyl]-7-O-triethylsilyl-10-deacetylbaccatin III (Compound 23)

1) From (4-piperidinopiperidinocarbonyloxy)acetic acid (0.14 g, 0.50 mmol), DCC (0.12 g, 0.60 mmol) and 2-fluorophenol (0.05 g, 0.60 mmol), 2-fluorophenyl (4-piperidinopiperidinocarbonyloxy)acetate (97 mg, 53%) was obtained by conducting a reaction and post-treatment as in Example 17, 1).

$^1$H-NMR (CDCl$_3$)δ: 1.08–1.98(10H,m), 2.49(5H,br), 2.76(2H,br), 4.22(2H,m), 4.88(2H,s), 7.16(4H,m).

2) From 7-O-triethylsilyl-10-deacetylbaccatin III (100 mg, 0.15 mmol), a solution of n-butyllithium (0.16 mmol) in hexane and the above-described ester (97 mg, 0.27 mmol), the title compound (35 mg, 76%) was obtained by conducting reactions and post-treatment as in Example 17, 2).

$^1$H-NMR (CDCl$_3$)δ: 0.55(6H,m), 0.90(9H,t,J=8 Hz), 1.02 (3H,s), 1.14(3H,s), 1.65(3H,s), 1.18–2.10(13H,m), 2.18(3H, s), 2.26(3H,s), 2.40–2.95(8H,m), 3.84(1H,d,J=7 Hz,C3-H), 4.12(1H,d,J=9 Hz,C20-H), 4.27(2H,br), 4.28(1H,d,J=9 Hz,C20-H), 4.46(1H,dd,J=11,7 Hz,C7-H), 4.40–4.90(3H, m), 4.94(1H,d,J=8 Hz,C5-H), 5.60(1H,d,J=7 Hz,C2-H), 6.44(1H,s,C10-H), 7.46(2H,t,J=8 Hz), 7.59(1H,t,J=7 Hz), 8.08(2H,d,J=7 Hz).

Example 24

13-O-(3-Benzyloxycarbonyl-2,2-dimethyl-4-phenyl-5-oxazolidinecarbonyl)-10-O-[(4-piperidinopiperidinocarbonyloxy)acetyl]-7-O-triethylsilyl-10-deacetylbaccatin III (Compound 24)

The compound (35 mg, 0.04 mmol) of Example 23 was dissolved in toluene, followed by the addition of 3-benzyloxycarbonyl-2,2-dimethyl-4-phenyl-5-oxazolidinecarboxylic acid (34 mg, 0.10 mmol), DCC (21 mg, 0.10 mmol) and DMAP (2 mg). The resulting mixture was stirred overnight at room temperature. Post-treatment was conducted as in Example 18, whereby the title compound (37 mg, 78%) was obtained.

$^1$H-NMR (CDCl$_3$)δ: 0.56(6H,m), 0.91(9H,t,J=8 Hz), 1.19 (6H,s), 1.70(3H,s), 1.77(3H,s), 1.82(3H,s), 1.91(3H,s), 2.07 (3H,s), 1.40–2.22(13H,m), 2.47(1H,m), 2.55–3.50(7H,m), 3.76(1H,d,J=7 Hz,C3-H), 4.09(1H,d,J=8 Hz,C20-H), 4.24 (1H,d,J=9 Hz,C20-H), 4.34(1H,br), 4.44(1H,dd,J=10,7 Hz,C7-H), 4.51(1H,d,J=6 Hz), 4.87(1H,d,J=9 Hz,C5-H), 4.50–5.15(4H,m), 5.23(1H,br), 5.63(1H,d,J=7 Hz,C2-H), 6.22(1H,t,J=9 Hz,C13-H), 6.42(1H,s,C10-H), 6.77(1H,br), 7.08–7.40(9H,m), 7.48(2H,t,J=8 Hz), 7.62(1H,t,J=7 Hz), 8.03(2H,d,J=7 Hz).

Example 25

13-O-[3-(tert-Butoxycarbonylamino)-2-hydroxy-3-phenylpropionyl]-10-O-[(4-piperidinopiperidinocarbonyloxy)acetyl]-10-deacetylbaccatin III (Compound 25)

Using the compound (37 mg, 0.03 mmol) of Example 24, the title compound (1 mg, 3%) was obtained by conducting reactions and treatment as in Example 19.

$^1$H-NMR (CDCl$_3$)δ: 1.14(3H,s), 1.28(3H,s), 1.34(9H,s), 1.68(3H,s), 1.87(3H,s), 1.35–1.99(13H,s), 2.38(3H,s), 2.18–2.85(8H,m), 3.37(1H,br), 3.79(1H,d,J=7 Hz,C3-H), 4.16(1H,d,J=9 Hz,C20-H), 4.31(1H,d,J=8 Hz,C20-H), 4.10–4.45(4H,m), 4.63(1H,s,C2'-H), 4.92(1H,br), 4.94(1H, d,J=9 Hz,C5-H), 5.25(1H,br), 5.35(1H,d,J=9 Hz,C3'-H), 5.67(1H,d,J=8 Hz,C2-H), 6.22(1H,br,C13-H), 6.35(1H,s, C10-H), 7.36(5H,m), 7.52(2H,t,J=8 Hz), 7.60(1H,t,J=8 Hz), 8.10(2H,d,J=8 Hz). SI-MS m/z: 1060 [M+H]$^+$

Example 26

10-O-[(4-Piperidinopiperidinocarbonylamino)acetyl]-7-O-triethylsilyl-10-deacetylbaccatin III (Compound 26)

1) From (4-piperidinopiperidinocarbonylamino)acetic acid (0.14 g, 0.50 mmol), DCC (0.12 g, 0.6 mmol) and 2-fluorophenol (0.05 g, 0.6 mmol), 2-fluorophenyl (4-piperidinopiperidinocarbonylamino)acetate (98 mg, 54%) was obtained by conducting a reaction and post-treatment as in Example 17, 1).

$^1$H-NMR (CDCl$_3$)δ: 1.36–1.92(10H,m), 2.51(1H,br), 2.79(2H,t,J=11 Hz), 4.40(2H,d,J=13 Hz), 4.31(2H,d,J=6 Hz), 5.03(1H,br), 7.16(4H,m).

2) From 7-O-triethylsilyl-10-deacetylbaccatin III (132 mg, 0.20 mmol), a solution of n-butyllithium (0.24 mmol) in hexane and the above-described ester (98 mg, 0.27 mmol), the title compound (101 mg, 79%) was obtained by conducting reactions and post-treatment as in Example 17, 2).

$^1$H-NMR (CDCl$_3$)δ: 0.57(6H,m), 0.92(9H,t,J=8 Hz), 1.04 (3H,s), 1.16(3H,s), 1.28–2.12(14H,s), 1.68(3H,s), 2.18(3H, s), 2.29(3H,s), 2.44–2.95(7H,s), 3.87(1H,d,J=7 Hz,C3-H), 3.96–4.22(5H,m), 4.30(1H,d,J=8 Hz,C20-H), 4.49(1H,dd,J= 7,10Hz,C7-H), 4.84(1H,br,C13-H), 4.90–5.02(2H,m), 5.12 (1H,br), 5.62(1H,d,J=7 Hz,C2-H), 6.47(1H,s,C10-H), 7.48 (2H,t,J=8 Hz), 7.60(1H,t,J=7 Hz), 8.10(2H,d,J=7 Hz).

Example 27

13-O-(3-Benzyloxycarbonyl-2,2-dimethyl-4-phenyl-5-oxazolidinecarbonyl)-10-O-[(4-piperidinopiperidinocarbonylamino)acetyl]-7-O-triethylsilyl-10-deacetylbaccatin III (Compound 27)

Using the compound (101 mg, 0.11 mmol) of Example 26, the title compound (79 mg, 58%) was obtained by conducting reactions and treatment as in Example 2.

$^1$H-NMR (CDCl$_3$)δ: 0.54(6H,m), 0.89(9H,t,J=8 Hz), 1.16 (6H,s), 1.69(3H,s), 1.75(3H,s), 1.81(3H,s), 1.88(3H,s), 1.35–2.16(14H,m), 2.03(3H,s), 2.42–2.88(7H,m), 3.75(1H, J=7 Hz,C3-H), 4.03–4.16(5H,m), 4.22(1H,d,J=8 Hz,C20-H), 4.43(1H,dd,J=7,10Hz,C7-H), 4.49(1H,d,J=7 Hz), 4.85 (1H,d,J=8 Hz,C5-H), 5.04(2H,br), 5.09(1H,s), 5.21(1H,br), 5.61(1H,d,J=7 Hz,C2-H), 6.19(1H,t,J=9 Hz,C13-H), 6.42 (1H,s,C10-H), 6.73(1H,br), 7.10–7.40(9H,m), 7.46(2H,t, J=8 Hz), 7.60(1H,t,J=7 Hz), 8.01(2H,d,J=7 Hz).

Example 28

13-O-[3-(tert-Butoxycarbonylamino)-2-hydroxy-3-phenylpropionyl]-10-O-[(4-piperidinopiperidinocarbonylamino)acetyl]-10-deacetylbaccatin III (Compound 28)

Using the compound (79 mg, 0.06 mmol) of Example 27, the title compound (17 mg, 25%) was obtained by conducting reactions and treatment as in Example 19.

$^1$H-NMR (CDCl$_3$)δ: 1.12(3H,s), 1.24(3H,s), 1.32(9H,s), 1.65(3H,s), 1.85(3H,s), 1.50–1.98(13H,s), 2.35(3H,s), 2.25–2.87(8H,m), 3.41(1H,br), 3.77(1H,d,J=7 Hz,C3-H), 4.14(1H,d,J=8 Hz,C20-H), 4.27(1H,d,J=8 Hz,C20-H), 4.10–4.34(4H,m), 4.35(1H,m,C7-H), 4.61(1H,s,C2'-H), 4.92(1H,d,J=9 Hz,C5-H), 5.24(1H,br), 5.41(1H,br,C3'-H), 5.60(1H,br), 5.63(1H,d,J=7 Hz,C2-H), 6.20(1H,br,C13-H), 6.34(1H,s,C10-H), 7.35(5H,m), 7.42(2H,t,J=8 Hz), 7.59 (1H,t,J=8 Hz), 8.06(2H,d,J=8 Hz). SI-MS m/z: 1059 [M+H]$^+$

Example 29

10-O-[3-(4-Piperidinopiperidinocarbonylamino) propionyl]-7-O-triethylsilyl-10-deacetylbaccatin III (Compound 29)

1) From 3-(4-piperidinopiperidinocarbonylamino) propionic acid (0.14 g, 0.50 mmol), DCC (0.12 g, 0.60 mmol) and 2-fluorophenol (0.05 g, 0.6 mmol), 2-fluorophenyl 3-(4-piperidinopiperidinocarbonylamino) propionate (98 mg, 52%) was obtained by conducting a reaction and post-treatment as in Example 17, 1).

$^1$H-NMR (CDCl$_3$)δ: 1.39–1.90(10H,m), 2.29–2.65(5H, m), 2.73(2H,t,J=11 Hz), 2.84(2H,t,J=6 Hz), 3.66(2H,q,J=6 Hz), 3.96(2H,d,J=13 Hz), 5.11(1H,br), 7.12(4H,m).

2) From 7-O-triethylsilyl-10-deacetylbaccatin III (132 mg, 0.20 mmol), a solution of n-butyllithium (0.24 mmol) in hexane and the above-described ester (98 mg, 0.26 mmol), the title compound (92 mg, 81%) was obtained by conducting reactions and post-treatment as in Example 17, 2).

$^1$H-NMR (CDCl$_3$)δ: 0.58(6H,m), 0.92(9H,t,J=8 Hz), 1.05 (3H,s), 1.16(3H,s), 1.68(3H,s), 1.25–2.15(13H,m), 2.18(3H, s), 2.31(3H,s), 2.25–2.95(10H,m), 3.61(2H,m), 3.89(1H,d, J=7 Hz,C3-H), 4.14(1H,d,J=9 Hz,C20-H), 4.28(2H,br), 4.32 (1H,d,J=8 Hz,C20-H), 4.52(1H,dd,J=10,7 Hz,C7-H), 4.85 (1H,br,C13-H), 4.97(1H,d,J=10 Hz,C5-H), 5.62(1H,d,J=7 Hz,C2-H), 6.20(1H,s), 6.57(1H,s,C10-H), 7.48(2H,t,J=8 Hz), 7.61(1H,t,J=7 Hz), 8.10(2H,d,J=7 Hz).

Example 30

13-O-(3-Benzyloxycarbonyl-2,2-dimethyl-4-phenyl-5-oxazolidinecarbonyl)-10-O-[3-(4-piperidinopiperidinocarbonylamino)propionyl]-7-O-triethylsilyl-10-deacetylbaccatin III (Compound 30)

Using the compound (92 mg, 0.10 mmol) of Example 29, the title compound (107 mg, 85%) was obtained by conducting reactions and treatment as in Example 2.

$^1$H-NMR (CDCl$_3$)δ: 0.55(6H,m), 0.89(9H,t,J=8 Hz), 1.16 (3H,s), 1.18(3H,s), 1.30–2.20(14H,m), 1.74(3H,s), 1.75(3H, s), 1.81(3H,s), 1.88(3H,s), 2.01(3H,s), 2.42–2.83(9H,m), 3.59(2H,m), 3.78(1H,d,J=7 Hz,C3-H), 4.08(1H,d,J=8 Hz,C20-H), 4.24(1H,d,J=9 Hz,C20-H), 4.30(2H,br), 4.46 (1H,dd,J=7,11,C7-H), 4.49(1H,d,J=7 Hz), 4.86(1H,d,J=9 Hz,C5-H), 4.95(2H,br), 5.21(1H,br), 5.61(1H,d,J=7 Hz,C2-H), 6.18(1H,br), 6.20(1H,br,C13-H), 6.52(1H,s,C10-H), 6.73(1H,br), 7.08–7.45(9H,m), 7.47(2H,t,J=8 Hz), 7.61(1H, t,J=7 Hz), 8.01(2H,d,J=7 Hz).

Example 31

13-O-[3-(tert-Butoxycarbonylamino)-2-hydroxy-3-phenylpropionyl]-10-O-[3-(4-piperidinopiperidinocarbonylamino)propionyl]-10-deacetylbaccatin III (Compound 31)

Using the compound (54 mg, 0.04 mmol) of Example 30, the title compound (16 mg, 35%) was obtained by conducting reactions and treatment as in Example 19.

$^1$H-NMR (CDCl$_3$)δ: 1.14(3H,s), 1.23(3H,s), 1.32(9H,s), 1.66(3H,s), 1.86(3H,s), 1.42–2.10(12H,s), 2.21–2.34(3H, m), 2.34(3H,s), 2.50–2.98(7H,m), 3.52(2H,m), 3.77(1H,br), 3.80(1H,d,J=7 Hz,C3-H), 4.09(1H,br), 4.13(1H,d,J=8 Hz,C20-H), 4.26(1H,br), 4.27(1H,d,J=9 Hz,C20-H), 4.35 (1H,m,C7-H), 4.61(1H,s,C2'-H), 4.92(1H,d,J=8 Hz,C5-H), 5.23(1H,br), 5.39(1H,br,C3'-H), 5.64(1H,d,J=6 Hz,C2-H), 6.18(1H,br,C13-H), 6.44(1H,s,C10-H), 7.36(5H,m), 7.48 (2H,t,J=8 Hz), 7.59(1H,t,J=7 Hz), 8.08(2H,d,J=8 Hz). SI-MS m/z: 1073 [M+H]$^+$

Example 32

13-O-[3-Benzoylamino-2-hydroxy-3-phenylpropionyl]-10-O-[3-(4-piperidinopiperidinocarbonylamino)propionyl]-10-deacetylbaccatin III (Compound 32)

The compound (54 mg, 0.04 mmol) of Example 30 was dissolved in ethyl alcohol (4 ml), followed by the addition of 0.1 N hydrochloric acid (4 ml). The resulting mixture was stirred at room temperature for 20 hours. The solvent was distilled off under reduced pressure, and the residue was dissolved in chloroform. The thus-obtained solution was washed with a 7% aqueous solution of sodium hydrogen carbonate. The organic layer was dried over anhydrous magnesium sulfate, and the solvent was distilled off under reduced pressure. The residue was dissolved in a mixed solvent consisting of methyl alcohol (5 ml) and water (0.5 ml), to which 10% palladium on charcoal (10 mg) was added. The resulting mixture was stirred for 2 hours at room temperature and atmospheric pressure under a hydrogen gas atmosphere. The reaction mixture was filtered through a glass filter with Celite distributed thereon, and the filtrate was concentrated under reduced pressure. The residue was dissolved in methylene chloride (5 ml), followed by the addition of benzoyl chloride (4 mg, 0.03 mmol) and triethylamine (0.03 mmol). The thus-obtained mixture was stirred at 0° C. for 0.5 hour. Chloroform was added to the reaction mixture, and the thus-obtained mixture was washed with a 7% aqueous solution of sodium hydrogencarbonate. The organic layer was dried over anhydrous magnesium sulfate, and the solvent was distilled off under reduced pressure. The residue was preliminarily purified by chromatography on a silica gel column (chloroform-methanol mixed solvent [9:1]). Further purification was conducted by reverse-phase high-performance column chromatography (eluent: 10 mM potassium dihydrogen-phosphate-acetonitrile [1:1]), whereby the title compound (16 mg, 35%) was obtained.

$^1$H-NMR (CDCl$_3$)δ: 1.14(3H,s), 1.23(3H,s), 1.32(9H,s), 1.66(3H,s), 1.86(3H,s), 1.42–2.10(12H,m), 2.21–2.34(3H, m), 2.34(3H,s), 2.50–2.98(7H,m), 3.52(2H,m), 3.77(1H,br), 3.80(1H,d,J=7 Hz,C3-H), 4.09(1H,br), 4.13(1H,d,J=8 Hz,C20-H), 4.26(1H,br), 4.27(1H,d,J=9 Hz,C20-H), 4.35 (1H,m,C7-H), 4.61(1H,s,C2'-H), 4.92(1H,d,J=8 Hz,C5-H), 5.23(1H,br), 5.39(1H,br,C3'-H), 5.64(1H,d,J=6 Hz,C2-H), 6.18(1H,br,C13-H), 6.44(1H,s,C10-H), 7.36(5H,m), 7.48 (2H,t,J=8 Hz), 7.59(1H,t,J=7 Hz), 8.08(2H,d,J=8 Hz). SI-MS m/z: 1077 [M+H]$^+$

Example 33

10-O-(4-Benzyloxycarbonylpiperazinocarbonyl)-7-O-triethylsilyl-10-deacetylbaccatin III (Compound 33)

Using 7-O-triethylsilyl-10-deacetylbaccatin III (100 mg, 0.15 mmol) and 4-benzyloxycarbonylpiperazinocarbonyl chloride (54 mg, 0.19 mmol), the title compound (36 mg, 27%) was obtained as colorless crystals by conducting reactions and post-treatment as in Example 4.

$^1$H-NMR (CDCl$_3$)δ: 0.48–0.55(6H,m,Si—CH$_2$X3), 0.85 (9H,t,J=8 Hz,-MeX3), 0.96(3H,s,C-16 or C17-Me), 1.08 (3H,s,C-16 or C17-Me), 1.60(3H,s,C19-Me), 1.76–1.83(1H, m,C6-H), 2.15–2.28(2H,m,C14-H), 2.16(3H,s,C18-Me), 2.21(3H,s,C4-OAc), 2.41–2.49(1H,m,C6-H), 3.26(2H,br-s), 3.40(2H,br-s), 3.58(3H,br-s), 3.80(1H,br-s), 3.81(1H,d,J=7 Hz,C3-H), 4.07(1H,d,J=8 Hz,C20-H), 4.23(1H,d,J=8 Hz,C20-H), 4.41(1H,dd,J=7,11 Hz,C7-H), 4.75(1H,t,C13-H), 4.89(1H,d,J=8 Hz,C5-H), 5.08(2H,s,—CH$_2$—) 5.55(1H, d,J=7 Hz,C2-H), 6.33(1H,s,C10-H), 7.25–7.31(5H,m,ArH), 7.38–7.42(2H,m,ArH), 7.51–7.54(1H,m,ArH), 8.02–8.04 (2H,m,ArH). SI-MS m/z: 905 [M+H]$^+$

Example 34

10-O-(4-Benzyloxycarbonylpiperazinocarbonyl)-13-O-[3-(tert-butoxycarbonyl)-2-(4-methoxyphenyl)-4-phenyl-5-oxazolidinecarbonyl]-7-O-triethylsilyl-10-deacetylbaccatin III (Compound 34)

The compound (30 mg, 0.033 mmol) of Example 33 and 3-(tert-butoxycarbonyl)-2-(4-methoxyphenyl)-4-phenyl-5-oxazolidinecarboxylic acid (53 mg, 0.13 mmol) were dissolved in toluene (10 mn), followed by the addition of DCC (30 mg, 0.15 mmol) and DMAP (5 mg). The resulting mixture was stirred at room temperature for 5 hours under an argon gas atmosphere. A precipitate in the reaction mixture was filtered off, and a saturated aqueous solution of sodium hydrogencarbonate was added to the filtrate. The thus-obtained mixture was extracted with ethyl acetate. The organic layer was washed with a saturated aqueous solution of sodium chloride, dried over anhydrous sodium sulfate, and then concentrated to dryness under reduced pressure. The residue was purified by chromatography on a silica gel column (chloroform). Eluted TLC single-spot fractions were combined together and then concentrated to dryness under reduced pressure, whereby the title compound (38 mg, 90%) was obtained as a colorless oil.

$^1$H-NMR (CDCl$_3$)δ: 0.53–0.59(6H,m,Si—CH$_2$X3), 0.90 (9H,t,J=8 Hz,-MeX3), 1.04(9H,s,t-Bu), 1.16(6H,s,C16-Me and C17-Me), 1.63(3H,s,C19-Me), 1.76(6H,s,C4-OAc and C18-Me), 1.76–1.85(1H,m,C6-H), 2.10–2.16(2H,m,C14-H), 2.42–2.50(1H,m,C6-H), 3.25–3.90(8H,m), 3.71(1H,d,J=7 Hz,C3-H), 3.81(3H,s,OMe), 4.08(1H,d,J=8 Hz,C20-H), 4.22(1H,d,J=8 Hz,C20-H), 4.39(1H,dd,J=7 Hz,11 Hz,C7-H), 4.57(1H,d,J=6 Hz,C4'-H), 4.84(1H,d,J=8 Hz,C5-H), 5.16(2H,s,—CH$_2$—), 5.35(1H,br-s,C2'-H), 5.61(1H,d,J=7 Hz,C2-H), 6.10(1H,t,J=8 Hz,C13-H), 6.32(1H,s,C10-H), 6.34(1H,br-s,C5'-H), 6.91–6.93(2H,m,ArH), 7.32–7.50 (14H,m,ArH), 7.60–7.64(1H,m,ArH), 8.02–8.03(2H,m, ArH).

Example 35

10-O-(4-Benzyloxycarbonylpiperazinocarbonyl)-13-O-[3-(tert-butoxycarbonylamino)-2-hydroxy-3-phenylpropionyl]-10-O-10-deacetylbaccatin III (Compound 35)

The compound (33 mg, 0.026 mmol) of Example 34 was dissolved in ethanol (8 ml), followed by the addition of 0.1 N hydrochloric acid (1 ml, 0.1 mmol). The resulting mixture was stirred at room temperature for 3 days. A saturated aqueous solution of sodium hydrogen-carbonate was added to the reaction mixture, followed by extraction with ethyl acetate. The organic layer was washed with a saturated aqueous solution of sodium chloride, dried over anhydrous sodium sulfate, and then concentrated to dryness under reduced pressure, whereby the title compound (17 mg, 63%) was obtained as a colorless oil.

$^1$H-NMR (CDCl$_3$)δ: 1.13(3H,s,C-16 or C17-Me), 1.26 (3H,s,C-16 or C17-Me), 1.33(9H,s,t-Bu), 1.67(3H,s,C19-Me), 1.85–1.92(1H,m,C6-H), 1.87(3H,s,C18-Me), 2.25–2.40(2H,m,C14-H), 2.37(3H,s,C4-OAc), 2.50–2.58 (1H,m,C6-H), 3.00(1H,s), 3.25–3.74(8H,m), 3.79(1H,d,J=7 Hz,C3-H), 4.17(1H,d,J=8 Hz,C20-H), 4.30(1H,d,J=8 Hz,C20-H), 4.43(1H,dd,J=7,11 Hz,C7-H), 4.62(1H,s,C2'-H), 4.96(1H,d,J=8 Hz,C5-H), 5.16(2H,s,—CH$_2$—), 5.28 (1H,m), 5.35(1H,d,J=10 Hz,C3'-H), 5.66(1H,d,J=7 Hz,C2-H), 6.25(1H,t,J=8 Hz,C13-H), 6.28(1H,s,C10-H), 7.29–7.42 (10H,m,ArH), 7.47–7.52(2H,m,ArH), 7.59–7.64(1H,m, ArH), 8.09–8.13(2H,m,ArH).

Example 36

13-O-[3-(tert-Butoxycarbonylamino)-2-hydroxy-3-phenylpropionyl]-10-O-(piperazinocarbonyl)-10-O-deacetylbaccatin III (Compound 36)

The compound (17 mg, 0.016 mmol) of Example 35 was dissolved in ethanol (5 ml), followed by the addition of 10% palladium on charcoal (5 mg). The resulting mixture was stirred for 7 hours at room temperature and atmospheric pressure under a hydrogen gas atmosphere. The reaction mixture was filtered, washed with chloroform and then concentrated to dryness under reduced pressure, whereby a colorless oil (10 mg) was obtained. The oil was purified by reverse-phase high-performance column chromatography (eluent: 10 mM potassium dihydrogenphosphate-acetonitrile [1:1]). Eluted HPLC single-peak fractions were combined together, concentrated under reduced pressure, and then extracted with chloroform. The organic layer was washed with a saturated aqueous solution of sodium chloride, dried over anhydrous sodium sulfate, and then concentrated to dryness under reduced pressure, whereby the title compound (3 mg, 21%) was obtained as colorless crystals.

$^1$H-NMR (CDCl$_3$)δ: 1.14(3H,s,C16 or C17-Me), 1.26 (3H,s,C16 or C17-Me), 1.33(9H,s,t-Bu), 1.67(3H,s,C19-Me), 1.85–1.92(1H,m,C6-H), 1.88(3H,s,C18-Me), 2.22–2.35(2H,m,C14-H), 2.38(3H,s,C4-OAc), 2.49–2.58 (1H,m,C6-H), 2.80–3.05(4H,m), 3.38–3.71(4H,m), 3.80 (1H,d,J=7 Hz,C3-H), 4.17(1H,d,J=8 Hz,C20-H), 4.30(1H,d, J=8 Hz,C20-H), 4.44(1H,dd,J=7,11 Hz,C7-H), 4.63(1H,s, C2'-H), 4.96(1H,d,J=8 Hz,C5-H), 5.27(1H,m), 5.42(1H,d,J= 10 Hz,C3'-H), 5.66(1H,d,J=7 Hz,C2-H), 6.25(1H,t,J=8 Hz,C13-H), 6.27(1H,s,C10-H), 7.30–7.45(5H,m,ArH), 7.47–7.53(2H,m,ArH), 7.59–7.64(1H,m,ArH), 8.09–8.13 (2H,m,ArH). SI-MS m/z: 920 [M+H]$^+$

Example 37

10-O-(4-Methylpiperazinocarbonyl)-7-O-triethylsilyl-10-deacetylbaccatin III (Compound 37)

Using 4-methylpiperazinocarbonyl chloride (28 mg, 0.17 mmol), the title compound (83 mg, 70%) was obtained as colorless crystals by conducting reactions and post-treatment as in Example 4.

$^1$H-NMR (CDC)δ: 0.54–0.66(6H,m,Si—CH$_2$X3), 0.93 (9H,t,J=8 Hz,-MeX3), 1.05(3H,s,C-16 or C17-Me), 1.17 (3H,s,C-16 or C17-Me), 1.68(3H,s,C19-Me), 1.84–1.91(1H, m,C6-H), 2.25–2.30(2H,m,C14-H), 2.26(3H,s,C18-Me), 2.29(3H,s,C4-OAc), 2.30–2.56(4H,m), 2.35(3H,s,N-Me), 2.49–2.56(1H,m,C6-H), 3.41(1H,br-s), 3.54(1H,br-s), 3.70 (1H,br-s), 3.90(1H,br-s), 3.90(1H,d,J=7 Hz,C3-H), 4.15(1H, d,J=8 Hz,C20-H), 4.30(1H,d,J=8 Hz,C20-H), 4.49(1H,dd,J= 7,11 Hz,C7-H), 4.84(1H,m,C13-H), 4.96(1H,d,J=8 Hz,C5-H), 5.63(1H,d,J=7 Hz,C2-H), 6.39(1H,s,C10-H), 7.46–7.50 (2H,m,ArH), 7.59–7.62(1H,m,ArH), 8.11(2H,d,J=7 Hz,ArH). SI-MS m/z: 785 [M+H]$^+$

Example 38

10-O-(4-Methylpiperazinocarbonyl)-13-O-(4-phenyl-2-trichloromethyl-5-oxazolidinecarbonyl)-7-O-triethylsilyl-10-deacetylbaccatin III (Compound 38)

Using the compound (20 mg, 0.025 mmol) of Example 37, the title compound (24 mg, 90%) was obtained as a colorless oil by conducting reactions and post-treatment as in Example 5.

$^1$H-NMR (CDCl$_3$)δ: 0.54–0.61(6H,m,Si—CH$_2$X3), 0.92 (9H,t,J=8 Hz,-MeX3), 1.20(3H,s,C-16 or C17-Me), 1.21 (3H,s,C-16 or C17-Me), 1.65(3H,s,C19-Me), 1.72(1H,s), 1.78(3H,s,C18-Me), 1.77–1.84(1H,m,C6-H), 2.11(3H,s,C4-OAc), 2.11–2.14(2H,m,C14-H), 2.25–2.62(4H,m), 2.36(3H, s,N-Me), 2.48(1H,m,C6-H), 3.28(1H,t,J=6 Hz,-NH—), 3.42 (1H,br-s), 3.53(1H,br-s), 3.66(1H,br-s), 3.77(1H,d,J=7 Hz,C3-H), 3.90(1H,br-H), 4.09(1H,d,J=8 Hz,C20-H), 4.23

(1H,d,J=8 Hz,C20-H), 4.44(1H,dd,J=7,11 Hz,C7-H), 4.67–4.69(1H,m), 4.74–4.78(1H,m), 4.86(1H,d,J=8 Hz,C5-H), 5.52(1H,d,J=6 Hz), 5.65(1H,d,J=7 Hz,C2-H), 6.29(1H, t,J=8 Hz,C13-H), 6.38(1H,s,C10-H), 7.39–7.42(3H,m,ArH), 7.50–7.57(4H,m,ArH), 7.63–7.67(1H,m,ArH), 8.04(2H,d, J=7 Hz,ArH).

Example 39

13-O-[3-(tert-Butoxycarbonylamino)-2-hydroxy-3-phenylpropionyl]-10-O-(4-methylpiperazinocarbonyl)-10-deacetylbaccatin III (compound 39)

Using the compound (20 mg, 0.019 mmol) of Example 38, the title compound (5 mg, 23%) was obtained as colorless crystals by conducting reactions and post-treatment as in Example 6.

$^1$H-NMR (CDCl$_3$)δ: 1.14(3H,s,C-16 or C17-Me), 1.27 (3H,s,C-16 or C17-Me), 1.33(9H,s,t-Bu), A—1.67(3H,s, C19-Me), 1.85–1.92(1H,m,C6-H), 1.87(3H,s,C18-Me), 2.23–2.36(2H,m,C14-H), 2.38(3H,s,C4-OAc), 2.40(3H,br-s,N—CH$_3$), 2.50–2.59(5H,m), 3.11(1H,br-s), 3.47–3.79(4H, m), 3.80(1H,d,J=7 Hz,C3-H), 4.17(1H,d,J=9 Hz,C20-H), 4.30(1H,d,J=9 Hz,C20-H), 4.44(1H,dd,J=7,11 Hz,C7-H), 4.63(1H,br-s,C2'-H), 4.97(1H,d,J=8 Hz,C5-H), 5.27(1H,s), 5.36(1H,d,J=10 Hz,C3'-H), 5.66(1H,d,J=7 Hz,C2-H), 6.26 (1H,t,J=8 Hz,C13-H), 6.27(1H,s,C10-H), 7.32–7.43(5H,m, ArH), 7.48–7.52(2H,m,ArH), 7.60–7.63(1H,m,ArH), 8.11 (2H,d,J=7 Hz,ArH). SI-MS m/z: 934 [M+H]$^+$

Example 40

10-O-(4-Ethylpiperazinocarbonyl)-7-O-triethylsilyl-10-deacetylbaccatin III (Compound 40)

Using 4-ethylpiperazinocarbonyl chloride (30 mg, 0.17 mmol), the title compound (80 mg, 66%) was obtained as colorless crystals by conducting reactions and post-treatment as in Example 4.

$^1$H-NMR (CDCl$_3$)δ: 0.54–0.64(6H,m,Si—CH$_2$x3), 0.93 (9H,t,J=8 Hz,-MeX3), 1.04(3H,s,C16 or C17-Me), 1.11(3H, t,J=7 Hz,ethyl-Me), 1.17(3H,s,C16 or C17-Me), 1.68(3H,s, C19-Me), 1.84–1.90(1H,m,C6-H), 2.21–2.34(4H,m), 2.25 (3H,s,C18-Me), 2.28(3H,s,C4-OAc), 2.45(2H,q,J=7 Hz,N—CH$_2$), 2.50–2.60(3H,m), 3.38(1H,br-s), 3.51(1H,br-s), 3.68(1H,br-s), 3.90(1H,br-s), 3.90(1H,d,J=7 Hz,C3-H), 4.15(1H,d,J=8 Hz,C20-H), 4.30(1H,d,J=8 Hz,C20-H), 4.49 (1H,dd,J=7,11 Hz,C7-H), 4.83(1H,m,C13-H), 4.96(1H,d, J=9 Hz,C5-H), 5.63(1H,d,J=7 Hz,C2-H), 6.39(1H,s,C10-H), 7.45–7.49(2H,m,ArH), 7.58–7.62(1H,m,ArH), 8.11(2H,d, J=7 Hz,ArH). SI-MS m/z: 799 [M+H]$^+$

Example 41

10-O-(4-Ethylpiperazinocarbonyl)-13-O-(4-phenyl-2-trichloromethyl-5-oxazolidinecarbonyl)-7-O-triethylsilyl-10-deacetylbaccatin III (Compound 41)

Using the compound (20 mg, 0.025 mmol) of Example 40, the title compound (25 mg, 91%) was obtained as colorless crystals by conducting reactions and post-treatment as in Example 5.

$^1$H-NMR (CDCl$_3$)δ: 0.54–0.61(6H,m,Si—CH$_2$X3), 0.92 (9H,t,J=8 Hz,-MeX3), 1.11(3H,t,J=7 Hz,ethyl-Me), 1.20 (3H,s,C16 or C17-Me), 1.21(3H,s,C16 or C17-Me), 1.65 (3H,s,C19-Me), 1.78(3H,s,C18-Me), 1.80–1.88(1H,m,C6-H), 2.12(3H,s,C4-OAc), 2.14(2H,m), 2.25–2.60(5H,m), 2.45(2H,q,J=7 Hz,N—CH$_2$), 3.27(1H,t,J=6 Hz,-NH—), 3.40(1H,br-s), 3.50(1H,br-s), 3.66(1H,br-s), 3.77(1H,d,J=7 Hz,C3-H), 3.87(1H,br-s), 4.09(1H,d,J=8 Hz,C20-H), 4.23 (1H,d,J=8 Hz,C20-H), 4.44(1H,dd,J=7,10 Hz,C7-H), 4.67–4.69(1H,m), 4.74–4.78(1H,m), 4.87(1H,d,J=8 Hz,C5-H), 5.52(1H,d,J=6 Hz), 5.65(1H,d,J=7 Hz,C2-H), 6.29(1H, t,J=11 Hz,C13-H), 6.38(1H,s,C10-H), 7.35–7.45(3H,m, ArH), 7.49–7.57(4H,m,ArH), 7.63–7.65(1H,m,ArH), 8.04 (2H,d,J=7 Hz,ArH).

Example 42

13-O-[3-(tert-Butoxycarbonylamino)-2-hydroxy-3-phenylpropionyl]-10-O-(4-ethylpiperazinocarbonyl)-10-deacetylbaccatin III (Compound 42)

Using the compound (20 mg, 0.019 mmol) of Example 41, the title compound (5 mg, 30%) was obtained as colorless crystals by conducting reactions and post-treatment as in Example 6.

$^1$H-NMR (CDCl$_3$)δ: 1.11(3H,t,J=7 Hz,ethyl-Me), 1.14 (3H,s,C16 or C17-Me), 1.26(3H,s,C16 or C17-Me), 1.33 (9H,s,t-Bu), 1.67(3H,s,C19-Me), 1.85–1.91(1H,m,C6-H), 1.87(3H,s,C18-Me), 2.22–2.35(2H,m,C14-H), 2.37(3H,s, C4-OAc), 3.17(1H,br-s), 2.50–2.57(7H,m), 3.47–3.79(4H, m), 3.80(1H,d,J=7 Hz,C3-H), 4.17(1H,d,J=8 Hz,C20-H), 4.30(1H,d,J=8 Hz,C20-H), 4.44(1H,dd,J=7,11 Hz,C7-H), 4.63(1H,br-s,C2'-H), 4.96(1H,d,J=8 Hz,C5-H), 5.27(1H,s), 5.36(1H,d,J=9 Hz,C3'-H), 5.66(1H,d,J=7 Hz,C2-H), 6.25 (1H,t,J=8 Hz,C13-H), 6.26(1H,s,C10-H), 7.32–7.42(5H,m, ArH), 7.48–7.52(2H,m,ArH), 7.60–7.63(1H,m,ArH), 8.11 (2H,d,J=7 Hz,ArH). SI-MS m/z: 948[M+H]$^+$

Example 43

10-O-[4-(Isopropylaminocarbonylmethyl) piperazinocarbonyl]-7-O-triethylsilyl-10-deacetylbaccatin III (Compound 43)

Using 4-(isopropylaminocarbonylmethyl) piperazinocarbonyl chloride (42 mg, 0.17 mmol), the title compound (83 mg, 70%) was obtained as colorless crystals by conducting reactions and post-treatment as in Example 4.

$^1$H-NMR (CDCl$_3$)δ: 0.59(6H,dq,J=3 Hz,8 Hz,Si—CH$_2$X3), 0.93(9H,t,J=8 Hz,-MeX3), 1.05(3H,s,C16 or C17-Me), 1.17(6H,s,C16 or C17-H,isopropyl-Me), 1.19(3H,s, isopropyl-Me), 1.68(3H,s,C19-Me), 1.84–1.90(1H,m,C6-H), 2.25(3H,s,C18-Me), 2.29(3H,s,C4-OAc), 2.29(2H,m, C14-H), 2.43–2.60(5H,m), 3.00(2H,d,J=3 Hz), 3.45(1H,m), 3.59(2H,m), 3.87(1H,m), 3.89(1H,d,J=7 Hz,C3-H), 4.08–4.15(1H,m,isopropyl-CH), 4.15(1H,d,J=8 Hz,C20-H), 4.30(1H,d,J=8 Hz,C20-H), 4.49(1H,dd,J=7,11 Hz,C7-H), 4.84(1H,m,C13-H), 4.96(1H,d,J=9 Hz,C5-H), 5.63(1H,d, J=7 Hz,C2-H), 6.39(1H,s,C10-H), 6.88(1H,d,J=9 Hz), 7.46–7.50(2H,m,ArH), 7.59–7.62(1H,m,ArH), 8.11(2H,d, J=7 Hz,ArH). SI-MS m/z: 870 [M+H]$^+$

Example 44

10-O-[4-(Isopropylaminocarbonylmethyl) piperazinocarbonyl]-13-O-(4-phenyl-2-trichloromethyl-5-oxazolidinecarbonyl)-7-O-triethylsilyl-10-deacetylbaccatin III (Compound 44)

Using the compound (22 mg, 0.025 mmol) of Example 43, the title compound (28 mg, 97%) was obtained as colorless crystals by conducting reactions and post-treatment as in Example 5.

$^1$H-NMR (CDCl$_3$)δ: 0.59(6H,m,Si—CH$_2$X3), 0.92(9H,t, J=8 Hz,-MeX3), 1.17(3H,s), 1.19(6H,s), 1.21(3H,s), 1.65 (3H,s,C19-Me), 1.76(3H,s,C18-Me), 1.79–1.88(1H,m,C6-H), 2.10(3H,s,C4-OAc), 2.13(2H,m,C14-H), 2.45–2.52(1H, m,C6-H), 2.56(4H,br-s), 3.01(2H,d,J=3 Hz), 3.31(1H,t,J=6 Hz,-NH—), 3.45(1H,br-s), 3.59(2H,br-s), 3.76(1H,d,J=7 Hz,C3-H), 3.83(1H,br-H), 4.09(1H,d,J=8 Hz,C20-H), 4.07–4.13(1H,m,isopropyl-CH), 4.23(1H,d,J=8 Hz,C20-H), 4.44(1H,dd,J=7,11 Hz,C7-H), 4.67–4.69(1H,m), 4.74–4.77 (1H,m), 4.86(1H,d,J=8 Hz,C5-H), 5.52(1H,d,J=6 Hz), 5.65 (1H,d,J=7 Hz,C2-H), 6.29(1H,t,J=8 Hz,C13-H), 6.38(1H,s, C10-H), 6.87-6.89(1H,d,J=8 Hz), 7.37–7.42(3H,m,ArH), 7.50-7.57(4H,m,ArH), 7.64–7.67(1H,m,ArH), 8.04(2H,d, J=7 Hz,ArH).

Example 45

13-O-[3-(tert-Butoxycarbonylamino)-2-hydroxy-3-phenylpropionyl]-10-O-[4-(isopropylaminocarbonylmethyl)piperazinocarbonyl]-10-deacetylbaccatin III (Compound 45)

Using the compound (22 mg, 0.019 mmol) of Example 44, the title compound (3 mg, 15%) was obtained as colorless crystals by conducting reactions and post-treatment as in Example 6.

$^1$H-NMR (CDCl$_3$)δ: 1.14(3H,s,C16 or C17-Me), 1.18 (3H,s,isopropyl-Me), 1.20(3H,s,isopropyl-Me), 1.26(3H,s, C16 or C17-Me), 1.33(9H,s,t-Bu), 1.67(3H,s,C19-Me), 1.85–1.91(1H,m,C6-H), 1.88(3H,s,C18-Me), 2.30(2H,m, C14-H), 2.38(3H,s,C4-OAc), 2.45–2.75(5H,m), 3.06(3H,s), 3.47–3.70(4H,m), 3.79(1H,d,J=7 Hz,C3-H), 4.11(1H,m, isopropyl-CH), 4.17(1H,d,J=8 Hz,C20-H), 4.30(1H,d,J=8 Hz,C20-H), 4.44(1H,dd,J=7,11 Hz,C7-H), 4.63(1H,br-s, C2'-H), 4.96(1H,d,J=8 Hz,C5-H), 5.27(1H,m), 5.37(1H,d, J=9 Hz,C3'-H), 5.66(1H,d,J=7 Hz,C2-H), 6.25(1H,t,J=8 Hz,C13-H), 6.27(1H,s,C10-H), 6.88(1H,br-s), 7.26–7.41 (5H,m,ArH), 7.48–7.52(2H,m,ArH), 7.60–7.62(1H,m,ArH), 8.11(2H,d,J=7 Hz,ArH). SI-MS m/z: 1019 [M+H]$^+$ Example 46

10-O-[3-{4-(Isopropylaminocarbonylmethyl) piperazinocarbonyl}propionyl]-7-O-triethylsilyl-10-deacetylbaccatin III (Compound 46)

1) From 3-[4-(isopropylaminocarbonylmethyl) piperazinocarbonyl]propionic acid (0.33 g, 1.2 mmol), DCC (309 mg, 1.5 mmol) and 4-nitrothiophenol (0.23 g, 1.5 mmol), S-4-nitrophenyl 3-[4-(isopropylaminocarbonylmethyl)piperazinocarbonyl] propanethioate (0.41 g, 81%) was obtained by conducting a reaction and post-treatment as in Example 17, 1).

$^1$H-NMR (CDCl$_3$)δ: 1.15(6H,d,J=7 Hz), 2.49(4H,m), 2.70(2H,t,J=6 Hz), 2.97(2H,s), 3.06(2H,t,J=7 Hz), 3.48(2H, t,J=5 Hz), 3.62(2H,t,J=5 Hz), 4.08(1H,m), 6.74(1H,s), 7.60 (2H,d,J=9 Hz), 8.21(2H,d,J=9 Hz).

2) From 7-O-triethylsilyl-10-deacetylbaccatin III (66 mg, 0.16 mmol), a solution of n-butyllithium (0.14 mol) in hexane and the above-described thioester (59 mg, 0.14 mmol), the title compound (89 mg, 97%) was obtained by conducting reactions and post-treatment as in Example 17, 2).

$^1$H-NMR (CDCl$_3$)δ: 0.58(6H,m), 0.92(9H,t,J=8 Hz), 1.04 (3H,s), 1.17(3H,s), 1.18(6H,d,J=7 Hz), 1.68(3H,s), 1.87(1H, m), 2.18(3H,s), 2.29(3H,s), 2.50–2.95(9H,m), 3.00(2H,s), 3.61(4H,m), 3.80(1H,d,J=7 Hz,C3-H), 4.11(1H,m), 4.14 (1H,d,J=9 Hz,C20-H), 4.30(1H,d,J=8 Hz,C20-H), 4.48(1H, dd,J=10,7 Hz,C7-H), 4.85(1H,s,C13-H), 4.90(1H,d,J=8 Hz,C5-H), 5.63(1H,d,J=7 Hz,C2-H), 6.45(1H,s,C10-H), 6.81(1H,s), 7.48(2H,t,J=8 Hz), 7.60(1H,t,J=7 Hz), 8.11(2H, d,J=7 Hz).

Example 47

13-O-(3-Benzyloxycarbonyl-2,2-dimethyl-4-phenyl-5-oxazolidinecarbonyl)-10-O-[3-{4-(isopropylaminocarbonylmethyl)piperazinocarbonyl}-propionyl]-7-O-triethylsilyl-10-deacetylbaccatin III (Compound 47)

The compound (85 mg, 0.09 mmol) of Example 46 was dissolved in toluene, followed by the addition of 3-benzyloxycarbonyl-2,2-dimethyl-4-phenyl-5-oxazolidinecarboxylic acid (164 mg, 0.47 mmol), DCC (97 mg, 0.47 mmol) and DMAP (5 mg). The resulting mixture was stirred at room temperature for 2 days. Post-treatment was conducted as in Example 18. Purification was conducted by chromatography on a silica gel column (chloroform-methanol mixed solvent [97:3]), whereby the title compound (113 mg, 99%) was obtained.

$^1$H-NMR (CDCl$_3$)δ: 0.55(6H,m), 0.91(9H,t,J=8 Hz), 1.18 (6H,d,J=7 Hz), 1.19(3H,s), 1.26(3H,s), 1.65(3H,s), 1.77(3H, s), 1.82(3H,s), 1.90(3H,s), 2.04(3H,s), 2.18(3H,s), 1.60–2.20(4H,m), 2.69(4H,m), 2.70(2H,m), 2.82(2H,m), 3.00(2H,s), 3.60(4H,m), 3.78(1H,d,J=7 Hz,C3-H), 4.09(1H, m), 4.10(1H,d,J=8 Hz,C20-H), 4.24(1H,d,J=8 Hz,C20-H), 4.44(1H,dd,J=10,7 Hz,C7-H), 4.51(1H,d,J=6 Hz), 4.55(1H, s), 4.87(1H,d,J=9 Hz,C5-H) 4.80–5.10(2H,br), 5.55(1H,s), 5.64(1H,d,J=7 Hz,C2-H), 6.22(1H,t,J=8 Hz,C13-H), 6.42 (1H,s,C10-H), 6.76(1H,br), 6.85(1H,br), 7.21–7.46(9H,m), 7.48(2H,t,J=7 Hz), 7.62(1H,t,J=7 Hz), 8.04(2H,d,J=7 Hz).

Example 48

13-O-[3-(tert-Butoxycarbonylamino)-2-hydroxy-3-phenylpropionyl]-10-O-[3-{4-(isopropylaminocarbonylmethyl) piperazinocarbonyl}propionyl]-10-deacetylbaccatin III (Compound 48)

The compound (85 mg, 0.067 mmol) of Example 47 was dissolved in ethanol (8 ml), followed by the addition of 0.1 N hydrochloric acid (8 ml). The resulting mixture was stirred at room temperature for 23 hours. The solvent was distilled off under reduced pressure, and chloroform was added to the residue. The thus-obtained mixture was washed with a saturated aqueous solution of sodium hydrogencarbonate. The organic layer was dried over anhydrous magnesium sulfate, the solvent was distilled off under reduced pressure, and methanol (5 ml), water (0.5 ml) and 10% palladium on charcoal (18 mg) were added to the residue. The thus-obtained mixture was stirred for 2 hours at room temperature and atmospheric pressure under a hydrogen gas atmosphere. The resulting mixture was filtered through a glass filter with Celite distributed thereon. After the filtrate was concentrated, methylene chloride (10 ml) was added to the residue so that the residue was dissolved. S-tert-Butoxycarbonyl-4,6-dimethyl-2-mercaptopyrimidine (19 mg, 0.08 mmol) and triethylamine (8 mg, 0.08 mmol) were added, followed by stirring at room temperature for 23 hours and further at 40° C. for 6 days. Post-treatment was conducted as in Example 19. Preliminary purification was conducted by chromatography on a silica gel column (chloroform-methanol mixed solvent [97:3]). Further purification was conducted by reverse-phase high-performance column chromatography (eluent: 10 mM potassium dihydrogen-phosphate-acetonitrile [1:1]), whereby the title compound (24 mg, 33%) was obtained.

$^1$H-NMR (CDCl$_3$)δ: 1.12(3H,s), 1.20(6H,br), 1.24(3H,s), 1.31(9H,s), 1.65(3H,s), 1.83(3H,s), 2.35(3H,s), 2.23–3.20 (10H,br), 3.24–3.75(5H,br), 3.79(1H,d,J=7 Hz,C3-H), 4.10 (1H,m), 4.14(1H,d,J=9 Hz,C20-H), 4.28(1H,d,J=9 Hz,C20-H), 4.36(1H,br,C7-H), 4.69(1H,s,C2'-H), 4.93(1H,d,J=8 Hz,C5-H), 5.24(1H,br), 5.35(1H,d,J=10 Hz,C3'-H), 5.65 (1H,d,J=7 Hz,C2-H), 6.21(1H,br,C13-H), 6.28(1H,s,C10-H), 6.79(1H,s), 7.35(5H,m), 7.48(2H,t,J=8 Hz), 7.59(1H,t, J=7 Hz), 8.09(2H,d,J=7 Hz). SI-MS m/z: 1075 [M+H]$^+$

Example 49

10-O-[{4-(Isopropylaminocarbonylmethyl) piperazinocarbonyloxy}acetyl]-7-O-triethylsilyl-10-deacetylbaccatin III (Compound 49)

1) From [4-(isopropylaminocarbonylmethyl) piperazinocarbonyloxy]acetic acid (170 mg, 0.6 mmol), DCC (0.17 g, 0.8 mmol) and 4-nitrothiophenol (0.17 g, 0.8 mmol), S-4-nitrophenyl [4-(isopropylaminocarbonylmethyl)piperazinocarbonyloxy] thioacetate (187 mg, 73%) was obtained by conducting reactions and post-treatment as in Example 17, 1).

$^1$H-NMR (CDCl$_3$)δ: 1.17(6H,d,J=7 Hz), 2.57(4H,t,J=5 Hz), 3.02(2H,s), 3.63(4H,d,J=16 Hz), 4.11(1H,m), 4.96(2H, s), 6.80(1H,s), 7.61(2H,d,J=9 Hz), 8.27(2H,d,J=9 Hz).

2) From 7-O-triethylsilyl-10-deacetylbaccatin III (135 mg, 0.2 mmol), a solution of n-butyllithium (0.24 mol) in hexane and the above-described thioester (134 mg, 0.32 mmol), the title compound (0.16 g, 100%) was obtained by conducting reactions and post-treatment as in Example 17, 2).

$^1$H-NMR (CDCl$_3$)δ: 0.59(6H,m), 0.92(9H,t,J=8 Hz), 1.04 (3H,s), 1.16(3H,s), 1.18(6H,d,J=7 Hz), 1.68(3H,s), 1.91(1H, m), 2.10(1H,m), 2.17(3H,s), 2.28(3H,s), 2.51(5H,m), 3.00 (2H,s), 3.59(4H,m), 3.86(1H,d,J=7 Hz,C3-H), 4.10(1H,m), 4.14(1H,d,J=9 Hz,C20-H), 4.30(1H,d,J=8 Hz,C20-H), 4.49 (1H,dd,J=10,7 Hz,C7-H), 4.76(2H,m), 4.83(1H,s,C13-H), 4.95(1H,d,J=9 Hz,C5-H), 5.62(1H,d,J=7 Hz,C2-H), 6.48 (1H,s,C10-H), 6.83(1H,s), 7.48(2H,t,J=8 Hz), 7.61(1H,t,J=7 Hz), 8.10(2H,d,J=7 Hz).

Example 50

13-O-(3-Bnzyloxycarbonyl-2,2-dimethyl-4-phenyl-5-oxazolidinecarbonyl)-10-[{4-(isopropylaminocarbonylmethyl) piperazinocarbonyloxy}acetyl]-7-O-triethylsilyl-10-deacetylbaccatin III (Compound 50)

From the compound (155 mg, 0.17 mmol) of Example 49, 3-benzyloxycarbonyl-2,2-dimethyl-4-phenyl-5-oxazlidinecarboxylic acid (131 mg, 0.37 mmol), DCC (76 mg, 0.37 mmol) and DMAP (5 mg), the title compound (200 mg, 93%) was obtained by conducting reactions and post-treatment as in Example 18.

$^1$H-NMR (CDCl$_3$)δ: 0.56(6H,q,J=8 Hz), 0.91(9H,t,J=7 Hz), 1.19(12H,s), 1.69(3H,s), 1.77(3H,s), 1.82(3H,s), 1.91 (3H,s), 2.06(3H,s), 1.60–2.20(4H,m), 1.55–2.10(4H,m), 2.16(2H,d,J=9 Hz), 2.52(4H,m,br), 3.00(2H,s), 3.59(4H,m), 3.77(1H,d,J=7 Hz,C3-H), 4.08(1H,m), 4.10(1H,d,J=9 Hz,C20-H), 4.25(1H,d,J=8 Hz,C20-H), 4.45(1H,dd,J=10,6 Hz,C7-H), 4.51(1H,d,J=6 Hz), 4.87(1H,d,J=8 Hz,C5-H), 4.75–4.97(4H,m,br), 5.25(1H,s), 5.64(1H,d,J=7 Hz,C2-H), 6.22(1H,t,J=9 Hz,C13-H), 6.45(1H,s,C10-H), 6.77(1H,br), 6.80(1H,br), 7.23–7.47(9H,m), 7.50(2H,t,J=7 Hz), 7.63(1H, t,J=7 Hz), 8.03(2H,d,J=7 Hz).

Example 51

13-O-[3-(tert-Butoxycarbonylamino)-2-hydroxy-3-phenylpropionyl]-10-O-[{4-(isopropylaminocarbonylmethyl) piperazinocarbonyloxy}acetyl]-10-deacetylbaccatin III (Compound 51)

The compound (72 mg, 0.057 mmol) of Example 50 was dissolved in ethanol (6 ml), followed by the addition of 0.1 N hydrochloric acid (6 ml). The resulting mixture was stirred at room temperature for 9 hours. The solvent was distilled off under reduced pressure, and chloroform was added to the residue. The thus-obtained mixture was washed with a saturated aqueous solution of sodium hydrogencarbonate. The organic layer was dried over anhydrous magnesium sulfate, the solvent was distilled off under reduced pressure, and methanol (10 ml), water (1 ml) and 10% palladium on charcoal (30 mg) were then added to the residue. The thus-obtained mixture was stirred for 6 hours at room temperature and atmospheric pressure under a hydrogen gas atmosphere. The reaction mixture was filtered through a glass filter with Celite distributed thereon. After the filtrate was concentrated, methylene chloride (10 ml) was added to the residue so that the residue was dissolved. S-tert-Butoxycarbonyl-4,6-dimethyl-2-mercaptopyrimidine (15 mg, 0.06 mmol) and triethylamine (6 mg, 0.06 mmol) were added, followed by stirring at room temperature for 2 days. Post-treatments were conducted as in Example 19, whereby the title compound (11 mg, 18%) was obtained.

$^1$H-NMR (CDCl$_3$)δ: 1.19(3H,s), 1.22(6H,br), 1.26(3H,s), 1.34(9H,s), 1.69(3H,s), 1.87(3H,s), 2.37(3H,s), 2.26–2.55 (5H,m), 2.99(2H,s), 3.30–3.75(5H,br), 3.79(1H,d,J=7 Hz,C3-H), 4.16(1H,d,J=9 Hz,C20-H), 4.09(1H,m), 4.30(1H, d,J=8 Hz,C20-H), 4.38(1H,br,C7-H), 4.62(1H,s,C2-H), 4.69–4.90(2H,br), 4.94(1H,d,J=8 Hz,C5-H), 5.26(1H,s), 5.35(1H,d,J=10 Hz,C3'-H), 5.67(1H,d,J=7 Hz,C2-H), 6.22 (1H,t,J=9 Hz,C13-H), 6.37(1H,s,C10-H), 6.82(1H,br), 7.38 (5H,m), 7.50(2H,t,J=8 Hz), 7.61(1H,t,J=7 Hz), 8.11(2H,d, J=7 Hz). SI-MS m/z: 1077 [M+H]$^+$

The compounds obtained above in Examples 1–51 are shown in the following Tables 1–7.

TABLE 1

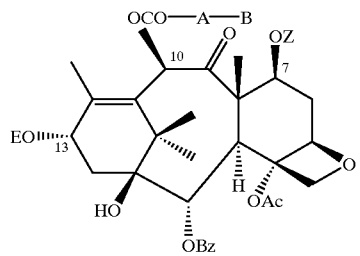

| Comp'd No. | B—A— | E | Z |
|---|---|---|---|
| 1 | H$_3$C\N-⟨piperidine⟩-N— / H$_3$C | H | TES |

TABLE 1-continued

| Comp'd No. | B—A— | E | Z |
|---|---|---|---|
| 2 | 4-(dimethylamino)-1-methylpiperidinyl | (4S,5R)-3-Cbz-2,2-dimethyl-4-phenyl-5-acetyloxazolidine | TES |
| 4 | 4-(dimethylamino)-1-methylpiperidinyl | H | TES |
| 5 | 4-(dimethylamino)-1-methylpiperidinyl | 4-phenyl-2-trichloromethyl-5-acetyloxazolidine | TES |
| 7 | 1'-methyl-[1,4']bipiperidinyl | H | TES |
| 8 | 1'-methyl-[1,4']bipiperidinyl | 4-phenyl-2-trichloromethyl-5-acetyloxazolidine | TES |

TABLE 2

[Structure: taxane core with substituents OCO—A—B at position 10, OZ at position 7, EO at position 13, HO, OBz, OAc, and oxetane ring]

| Comp'd No. | B—A— | E | Z |
|---|---|---|---|
| 10 | pyrrolidin-1-yl-(1-methyl)piperidine | H | TES |
| 11 | pyrrolidin-1-yl-(1-methyl)piperidine | Ph, Cbz-N, oxazolidine with H₃C, CH₃, acetyl (4-Ph-5-acetyl-2,2-dimethyl-3-Cbz-oxazolidine) | TES |
| 13 | morpholin-4-yl-(1-methyl)piperidine | H | TES |
| 14 | morpholin-4-yl-(1-methyl)piperidine | Ph, Cbz-N, oxazolidine with H₃C, CH₃, acetyl | TES |
| 17 | piperidin-1-yl-piperidine-N-COC₂H₄— | H | TES |
| 18 | piperidin-1-yl-piperidine-N-COC₂H₄— | Ph, Cbz-N, oxazolidine with H₃C, CH₃, acetyl | TES |

TABLE 3

[Structure of taxane core with substituents: OCO—A—B at C10, OZ at C7, EO at C13, OH, OBz, OAc, and oxetane ring]

| Comp'd No. | B—A— | E | Z |
|---|---|---|---|
| 20 | piperidine-N-C₅H₉N-COC₃H₆— | H | TES |
| 21 | piperidine-N-C₅H₉N-COC₃H₆— | Ph, Cbz-N, oxazolidine with H₃C, CH₃, C(=O)— | TES |
| 23 | piperidine-N-C₅H₉N-COOCH₂— | H | TES |
| 24 | piperidine-N-C₅H₉N-COOCH₂— | Ph, Cbz-N, oxazolidine with H₃C, CH₃, C(=O)— | TES |
| 26 | piperidine-N-C₅H₉N-CONHCH₂— | H | TES |
| 27 | piperidine-N-C₅H₉N-CONHCH₂— | Ph, Cbz-N, oxazolidine with H₃C, CH₃, C(=O)— | TES |

TABLE 4

| Comp'd No. | B—A— | E | Z |
|---|---|---|---|
| 29 | piperidine-N-C₅H₉N-CONHC₂H₄— | H | TES |
| 30 | piperidine-N-C₅H₉N-CONHC₂H₄— | (4S,5R)-3-Cbz-2,2-dimethyl-4-phenyl-5-acetyl-oxazolidine | TES |
| 33 | CbzN-piperazine-N— | H | TES |
| 34 | CbzN-piperazine-N— | (4S,5R)-3-Boc-2-(4-methoxyphenyl)-4-phenyl-5-acetyl-oxazolidine | TES |
| 37 | H₃C-N-piperazine-N— | H | TES |
| 38 | H₃C-N-piperazine-N— | 2-CCl₃-4-phenyl-5-acetyl-oxazolidine (NH) | TES |

TABLE 5

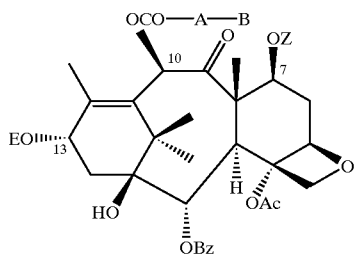

| Comp'd No. | B—A— | E | Z |
|---|---|---|---|
| 40 | H₅C₂—N(piperazine)N—methyl | H | TES |
| 41 | H₅C₂—N(piperazine)N—methyl | Ph, HN, O, CCl₃ oxazolidine with acetyl | TES |
| 43 | (H₃C)₂CHNHCOCH₂N(piperazine)N—methyl | H | TES |
| 44 | (H₃C)₂CHNHCOCH₂N(piperazine)N—methyl | Ph, HN, O, CCl₃ oxazolidine with acetyl | TES |
| 46 | (H₃C)₂CHNHCOCH₂N(piperazine)NCOC₂H₄— | H | TES |
| 47 | (H₃C)₂CHNHCOCH₂N(piperazine)NCOC₂H₄— | Ph, Cbz-N, O, H₃C, CH₃ oxazolidine with acetyl | TES |
| 49 | (H₃C)₂CHNHCOCH₂N(piperazine)NCOOCH₂— | H | TES |

TABLE 5-continued
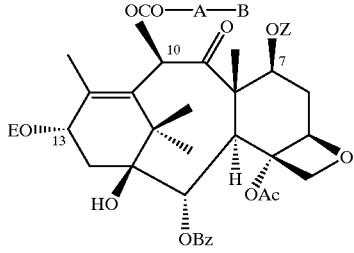
| Comp'd No. | B—A— | E | Z |
|---|---|---|---|
| 50 | 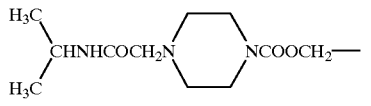 | 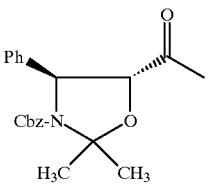 | TES |
TABLE 6
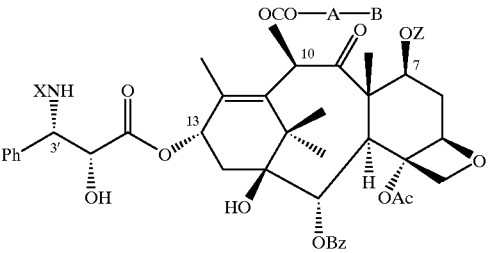
| Comp'd No. | B—A— | X | Z |
|---|---|---|---|
| 3 | 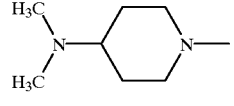 | Boc | H |
| 6 | 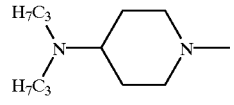 | Boc | H |
| 9 | 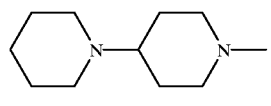 | Boc | H |
| 12 | 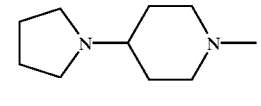 | Boc | H |
| 15 | 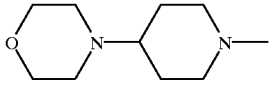 | Boc | H |
TABLE 6-continued
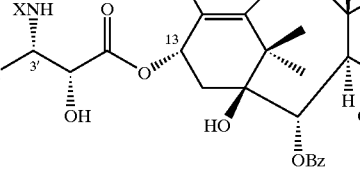
| Comp'd No. | B—A— | X | Z |
|---|---|---|---|
| 16 | 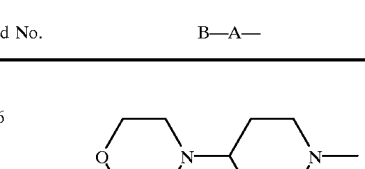 | Bz | H |
| 19 | 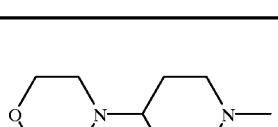 | Boc | H |
| 22 | 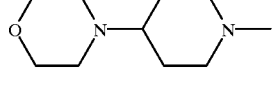 | Boc | H |
| 25 | 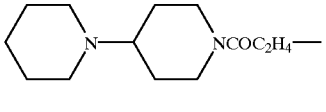 | Boc | H |

TABLE 7

[Structure: baccatin III core with substituents XNH-CH(Ph)-CH(OH)-CO-O at position 13, OCO-A-B at position 10, OZ at position 7, OH, OAc, OBz, and oxetane ring]

| Comp'd No. | B—A— | X | Z |
|---|---|---|---|
| 28 | piperidine-N—piperidine(N-COOCH₂—) | Boc | H |
| 31 | piperidine-N—piperidine(N-CONHC₂H₄—) | Boc | H |
| 32 | piperidine-N—piperidine(N-CONHC₂H₄—) | Bz | H |
| 35 | Cbz-N(piperazine)N— | Boc | H |
| 36 | HN(piperazine)N— | Boc | H |
| 39 | H₃C—N(piperazine)N— | Boc | H |
| 42 | H₅C₂—N(piperazine)N— | Boc | H |
| 45 | (H₃C)₂CH-NHCOCH₂-N(piperazine)N— | Boc | H |
| 48 | (H₃C)₂CH-NHCOCH₂-N(piperidine)(N-COC₂H₄—) | Boc | H |
| 50 | (H₃C)₂CH-NHCOCH₂-N(piperidine)(N-COOCH₂—) | Boc | H |

Referential Example 1

13-O-(3-Benzyloxycarbonyl-2,2-dimethyl-4-phenyl-5-oxazolidinecarbonyl)-7-O-triethylsilylbaccatin III (Compound 52)

To a mixture of 7-O-triethylsilylbaccatin III (1.39 g, 1.99 mmol), dimethylaminopyridine (DIIP, 122 mg, 1.00 mmol) and N-N-dicyclohexylcarbodiamide (DCC, 1.31 g, 6.37 mmol), a solution of 3-benzyloxycarbonyl-2,2-dimethyl-4-phenyl-5-oxazolidinecarboxylic acid (2.12 g, 5.96 mmol) in dry toluene (140 ml) was added. The resulting mixture was stirred at 80° C. for 2 hours under an argon gas atmosphere. An insoluble matter was filtered off by using a Celite pad, and the filtrate was concentrated to dryness under reduced pressure. The residue was purified by chromatography on a silica gel column (chloroform-n-hexane mixed solvent [1:1→2:1]), whereby the title compound (1.79 g, 87%) was obtained as colorless powder. IR (KBr): 3480, 2950, 1715, 1240 cm$^{-1}$ $^1$H-NMR (CDCl₃)δ: 0.51–0.65(6H,m,Si—CH₂X3), 0.92 (9H,t,J=8 Hz,Si—CH₂CH₃X3), 1.19(3H,s,C-16 or C-17), 1.22(3H,s,C-16 or C-17), 1.66(3H,s,C-19), 1.70(1H,s,C-1:OH), 1.78(3H,br-s,oxazolidine-CH₃), 1.83(3H,br-s, oxazoline-CH₃), 1.81–1.90(1H,m,C-6a), 1.90(3H,s,C-10:OCOCH₃), 2.05(3H,d,J=1 Hz,C-18), 2.12–2.22(2H,m,C-14), 2.18(3H,s,C-4:OCOCH₃), 2.45–2.55(1H,m,C-6b), 3.78 (1H,d,J=7 Hz,C-3), 4.10(1H,d,J=8 Hz,C-20a), 4.24(1H,d, J=8 Hz,C-20b), 4.45(1H,dd,J=7,11 Hz,C-7), 4.51(1H,d,J=6 Hz,oxazolidine-C-4 or C-5), 4.80–5.12(2H,br,Ph-CH₂O), 4.88(1H,dd,J=2,8 Hz,C-5), 5.23(1H,br-d,J=6 Hz,oxazolidine-C-4 or C-5), 5.65(1H,d,J=7 Hz,C-2), 6.22 (1H,br-t.J=9 Hz,C-13), 6.44(1H,s,C-10), 6.67–6.90(1H,br, Ph), 7.08–7.68(7H,m,Ph), 8.04(2H,dd,J=1,8 Hz,Ph(o)).

Example 52

13-O-[3-(4-dimethylaminopiperidinocarbonylamino)-2-hydroxy-3-phenylpropionyl]-7-O-triethylsilylbaccatin III (Compound 53)

The compound (100 mg, 0.096 mmol) of Referential Example 1 was dissolved in a mixed solvent consisting of methanol (10 ml) and water (1 ml), followed by the addition of 10% palladium on charcoal (50 mg). The resulting mixture was vigorously stirred at room temperature for 1.5 hours under a hydrogen gas atmosphere. After full consumption of the raw material was confirmed by thin layer chromatography, the catalyst was filtered off by using a Celite pad and the filtrate was dried with molecular sieves 3A. The molecular sieves were filtered off and the filtrate was concentrated to dryness under reduced pressure (40–50° C.), whereby 13-O-(3-amino-2-hydroxy-3-phenylpropionyl)-7-O-triethylsilylbaccatin III was obtained as colorless powder. Without purification, this crude product was provided for use in the next reaction.

$^1$H-NMR (CDCl₃)δ: 0.50–0.64(6H,m,Si—CH₂X3), 0.92 (9H,t,J=8 Hz,Si—CH₂CH₃X3), 1.18(3H,s,C-16 or C-17), 1.22(3H,s,C-16 or C-17), 1.67(3H,s,C-19), 1.81–1.93(1H, m,C-6a), 2.02(3H,s,C-18), 2–2.18(3H,s,C-10:OCOCH₃), 2.25(3H,s,C-4:OCOCH₃), 2.45–2.58(1H,m,C-6b), 3.77(1H, d,J=7 Hz,C-3), 4.13(1H,d,J=8 Hz,C-20a), 4.27(1H,d,J=8 Hz,C-20b), 4.32(2H,m,C-21 and C-31), 4.44(1H,dd,J=7,11 Hz,C-7), 4.91(1H,d,J=8 Hz,C-5), 5.64(1H,d,J=7 Hz,C-2), 6.12(1H,br-t,J=10 Hz,C-13), 6.44(1H,s,C-10), 7.22–7.68 (8H,m,C-3'-Ph and C-2-Bz(m,p)), 8.06(2H,dd,J=2,9 Hz,C-2-Bz(o)).

The compound which had been obtained in the above-described reaction was dissolved in dry pyridine (10 ml), to which 4-dimethylaminopiperidinocarbonyl chloride (22 mg, 0.12 mmol) was added. The resulting mixture was stirred at room temperature for 20–24 hours. The solvent was distilled off at low temperature (ca. 30° C.) under reduced pressure, and the residue was dissolved in chloroform. The thus-obtained mixture was washed with a 7% aqueous solution of sodium hydrogencarbonate and then with a saturated aqueous solution of sodium chloride. The chloroform layer was dried over sodium sulfate and then concentrated to dryness under reduced pressure. The residue was purified by chromatography on a silica gel column (chloroform-methanol mixed solvent [9:1]), whereby the title compound (14 mg, 14%) was obtained as pale yellow powder.

$^1$H-NMR (CDCl$_3$)δ: 0.50–0.66(6H,m,Si—CH$_2$X3)1 0.93 (9H,t,J=8 Hz,Si—CH$_2$ CH$_3$X3), 1.10–1.35(2H,m), 1.24(3H, s,C-16 or C-17), 1.25(3H,s,C-16 or C-17), 1.65–1.75(1H, br), 1.71(3H,s,C-19), 1.81–2.21(4H,m), 1.98(3H,d,J=1 Hz,C-18), 2.10(6H,br-s,-N(CH$_3$)$_2$), 2.18(3H,s,C-10:OCOCH$_3$), 2.27–2.58(4H,m), 2.52(3H,s,C-4:OCOCH$_3$), 2.85(1H,br-t,J=13 Hz), 3.74(1H,br-d,J=13 Hz), 3.80(1H,d, J=7 Hz,C-3), 3.99(1H,br-d,J=13 Hz), 4.26(1H,d,J=9 Hz,C-20a), 4.31(1H,d,J=9 Hz,C-20b), 4.47(1H,dd,J=7,11 Hz,C-7), 4.76(1H,d,J=3 Hz,C-2'), 4.92(1H,dd,J=2,10Hz,C-5), 5.49(1H,br-d,J=9 Hz,CONH), 5.56(1H,dd,J=3,9 Hz,C-31), 5.69(1H,d,J=7 Hz,C-2), 6.39(1H,br-t,J=9 Hz,C-13), 6.42 (1H,s,C-10), 7.27–7.60(8H,m,C-3'-Ph and C-2-Bz(m,p)), 8.15(2H,dd,J=2,9 Hz,C-2-Bz(o)).

Example 53

13-O-[3-(4-Dimethylaminopiperidinocarbonylamino)-2-hydroxy-3-phenylpropionyl]baccatin III (Compound 54)

The compound (14 mg, 0.014 mmol) of Example 52 was dissolved in ethanol (1.4 ml), followed by the addition of 0.1 N hydrochloric acid (1.4 ml) at 0° C. under stirring. The resulting mixture was stirred for 4 days. Chloroform and a 7% aqueous solution of sodium hydrogencarbonate were added to the reaction mixture, and the thus-obtained mixture was allowed to separate into layers. The chloroform layer was collected, washed with a saturated aqueous solution of sodium chloride, dried over anhydrous sodium sulfate, and then concentrated to dryness under reduced pressure, whereby a crude product was obtained. The crude product was purified by reverse-phase high-performance liquid column chromatography (eluent: 10 mM potassium dihydrogenphosphate-acetonitrile mixed solvent [7:4], detection: 225 nm), and fractions of the target compound were combined together. Chloroform and a 7% aqueous solution of sodium hydrogencarbonate were added to the thus-combined fractions, and the resulting mixture was allowed to separate into layers. The chloroform layer was collected, washed with a saturated aqueous solution of sodium chloride, dried over anhydrous sodium sulfate, and then concentrated to dryness under reduced pressure, whereby the title compound (5 mg, 42%) was obtained as a colorless solid.

$^1$H-NMR (CDCl$_3$)δ: 1.10–1.35(2H,m), 1.24(3H,s,C-16 or C-17), 1.25(3H,s,C-16 or C-17), 1.50–1.72(1H,br), 1.69(3H, s,C-19), 1.79–2.60(8H,m), 1.86(3H,d,J=1 Hz,C-18), 2.24 (9H,s,-N(CH$_3$)$_2$ and C-10:OCOCH$_3$), 2.50(3H,s,C-4:OCOCH$_3$), 2.84(1H,br-t,J=13 Hz), 3.78(1H,d,J=7 Hz,C-3), 3.82(1H,br-d,J=13 Hz), 4.04(1H,br-d,J=13 Hz), 4.25(1H, d,J=9 Hz,C-20a), 4.31(1H,d,J=9 Hz,C-20b), 4.42(1H,dd,J=7,11 Hz,C-7), 4.74(1H,d,J=3 Hz,C-21), 4.95(1H,dd,J=2,10 Hz,C-5), 5.53(1H,dd,J=3,9 Hz,C-3'), 5.58–5.72(1H,br, CONH), 5.68(1H,d,J=7 Hz,C-2), 6.27(1H,s,C-10), 6.39(1H, br-t,J=9 Hz,C-13), 7.27–7.62(8H,m,C-3'-Ph and C-2-Bz(m, p)), 8.15(2H,dd,J=2,9 Hz,C-2-Bz(o)). SI-MS m/z: 904 [M+H]$^+$ Example 54

13-O-[3-(4-Dipropylaminopiperidinocarbonylamino)-2-hydroxy-3-phenylpropionyl]-7-O-triethylsilylbaccatin III (Compound 55)

Using 4-dipropylaminopiperidinocarbonyl chloride (29 mg, 0.12 mmol), the title compound (17 mg, 17%) was obtained as a colorless solid by conducting a reaction and post-treatment as in Example 52.

$^1$H-NMR (CDCl$_3$)δ: 0.50–0.64(6H,m,Si—CH$_2$X3), 0.81 (6H,t,J=7 Hz,—NCH$_2$CH$_2$CH$_3$X2), 0.92(9H,t,J=8 Hz,Si—CH$_2$CH$_3$X3), 1.13–1.50(7H,m), 1.19(3H,s,C-16 or C-17), 1.23(3H,s,C-16 or C-17), 1.65–1.78(1H,br), 1.69(3H,s,C-19), 1.83–1.97(1H,m), 1.93(3H,d,J=1 Hz,C-18), 2.13–2.82 (9H,m), 2.18(3H,s,C-10:OCOCH$_3$), 2.42(3H,s,C-4:OCOCH$_3$), 3.79(1H,d,J=7 Hz,C-3), 3.86(1H,br-d,J=13 Hz), 3.97(1H,br-d,J=13 Hz), 4.19(1H,d,J=8 Hz,C-20a), 4.29 (1H,d,J=8 Hz,C-20b), 4.45(1H,dd,J=7,11 Hz,C-7), 4.70(1H, d,J=3 Hz,C-2'), 4.91(1H,dd,J=2,10 Hz,C-5), 5.37(1H,br-d, J=9 Hz,CONH), 5.48(1H,dd,J=3,9 Hz,C-3'), 5.68(1H,d,J=7 Hz,C-2), 6.22(1H,br-t,J=9 Hz,C-13), 6.42(1H,s,C-10), 7.27–7.63(8H,m,C-3'-Ph and C-2-Bz(m,p)), 8.12(2H,dd,J= 2,9 Hz,C-2-Bz(o)).

Example 55

13-O-[3-(4-Dipropylaminopiperidinocarbonylamino)-2-hydroxy-3-phenylpropionyl]baccatin III (Compound 56)

The compound (17 mg, 0.016 mmol) of Example 54 was dissolved in ethanol (1.7 ml), followed by the addition of 0.1 N hydrochloric acid (1.7 ml) at 0° C. under stirring. The resulting mixture was stirred for 3 days. The title compound (10 mg, 63%) was obtained as a colorless solid by conducting post-treatment as in Example 53.

$^1$H-NMR (CDCl$_3$)δ: 0.90(6H,t,J=7 Hz,—NCH$_2$CH$_2$CH$_3$X2), 1.11(2H,br-s), 1.18–1.48(4H,m), 1.24 (3H,s,C-16 or C-17), 1.26(3H,s,C-16 or C-17), 1.50–2.15 (7H,m), 1.68(3H,s,C-19), 1.83(3H,s,C-18), 2.19–2.82(6H, m), 2.24(3H,s,C-10:OCOCH$_3$), 2.44(3H,s,C-4:OCOCH$_3$), 3.78(1H,d,J=7 Hz,C-3), 3.97–4.33(2H,br), 4.19(1H,d,J=8 Hz,C-20a), 4.30(1H,d,J=8 Hz,C-20b), 4.41(1H,dd,J=7,11 Hz.C-7), 4.68(1H,d,J=4 Hz,C-2'), 4.95(1H,dd,J=2,10 Hz,C-5), 5.46(1H,dd,J=4,9 Hz,C-31), 5.66(1H,d,J=7 Hz,C-2), 6.26(1H,br-t,J=9 Hz,C-13), 6.27(1H,s,C-10), 7.24–7.65(8H, m,C-31-Ph, and C-2-Bz(m,p)), 8.14(2H,dd,J=1,8 Hz,C-2-Bz (o)). SI-MS m/z: 960 [M+H]$^+$ Example 56

13-O-[2-Hydroxy-3-phenyl-3-(4-piperidinopiperidinocarbonylamino)propionyl]-7-O-triethylsilylbaccatin III (Compound 57)

Using 4-piperidinopiperidinocarbonyl chloride (PPC, 24 mg, 0.11 mmol), the title compound (35 mg, 34%) was obtained as a yellow solid by conducting a reaction and post-treatment as in Example 52.

$^1$H-NMR (CDCl$_3$)δ: 0.51–0.65(6H,m,Si—CH$_2$X3), 0.92 (9H,t,J=8 Hz,Si—CH$_2$CH$_3$X3), 1.21(3H,s,C-16 or C-17), 1.24(3H,s,C-16 or C-17), 1.20–2.88(21H,m,pp,C-6a,C-6b and C-14), 1.70(3H,s,C-19), 1.95(3H,s,C-18), 2.18(3H,s,C-10:OCOCH$_3$), 2.45(3H,s,C-4:OCOCH$_3$), 3.79(1H,d,J=7 Hz,C-3), 3.84(1H,br-d,J=12 Hz,pp), 4.00(1H,br-d,J=12 Hz,pp), 4.21(1H,d,J=8 Hz,C-20a), 4.30(1H,d,J=8 Hz,C-20b), 4.46(1H,dd,J=7,11 Hz,C-7), 4.71(1H,d,J=3 Hz,C-21), 4.92(1H,dd,J=1,10 Hz,C-5), 5.41(1H,br-d,J=9 Hz,CONH), 5.50(1H,dd,J=3,9 Hz,C-3'), 5.68(1H,d,J=7 Hz,C-2), 6.28 (1H,br-t,J=9 Hz,C-13), 6.42(1H,s,C-10), 7.27–7.43(5H,m, C-3'-Ph), 7.47–7.63(3H,m,C-2-Bz(m,p)), 8.12(2H,dd,J=2,9 Hz,C-2-Bz(o)).

Example 57

13-O-[2-Hydroxy-3-phenyl-3-(4-piperidinopiperidinocarbonylamino)propionyl]baccatin III (Compound 58)

The compound (33 mg, 0.031 mmol) of Example 56 was dissolved in ethanol (4 ml), followed by the addition of 0.1 N hydrochloric acid (4 ml) at 0° C. under stirring. The resulting mixture was stirred for 4 days. Post-treatment and purification were conducted as in Example 53, whereby the title compound (24 mg, 83%) was obtained as a pale yellow solid.

$^1$H-NMR (CDCl$_3$)δ: 1.11(3H,s,C-16 or C-17), 1.23(3H,s,C-16 or C-17), 1.20–2.83(21H,m,pp,C-6a,C-6b and C-14), 1.68(3H,s,C-19), 1.83(3H,s,C-18), 2.24(3H,s,C-10:OCOCH$_3$), 2.45(3H,s,C-4:OCOCH$_3$), 3.77(1H,d,J=7 Hz,C-3), 3.97(1H,br-d,J=12 Hz,pp), 4.11(1H,br-d,J=12 Hz,pp), 4.20(1H,d,J=8 Hz,C-20a), 4.30(1H,d,J=8 Hz,C-20b), 4.40(1H,dd,J=7,11 Hz,C-7), 4.69(1H,d,J=3 Hz,C-2'), 4.94(1H,dd,J=1,10 Hz,C-5), 5.46(1H,dd,J=3,9 Hz,C-31), 5.65(1H,d,J=7 Hz,C-2), 5.70–6.02(1H,br,CONH), 6.26(1H,s,C-10), 6.30(1H,br-t,J=9 Hz,C-13), 7.25–7.43(5H,m,C-31-Ph), 7.48–7.64(3H,m,C-2-Bz(m,p)), 8.13(2H,dd,J=2,9 Hz,C-2-Bz(o)). SI-MS m/z: 944 [M+H]$^+$ Example 58

13-O-[2-Hydroxy-3-phenyl-3-(4-pyrrolidinopiperidinocarbonylamino)propionyl]-7-O-triethylsilylbaccatin III (Compound 59)

Using 4-pyrrolidinopiperidinocarbonyl chloride (25 mg, 0.12 mmol), the title compound (15 mg, 15%) was obtained as a pale yellow solid by conducting a reaction and post-treatment as in Example 52.

$^1$H-NMR (CDCl$_3$)δ: 0.50–0.65(6H,m,Si—CH$_2$X3), 0.93 (9H,t,J=8 Hz,Si—CH$_2$ CH X3), 1.18(3H,s,C-16 or C-17), 1.22(3H,s,C-16 or C-17), 1.26(2H,br-s,pip), 1.63–2.58(16H, m,pip,pyr,C-6a,C-6b and C-14), 1.72(3H,s,C-19), 1.99(3H, d,J=1 Hz,C-18), 2.18(3H,s,C-10:OCOCH$_3$), 2.55(3H,s,C-4:OCOCH$_3$), 2.88(1H,br-t,J=13 Hz), 3.58–3.73(1H,br-m), 3.79(1H,d,J=7 Hz,C-3), 3.98–4.02(1H,br-m), 4.28(1H,d,J=8 Hz,C-20a), 4.31(1H,d,J=8 Hz,C-20b), 4.47(1H,dd,J=7,11 Hz,C-7), 4.77(1H,d,J=2 Hz,C-21), 4.93(1H,dd,J=2,10Hz,C-5), 5.43–5.56(1H,br,CONH), 5.57(1H,dd,J=2,9 Hz,C-3'), 5.67(1H,d,J=7 Hz,C-2), 6.41(1H,br-t,J=9 Hz,C-13), 6.41 (1H,s,C-10), 7.27–7.57(8H,m,C-3'-Ph and C-2-Bz(m,p)), 8.15(2H,dd,J=2,8 Hz,C-2-Bz(o)).

Example 59

13-O-[2-Hydroxy-3-phenyl-3-(4-pyrrolidinopiperidinocarbonylamino)propionyl]baccatin III (Compound 60)

The compound (15 mg, 0.014 mmol) of Example 58 was dissolved in ethanol (1.5 ml), followed by the addition of 0.1 N hydrochloric acid (1.5 ml) at 0° C. under stirring. The resulting mixture was stirred for 4 days. Post-treatment and purification were conducted as in Example 53, whereby the title compound (9 mg, 65%) was obtained as a colorless solid.

$^1$H-NMR (CDCl$_3$)δ: 1.09(3H,s,C-16 or C-17), 1.22(3H, s,C-16 or C-17), 1.25(2H,br-s,pip), 1.40–2.95(17H,m,pip, pyr,C-6a,C-6b and C-14), 1.68(3H,s,C-19), 1.85(3H,d,J=1 Hz,C-18), 2.23(3H,s,C-10:OCOCH$_3$), 2.48(3H,s,C-4:OCOCH$_3$), 3.77(1H,d,J=7 Hz,C-3), 3.90–4.20(2H,br-m), 4.23(1H,d,J=8 Hz,C-20a), 4.29(1H,d,J=8 Hz,C-20b), 4.41 (1H,dd,J=7,11 Hz,C-7), 4.71(1H,d,J=3 Hz,C-21), 4.94(1H, dd,J=2,10 Hz,c-5), 5.51(1H,dd,J=3,9 Hz,C-3'), 5.65(1H,d, J=7 Hz,C-2), 6.26(1H,s,C-10), 6.34(1H,br-t,J=9 Hz,C-13), 7.24–7.62(8H,m,C-3'-Ph and C-2-Bz(m,p)), 8.14(2H,dd,J=2,9 Hz,C-2-Bz(o)). SI-MS m/z: 930 [M+H]$^+$ Example 60

13-O-[2-Hydroxy-3-(4-morpholinopiperidinocarbonylamino)-3-phenylpropionyl]-7-O-triethylsilylbaccatin III (Compound 61)

Using 4-morpholinopiperidinocarbonyl chloride (27 mg, 0.12 mmol), the title compound (45 mg, 44%) was obtained as a yellow solid by conducting a reaction and post-treatment as in Example 52.

$^1$H-NMR (CDCl$_3$)δ: 0.50–0.65(6H,m,Si—CH$_2$X3), 0.93 (9H,t,J=8 Hz,Si—CH$_2$CH$_3$X3), 1.10–1.40(3H,br-m,pp), 1.20(3H,s,C-16 or C-17), 1.25(3H,s,C-16 or C-17), 1.62–2.63(9H,m,pp,mor,C-6a,C-6b and C-14), 1.70(3H,s,C-19), 1.96(3H,s,C-18), 2.18(3H,s,C-10:OCOCH$_3$), 2.46(3H, s,C-4:OCOCH$_3$), 2.73–2.98(2H,m), 3.58–3.86(5H,m,mor and pp), 3.79(1H,d,J=7 Hz,C-3), 3.97(1H,br-d,J=14 Hz,pp), 4.21(1H,d,J=8 Hz,C-20a), 4.30(1H,d,J=8 Hz,C-20b), 4.46 (1H,dd,J=7,11 Hz,C-7), 4.72(1H,d,J=3 Hz,C-21), 4.91(1H, dd,J=1,9 Hz,C-5), 5.42(1H,d,J=9 Hz,CONH), 5.51(1H,dd, J=3,9 Hz,C-31), 5.69(1H,d,J=7 Hz,C-2), 6.29(1H,br-t,J=9 Hz,C-13), 6.42(1H,s,C-10), 7.25–7.62(8H,m,C-3'-Ph and C-2-Bz(m,p)), 8.12(2H,dd,J=2,9 Hz,C-2-Bz(o)).

Example 61

13-O-[2-Hydroxy-3-(4-morpholinopiperidinocarbonylamino)-3-phenylpropionyl] baccatin III (Compound 62)

The compound (45 mg, 0.042 mmol) of Example 60 was dissolved in ethanol (4.5 ml), followed by the addition of 0.1 N hydrochloric acid (4.5 ml) at 0° C. under stirring. The resulting mixture was stirred for 2 days. Post-treatment and purification were conducted as in Example 53, whereby the title compound (25 mg, 63%) was obtained as a colorless solid.

$^1$H-NMR (CDCl$_3$)δ: 1.08–1.39(4H,br-m,pp), 1.16(3H,s, C-16 or C-17), 1.26(3H,s,C-16 or C-17), 1.68(3H,s,C-19), 1.80–1.93(2H,m), 1.84(3H,s,C-18), 2.05–2.64(7H,m,C-6a, C-6b,C-14,pp and mor), 2.24(3H,s,C-10:OCOCH$_3$), 2.46 (3H,s,C-4:OCOCH$_3$), 2.78–2.98(2H,m), 3.58–3.75(4H,m, mor), 3.77(1H,d,J=7 Hz,C-3), 3.80(1H,br-d,J=13 Hz,pp), 3.96(1H,br-d,J=13 Hz,pp), 4.22(1H,d,J=8 Hz,C-20a), 4.30 (1H,d,J=8 Hz,C-20b), 4.41(1H,dd,J=7,11 Hz,C-7), 4.72(1H, d,J=3 Hz,C-2'), 4.94(1H,dd,J=2,10Hz,C-5), 5.42(1H,d,J=9 Hz,CONH), 5.50(1H,dd,J=3,9 Hz,C-31), 5.68(1H,d,J=7 Hz,C-2), 6.28(1H,s,C-10), 6.33(1H,br-t.J=9 Hz,C-13), 7.26–7.44(5H,m,C-31-Ph), 7.47–7.63(3H,m,C-2-Bz(m,p)), 8.12(2H,dd,J=2,9 Hz,C-2-Bz(o)). SI-MS mn/z: 946 [M+H]$^+$ Example 62

13-O-[2-Hydroxy-3-phenyl-3-{3-(4-piperidinopiperidinocarbonyl)propionylamino}propionyl]-7-O-triethylsilylbaccatin III (Compound 63)

3-(4-Piperidinopiperidinocarbonyl)propionic acid (29 mg, 0.12 mmol) was dissolved in dry methylene chloride (10 ml), followed by the addition of DCC (26 mg, 0.13 mmol). The resulting mixture was stirred at room temperature for 0.5 hour. To a solution of 13-O-(3-amino-2-hydroxy-3-phenylpropionyl)-7-O-triethylsilylbaccatin III, which had been prepared by conducting a reaction and post-treatment as in Example 52, in dry methylene chloride (10 ml), the above mixture was added and sodium hydrogencarbonate (9 mg, 0.11 mmol) was added further. The resulting mixture was stirred at room temperature for 21 hours. An insoluble matter was filtered off and the filtrate was then concentrated to dryness under reduced pressure, whereby a crude product was obtained. The crude product was purified by medium-pressure chromatography on a silica gel column (eluent: chloroform-methanol mixed solvent [9:1], detection: 225 nm) and reverse-phase high-performance liquid column chromatography (eluent: 10 mM potassium dihydrogenphosphate-acetonitrile mixed solvent [2:5], detection: 225 nm). Fractions containing the target compound were combined together. Chloroform and a 7% aqueous solution of sodium hydrogencarbonate were added to the thus-combined fractions, and the resulting mixture was allowed to separate into layers. The chloroform layer was washed with a saturated aqueous solution of sodium chloride, dried over anhydrous sodium sulfate, and then concentrated to dryness under reduced pressure, whereby the title compound (35 mg, 32%) was obtained as a pale yellow solid.

$^1$H-NMR (CDCl$_3$)δ: 0.44–0.60(6H,m,Si—CH$_2$X3), 0.87 (9H,t,J=8 Hz,Si—CH$_2$CH$_3$X3), 1.00–3.00(m), 3.40–4.00 (6H,m), 4.01(1H,d,J=9 Hz,C-20a), 4.05(1H,d,J=9 Hz,C-20b), 4.20(4H,m), 4.46–4.55(1H,m,C-7), 4.76(1H,d,J=3 Hz,C-21), 4.92(1H,d,J=9 Hz,C-5), 5.27–5.39(1H,m,C-31), 5.45(1H,d,J=7 Hz,C-2), 5.77–5.87(1H,m), 5.97(1H,q-like, C-13), 6.29(1H,s,C-10), 7.19–7.39(5H,m), 7.55–7.72(3H, m), 8.01(1H,d,J=7 Hz), 8.26(1H,d,J=8 Hz), 8.41(1H,br-d, J=6 Hz,CONH).

Example 63

13-O-C2-Hydroxy-3-phenyl-3-{3-(4-piperidinopiperidinocarbonyl)propionylamino}propionyl) bacca tin III (Compound 64)

The compound (35 mg, 0.031 mmol) of Example 62 was dissolved in ethanol (3.5 ml), followed by the addition of 0.1 N hydrochloric acid (3.5 ml) at 0° C. under stirring. The resulting mixture was stirred for 4 days. Post-treatment and purification were conducted as in Example 53, whereby the title compound (24 mg, 77%) was obtained as a colorless solid.

$^1$H-NMR (DMSO-d$_6$, 60° C.)δ: 1.07(3H,s,C-16 or C-17), 1.09(3H,s,C-16 or C-17), 1.20–3.35(m), 1.53(3H,s,C-19), 1.84(3H,d,J=1 Hz,C-18), 2.12(3H,s,C-10:OCOCH$_3$), 2.27 (3H,s,C-4:OCOCH$_3$), 3.67(1H,d,J=7 Hz,C-3), 4.01(1H,d, J=8 Hz,C-20a), 4.07(1H,d,J=8 Hz,C-20b), 4.14(1H,m,C-7), 4.49(1H,dd,J=5,6 Hz,C-21), 4.57(1H,s,C-1:OH), 4.69(1H, d,7 Hz,C-7:OH), 4.90(1H,dd,J=2,10 Hz,C-5), 5.32(1H,dd, J=5,9 Hz,C-31), 5.47(1H,d,J=7 Hz,C-2), 5.71(1H,br-d,J=6 Hz,C-2:OH), 5.98(1H,br-t,J=9 Hz,C-13), 6.32(1H,s,C-10), 7.18–7.40(5H,m,C-3'-Ph), 7.52–7.72(3H,m,C-2-Bz(m,p)), 8.01(2H,dd,J=2,8 Hz,C-2-Bz(o)), 8.29(1H,d,J=9 Hz,CONH). SI-MS m/z: 1000 [M+H]$^+$

Example 64

13-O-[2-Hydroxy-3-phenyl-3-{4-(4-piperidinopiperidinocarbonyl)butyrylamino}propionyl]-10-deacetylbaccatin III (Compound 65)

13-O-(3-Amino-2-hydroxy-3-phenylpropionyl)-7,10-bis-O-(2,2,2-trichloroethoxycarbonyl)-10-deacetylbaccatin III (106 mg, 0.10 mmol) and 4-(4-piperidinopiperidinocarbonyl)butyric acid (34 mg, 0.12 mmol) were dissolved in toluene (10 ml), followed by the addition of DCC (25 mg, 0.12 mmol). The resulting mixture was stirred at room temperature for 60 hours. A precipitate in the reaction mixture was filtered off, followed by the addition of a saturated aqueous solution of sodium hydrogencarbonate (50 ml) to the filtrate. The thus-obtained mixture was extracted with chloroform. The organic layer was dried over anhydrous magnesium sulfate and then concentrated to dryness under reduced pressure. The residue was purified by chromatography on a silica gel column (chloroform-methanol mixed solvent [19:1]). Eluted TLC single-spot fractions were combined together and then concentrated to dryness under reduced pressure, whereby the title compound (32 mg, 24%) was obtained as colorless crystals.

Subsequently, the crystals (30 mg, 0.022 mmol) was dissolved in acetic acid-methanol (1:1) mixed solvent (2 ml), followed by the addition of zinc powder (35 mg). The resulting mixture was stirred at 90° C. for 8 hours. A precipitate in the reaction mixture was filtered off, and water was added to the filtrate. The thus-obtained mixture was extracted with chloroform. The organic layer was washed with a saturated aqueous solution of sodium hydrogencarbonate and a saturated aqueous solution of sodium chloride, dried over anhydrous magnesium sulfate, and then concentrated to dryness under reduced pressure. The residue was purified by chromatography on a silica gel column (chloroform-methanol mixed solvent [19:1]). Eluted TLC single-spot fractions were combined together and then concentrated to dryness under reduced pressure, whereby the title compound (4 mg, 18%) was obtained as colorless crystals.

$^1$H-NMR (CDCl$_3$)δ: 1.12(3H,s), 1.25(3H,s), 1.26–1.50 (2H,m), 1.74(3H,s,C19-Me), 1.84(3H,s,C18-Me), 1.62–1.98 (7H,m), 2.51(3H,s,C4-OAc), 2.55(3H,s), 2.52–2.65(8H,m), 2.80–2.95(2H,m), 3.64–3.76(3H,m), 3.91(1H,d,J=8 Hz,C3-H), 4.37(1H,d,J=9 Hz,C20-H), 4.47(1H,d,J=9 Hz,C20-H), 4.66(1H,m), 4.78(1H,dd,J=8,11 Hz,C7-H), 4.91(1H,m,C5-H), 5.44(1H,s,C10-H), 5.64(1H,m,C3'-H), 5.76(1H,m,C2-H), 6.35(1H,m,C13-H), 7.00(1H,m), 7.24–7.58(8H,m,ArH), 8.19(2H,m,ArH). SI-MS m/z: 972 [M+H]$^+$

Example 65

13-O-[2-Hydroxy-3-phenyl-3-{(4-piperidinopiperidinocarbonylamino)acetylamino}propionyl]-10-deacetylbaccatin III (Compound 66)

13-O-(2-Amino-3-hydroxy-3-phenylpropionyl)-7,10-bis-O-(2,2,2-trichloroethoxycarbonyl)-10-deacetylbaccatin III (107 mg, 0.10 mmol), (4-piperidinopiperidinocarbonylamino)acetic acid (30 mg, 0.11 mmol) and DCC (23 mg, 0.11 mmol) were dissolved in methylene chloride, and the resultant solution was stirred over-night at room temperature and further for 3 hours at 45° C.

The reaction mixture was filtered. After the filtrate was concentrated, chloroform was added to the residue. The resulting mixture was washed with a saturated aqueous solution of sodium hydrogencarbonate. The organic layer was dried over anhydrous magnesium sulfate, and the solvent was then distilled off under reduced pressure. The residue was purified by chromatography on a silica gel column (chloroform-methanol mixed solvent [9:1→7:3]), whereby a purified product (96 mg) was obtained. Methanol (1 ml) and acetic acid (1 ml) were added to the purified product so that the purified product was dissolved. Zinc powder (65 mg) was added to the resultant solution, followed by stirring at 60° C. for 36 hours. Chloroform was added to the reaction mixture, and the resultant mixture was washed with a saturated aqueous solution of sodium hydrogencarbonate. The organic layer was dried over anhydrous magnesium sulfate, and the solvent was distilled off under reduced pressure. The residue was preliminarily purified by chromatography on a silica gel column (chloroform-methanol mixed solvent [7:3]). Further purification was conducted by reverse-phase high-performance liquid column chromatography (eluent: acetonitrile-water-trifluoroacetic acid mixed solvent (200:100:0.3]. Fractions containing the target compound were combined together, followed by the addition of chloroform and a 7% aqueous solution of sodium hydrogencarbonate. The thus-obtained mixture was allowed to separate into layers. The chloroform layer was washed with a saturated aqueous solution of sodium chloride, dried over anhydrous sodium sulfate, and then concentrated to dryness under reduced pressure, whereby the title compound (1 mg, 1%) was obtained.

$^1$H-NMR (CDCl$_3$)δ: 1.06(3H,s), 1.36(3H,s), 1.70(3H,s), 1.81(3H,s), 2.34(3H,s), 1.00–2.58(16H,m), 2.60–3.00(4H,m), 3.44–4.21(9H,m), 4.62(1H,d,J=2 Hz,C2'-H), 4.85(1H,d, J=9 Hz,C5-H), 5.12(1H,s,C10-H), 5.51(1H,d,J=9 Hz,C3'-H), 5.61(1H,d,J=7 Hz,C2-H), 6.23(1H,t,J=9 Hz,C13-H), 6.93(1H,s), 7.30(5H,m), 7.44(2H,t,J=8 Hz), 7.51(1H,t,J=7 Hz), 8.08(2H,d,J=7 Hz). SI-MS m/z: 959 [M+H]$^+$

Example 66

13-O-[2-Hydroxy-3-phenyl-3-(4-(4-piperidinopiperidinocarbonyloxy)benzoylamino) propionyl]-7,10-bis-O-(2,2,2-trichloroethoxycarbonyl)-10-deacetylbaccatin III (Compound 67) 4-(4-Piperidinopiperidinocarbonyloxy)benzoic acid (37 mg, 0.11 mmol) was dissolved in tetrahydrofuran (5 ml), followed by the addition of triethylamine (11 mg, 0.11 mmol) and ethyl chloroformate (12 mg, 0.11 mmol). The resulting mixture was stirred at −15° C. for 15 minutes. Subsequently, a solution of 13-O-(3-amino-2-hydroxy-3-phenylpropionyl)-7,10-bis-O-(212,2-trichloroethoxycarbonyl)-10-deacetylbaccatin III (106 mg, 0.10 mmol) in tetrahydrofuran (10 ml) was slowly added. After the thus-obtained mixture was stirred for 1 hour, they were reacted at room temperature for 14 hours. Water was added to the reaction mixture, followed by extraction with chloroform. The organic layer was washed with a saturated aqueous solution of sodium hydrogencarbonate, dried over anhydrous magnesium sulfate, and then concentrated to dryness under reduced pressure. The residue was purified by chromatography on a silica gel column (chloroform-methanol mixed solvent [19:1]). Eluted TLC single-spot fractions were combined together and then concentrated to dryness under reduced pressure, whereby the title compound (24 mg, 18%) was obtained as a colorless oil.

$^1$H-NMR (CDCl$_3$)δ: 1.18(3H,s,C-16 or C17-Me), 1.22 (3H,s,C-16 or C17-Me), 1.45–1.66(8H,m), 1.86(3H,s,C19-Me), 1.85–1.97(3H,m), 1.90(3H,s,C18-Me), 2.07(1H,m), 2.31(2H,m), 2.40(3H,s,C4-OAc), 2.50–2.65(6H,m), 2.81 (1H,m), 2.95(1H,m), 3.64(1H,s), 3.89(1H,d,J=7 Hz,C3-H), 4.20(1H,d,J=8 Hz,C20-H), 4.32(1H,d,J=9 Hz,C20-H), 4.18–4.33(2H,m), 4.60(1H,d,J=12 Hz,Troc), 4.77(2H,s, Troc), 4.79(1H,d,J=2 Hz,C2'-H), 4.91(1H,d,J=12 Hz,Troc), 4.95(1H,d,J=8 Hz,C5-H), 5.53(1H,dd,J=8,11 Hz,C7-H), 5.69(1H,d,J=11 Hz,C2-H), 5.78(1H,d,J=9 Hz,C3'-H), 6.20 (1H,t,C13-H), 6.21(1H,s,C10-H), 7.09(2H,d,J=9 Hz,ArH), 7.20(1H,m), 7.34–7.62(8H,m,ArH), 7.75(2H,d,J=9 Hz,ArH), 8.12(2H,d,J=7 Hz,ArH).

Example 67

13-O-[2-Hydroxy-3-phenyl-3-{4-(4-piperidinopiperidinocarbonyloxy) benzoylamino}propionyl]-10-deacetylbaccatin III (Compound 68)

The compound (20 mg, 0.014 mmol) of Example 66 was dissolved in acetic acid-methanol (1:1) mixed solvent (2 ml), followed by the addition of zinc powder (13 mg). The resulting mixture was stirred at 90° C. for 8 hours. A precipitate in the reaction mixture was filtered off and water was added to the filtrate. The resulting mixture was extracted with chloroform. The organic layer was washed with a saturated aqueous solution of sodium hydrogencarbonate and a saturated aqueous solution of sodium chloride, dried over anhydrous magnesium sulfate, and then concentrated to dryness under reduced pressure. The residue was purified by chromatography on a silica gel column (chloroform-methanol mixed solvent [19:1]). Eluted TLC single-spot fractions were combined together and then concentrated to dryness under reduced pressure, whereby the title compound (6 mg, 40%) was obtained as colorless crystals.

$^1$H-NMR (CDCl$_3$)δ: 1.07(3H,s,C-16 or C17-Me), 1.16 (3H,s,C-16 or C17-Me), 1.20–1.26(1H,m), 1.73(6H,s,C18-Me and C19-Me), 1.52–1.90(11H,m), 2.03–2.31(4H,m), 2.39(3H,s,C4-OAc), 2.52(1H,m), 2.77(1H,m), 2.90(1H,m), 3.62(1H,s), 3.85(1H,d,J=7 Hz,C3-H), 4.20(1H,d,J=8 Hz,C20-H), 4.28(1H,d,J=9 Hz,C20-H), 4.40(1H,m), 4.75 (1H,s,C2'-H), 4.91(1H,d,J=10 Hz,C5-H), 5.15(1H,s,C10-H), 5.63(1H,d,J=7 Hz,C2-H), 5.78(1H,d,J=9 Hz,C3'-H), 6.17 (1H,t,C13-H), 7.08(2H,d,J=9 Hz,ArH), 7.24–7.59(8H,m, ArH), 7.84(2H,d,J=8 Hz,ArH), 8.10(2H,d,J=8 Hz,ArH). SI-MS m/z: 1022 [M+H]$^+$ Example 68

13-O-[3-(4-Benzyloxycarbonylpiperazinocarbonylamino)-2-hydroxy-3-phenylpropionyl]-7-O-triethylsilylbaccatin III (Compound 69)

Using 4-benzyloxycarbonylpiperazinocarbonyl chloride (33 mg, 0.12 mmol), the title compound (27 mg, 25%) was obtained as a yellow solid by conducting a reaction and post-treatment as in Example 52.

$^1$H-NMR (CDCl$_3$)δ: 0.50–0.64(6H,m,Si—CH$_2$CH$_3$X3), 0.91(9H,t,J=8 Hz,Si—CH$_2$CH$_3$X3), 1.19(3H,s,C-16 or C-17), 1.23(3H,s,C-16 or C-17), 1.68–1.78(1H,br), 1.69(3H, s,C-19), 1.83–1.97(1H,m,C-6a), 1.89(3H,d,J=1 Hz,C-18), 2.14–2.32(2H,m,C-14), 2.18(3H,s,C-10:OCOCH$_3$), 2.35 (3H,s,C-4:OCOCH$_3$), 2.45–2.57(1H,m,C-6b), 3.20–3.58 (8H,m,piperazine), 3.78(1H,d,J=7 Hz,C-3), 4.16(1H,d,J=8 Hz,C-20a), 4.29(1H,d,J=8 Hz,C-20b), 4.43(1H,dd,J=7,11 Hz,C-7), 4.68(1H,d,J=3 Hz,C-21), 4.91(1H,dd,J=2,9 Hz,C-5), 5.12(2H,s,—CH$_2$Ph), 5.40(1H,d,J=9 Hz,CONH), 5.47 (1H,dd,J=3,9 Hz,C-3'), 5.67(1H,d,J=7 Hz,C-2), 6.16(1H,m, C-13), 6.42(1H,s,C-10), 7.27–7.64(13H,m,C-3'-Ph,C-2-Bz (m,p) and —CH$_2$Ph), 8.10(2H,dd,J=1,8 Hz,C-2-Bz(o)).

Example 69

13-O-[2-Hydroxy-3-phenyl-3-(piperazinocarbonylamino)propionyl]baccatin III (Compound 70)

The compound (41 mg, 0.037 mmol) of Example 68 was dissolved in methanol (10 ml), followed by the addition of 10% palladium on charcoal (10 mg). The resulting mixture was vigorously stirred at room temperature for 5.5 hours under a hydrogen gas atmosphere. The catalyst was filtered off and the filtrate was then concentrated to dryness under reduced pressure, whereby a colorless solid (38 mg) was obtained. The thus-obtained colorless solid was dissolved in ethanol (3.8 ml), followed by the addition of 0.1 N hydrochloric acid (3.8 ml) at 0° C. under stirring. The thus-obtained mixture was stirred for 3 days. Post-treatment and purification were conducted as in Example 53, whereby the title compound (21 mg, 68%) was obtained as a colorless solid.

$^1$H-NMR (CDCl$_3$)δ: 1.13(3H,s,C-16 or C-17), 1.25(3H, s,C-16 or C-17), 1.67(3H,s,C-19), 1.80–1.92(1H,m,C-6a), 1.79(3H,s,C-18), 2.10–2.30(2H,m,C-14), 2.23(3H,s,C-10:OCOCH$_3$), 2.36(3H,s,C-4:OCOCH$_3$), 2.47–2.58(1H,m, C-6b), 2.79(4H,br-s,piperazine), 2.80–5.60(1H,br), 3.34

(4H,m,piperazine), 3.77(1H,d,J=7 Hz,C-3), 4.16(1H,d,J=8 Hz,C-20a), 4.27(1H,d,J=8 Hz,C-20b), 4.39(1H,dd,J=7,11 Hz,C-7), 4.67(1H,d,J=3 Hz,C-2'), 4.93(1H,dd,J=1,9 Hz,C-5), 5.43(1H,dd,J=3,8 Hz,C-3'), 5.49(1H,br), 5.65(1H,d,J=7 Hz,C-2), 6.20(1H,br-t,J=9 Hz,C-13), 6.27(1H,s,C-10), 7.25–7.65(8H,m,C-31-Ph and C-2-Bz(m,p)), 8.10(2H,dd,J= 1,8 Hz,C-2-Bz(o)). SI-MS m/z: 862 [M+H]$^+$ Example 70

13-O-[2-Hydroxy-3-(4-methylpiperazinocarbonylamino)-3-phenylpropionyl]-7-O-triethylsilylbaccatin III (Compound 71)

Using 4-methylpiperazinocarbonyl chloride (19 mg, 0.12 mmol), the title compound (16 mg, 17%) was obtained as a pale yellow solid by conducting a reaction and post-treatment as in Example 52.

$^1$H-NMR (CDCl$_3$)δ: 0.50–0.64(6H,m,Si—CH$_2$CH$_3$X3), 0.92(9H,t,J=8 Hz,Si—CH$_2$CH$_3$X3), 1.20(3H,s,C-16 or C-17), 1.23(3H,s,C-16 or C-17), 1.69(3H,s,C-19), 1.78(1H, br-s), 1.83–1.94(1H,m,C-6a), 1.91(3H,d,J=1 Hz,C-18), 2.13–2.40(6H,br-m,C-14,pip-CH$_2$X2), 2.18(3H,s,C-10:OCOCH$_3$), 2.27(3H,s,N—CH$_3$), 2.36(3H,s,C-4:OCOCH$_3$), 2.45–2.57(1H,m,C-6b), 3.25–3.50(4H,br-m, pip-CH$_2$X2), 3.79(1H,d,J=7 Hz,C-3), 4.16(1H,d,J=8 Hz,C-20a), 4.28(1H,d,J=8 Hz,C-20b), 4.44(1H,dd,J=7,11 Hz,C-7), 4.67(1H,d,J=3 Hz,C-2'), 4.91(1H,dd,J=2,9 Hz,C-5), 5.39 (1H,d,J=9 Hz,CONH), 5.46(1H,dd,J=3,9 Hz,C-31), 5.67 (1H,d,J=7 Hz,C-2), 6.16(1H,br-t,J=9 Hz,C-13), 6.42(1H,s, C-10), 7.26–7.64(8H,m,C-31-Ph and C-2-Bz(m,p)), 8.10 (2H,dd,J=2,9 Hz,C-2-Bz(o)).

Example 71

13-O-[2-Hydroxy-3-(4-methylpiperazinocarbonylamino)-3-phenylpropionyl]baccatin III (Compound 72)

The compound (16 mg, 0.016 mmol) of Example 70 was dissolved in ethanol (1.6 ml), followed by the addition of 0.1 N hydrochloric acid (1.6 ml) at 0° C. under stirring. The resulting mixture was stirred for 4 days. Post-treatment and purification were conducted as in Example 53, whereby the title compound (11 mg, 78%) was obtained as a colorless solid.

$^1$H-NMR (CDCl$_3$)δ: 1.14(3H,s,C-16 or C-17), 1.26(3H, s,C-16 or C-17), 1.67(3H,s,C-19), 1.79(3H,s,C-18), 1.80–1.92(1H,m,C-6a), 2.13–2.43(6H,m,C-14,pip-CH$_2$X2), 2.24(3H,s,C-10:OCOCH$_3$), 2.28(3H,s,N—CH$_3$), 2.37(3H,s, C-4:OCOCH$_3$), 2.48–2.59(1H,m,C-6b), 3.26–3.50(4H,m, pip-CH$_2$X2), 3.77(1H,d,J=7 Hz,C-3), 4.16(1H,d,J=8 Hz,C-20a), 4.28(1H,d,J=8 Hz,C-20b), 4.40(1H,dd,J=7,11 Hz,C-7), 4.67(1H,d,J=3 Hz,C-2'), 4.93(1H,dd,J=2,10 Hz,C-5), 5.39(1H,J=8 Hz,CONH), 5.44(1H,dd,J=3,8 Hz,C-31), 5.65 (1H,d,J=7 Hz,C-2), 6.20(1H,br-t,J=9 Hz,C-13), 6.27(1H,s, C-10), 7.25–7.70(8H,m,C-3'-Ph and C-2-Bz(m,p)), 8.10(2H, dd,J=2,9 Hz,C-2-Bz(o)). SI-MS m/z: 876 [M+H]$^+$ Example 72

13-O-[3-(4-Ethylpiperazinocarbonylamino)-2-hydroxy-3-phenylpropionyl]-7-O-triethylsilylbaccatin III (Compound 73)

Using 4-ethylpiperazinocarbonyl chloride (19 mg, 0.11 mmol), the title compound (15 mg, 16%) was obtained as a colorless solid by conducting a reaction and post-treatment as in Example 52.

$^1$H-NMR (CDCl$_3$)δ: 0.50–0.64(6H,m,Si—CH$_2$X3), 0.92 (9H,t,J=8 Hz,Si—CH$_2$CH$_3$X3), 1.07(3H,t,J=7 Hz,N—CH$_2$CH$_3$), 1.20(3H,s,C-16 or C-17), 1.23(3H,s,C-16 or C-17), 1.69(3H,s,C-19), 1.76(1H,s,C-1:OH), 1.83–1.94(1H, m,C-6a), 1.91(3H,d,J=1 Hz,C-18), 2.16–2.58(9H,m,C-14, pip-CH$_2$X2,N—CH$_2$CH$_3$ and C-6b), 2.18(3H,s,C-10:OCOCH$_3$), 2.37(3H,s,C-4:OCOCH$_3$), 3.25–3.50(4H,m, pip-CH$_2$X2), 3.79(1H,d,J=7 Hz,C-3), 4.16(1H,d,J=8 Hz,C-20a), 4.28(1H,d,J=8 Hz,C-20b), 4.44(1H,dd,J=7,11 Hz,C-7), 4.68(1H,d,J=3 Hz,C-2'), 4.91(1H,dd,J=2,10 Hz,C-5), 5.41(1H,br-d,J=9 Hz,CONH), 5.46(1H,dd,J=3,9 Hz,C-31), 5.67(1H,d,J=7 Hz,C-2), 6.17(1H,br-t,J=9 Hz,C-13), 6.42 (1H,s,C-10), 7.27–7.64(8H,m,C-3'-Ph and C-2-Bz(m,p)), 8.10(2H,dd,J=2,9 Hz,C-2-Bz(o)).

Example 73

13-O-[3-(4-Ethylpiperazinocarbonylamino)-2-hydroxy-3-phenylpropionyl]baccatin III (Compound 74)

The compound (15 mg, 0.019 mmol) of Example 72 was dissolved in ethanol (2 ml), followed by the addition of 0.1 N hydrochloric acid (2 ml) at 0° C. under stirring. The resulting mixture was stirred for 4 days. Post-treatment was conducted as in Example 531 whereby the title compound (11 mg, 85%) was obtained as a colorless solid.

$^1$H-NMR (CDCl$_3$)δ: 1.07(3H,t,J=7 Hz,N—CH$_2$CH$_3$), 1.14(3H,s,C-16 or C-17), 1.26(3H,s,C-16 or C-17), 1.67(3H, s,C-19), 1.79(3H,d,J=1 Hz,C-18), 1.81–1.92(1H,m,C-6a), 2.13–2.60(9H,m,C-14,pip-CH$_2$X2,N—CH$_2$CH$_3$ and C-6b), 2.25(3H,s,C-10:OCOCH$_3$), 2.38(3H,s,C-4:OCOCH$_3$), 3.30–3.50(4H,m,pip-CH$_2$X2), 3.78(1H,d,J=7 Hz,C-3), 4.17 (1H,d,J=8 Hz,C-20a), 4.29(1H,d,J=8 Hz,C-20b), 4.40(1H, dd,J=7,11 Hz,C-7), 4.67(1H,d,J=3 Hz,C-2'), 4.94(1H,dd,J= 2,10 Hz,C-5), 5.37(1H,br-d,J=8 Hz,CONH), 5.44(1H,dd,J= 3,8 Hz,C-31), 5.66(1H,d,J=7 Hz,C-2), 6.21(1H,br-t,J=9 Hz,C-13), 6.27(1H,s,C-10), 7.27–7.43(5H,m,C-31-Ph), 7.47–7.65(3H,m,C-2-Bz(m,p)), 8.11(2H,dd,J=2,9 Hz,C-2-Bz(o)). SI-MS m/z: 890 [M+H]$^+$ Example 74

13-O-[2-Hydroxy-3-(4-(isopropylaminocarbonylmethyl) piperazinocarbonylamino)-3-phenylpropionyl]-7,10-bis-O-(2,2,2-trichloroethoxycarbonyl)-10-deacetylbaccatin III (Compound 75)

13-O-(3-Amino-2-hydroxy-3-phenylpropionyl)-7,10-bis-O-(2,2,2-trichloroethoxycarbonyl)-10-deacetylbaccatin III (106 mg, 0.10 mmol) and 4-(isopropylaminocarbonylmethyl)piperazinocarbonyl chloride (27 mg, 0.11 mmol) were dissolved in tetrahydrofuran (10 ml), followed by the addition of triethylamine (11 mg, 0.11 mmol). The resulting mixture was stirred at room temperature for 15 hours. The reaction mixture was concentrated to dryness under reduced pressure. The residue was purified by chromatography on a silica gel column (chloroform-methanol mixed solvent [29:1]). Eluted TLC single-spot fractions were combined together and then concentrated to dryness under reduced pressure, whereby the title compound (48 mg, 20%) was obtained as colorless crystals.

$^1$H-NMR (CDCl$_3$)δ: 1.12(3H,s,isopropyl-Me), 1.14(3H,s, isopropyl-Me), 1.19(3H,s,C-16 or C17-Me), 1.26(3H,s,C-16 or C17-Me), 1.85(3H,s,C19-Me), 1.89(3H,s,C18-Me), 2.01–2.03(1H,m), 2.27(2H,m), 2.39(3H,s,C4-OAc), 2.39–2.45(4H,m,Piperazine-H), 2.61(1H,m,C6-H), 2.93 (2H,s,CH$_2$), 3.35–3.39(4H,m,Piperazine-H), 3.89(1H,d,J=7 Hz,C3-H), 4.06(1H,m,isopropyl-CH), 4.17(1H,d,J=9 Hz,C20-H), 4.31(1H,d,J=9 Hz,C20-H), 4.61(1H,d,J=12 Hz,Troc), 4.69(1H,d,J=3 Hz,C2'-H), 4.78(2H,s,Troc), 4.90 (1H,d,J=12 Hz,Troc), 4.94(1H,d,J=8 Hz,C5-H), 5.47(1H,m, C7-H), 5.53(1H,m,C3'-H), 5.68(1H,d,J=7 Hz,C2-H), 6.20 (1H,t,J=8 Hz,C13-H), 6.22(1H,s), 6.77(1H,d,J=9 Hz,NH), 7.31–7.66(5H,m,ArH), 7.45–7.53(2H,m,ArH), 7.48–7.68 (1H,m,ArH), 8.08–8.10(2H,m,ArH).

Example 75

13-O-[2-Hydroxy-3-{4-(isopropylaminocarbonylmethyl) piperazinocarbonylamino}-3-phenylpropionyl]-10-deacetylbaccatin III (Compound 76)

The compound (48 mg, 0.038 mmol) of Example 74 was dissolved in acetic acid-methanol (1:1) mixed solvent (2 ml), followed by the addition of zinc powder (50 mg). The resulting mixture was stirred at 60° C. for 2.5 hours. A precipitate in the reaction mixture was filtered off, and water was added to the filtrate. The thus-obtained mixture was extracted with chloroform. The organic layer was washed with a saturated aqueous solution of sodium hydrogencarbonate and a saturated aqueous solution of sodium chloride, dried over anhydrous magnesium sulfate, and then concentrated to dryness under reduced pressure. The residue was purified by chromatography on a silica gel column (chloroform-methanol mixed solvent [19:1]). Eluted TLC single-spot fractions were combined together and then concentrated to dryness under reduced pressure, whereby the title compound (20 mg, 60%) was obtained as colorless crystals.

$^1$H-NMR (CDCl$_3$)δ: 1.11(3H,s,C-16 or C17-Me), 1.12 (3H,s,isopropyl-Me), 1.14(3H,s,isopropyl-Me), 1.22(3H,s,C-16 or C17-Me), 1.73(3H,s,C19-Me), 1.79(3H,s,C18-Me), 1.82–1.90(2H,m), 2.03(1H,s), 2.19–2.26(2H,m), 2.36(3H,s,C4-OAc), 2.39–2.45(4H,m,Piperazine-H), 2.52(1H,m,C6-H), 2.94(2H,s,isopropyl-CH$_2$), 3.35–3.43(4H,m,Piperazine-H), 3.85(1H,d,J=7 Hz,C3-H), 4.06(1H,m,CH), 4.17(1H,d,J=8 Hz,C20-H), 4.22(1H,br), 4.29(1H,d,J=8 Hz,C20-H), 4.34(1H,br), 4.67(1H,d,J=3 Hz,C2'-H), 4.92(1H,d,J=8 Hz,C5-H), 5.21(1H,s,C10-H), 5.43(1H,dd,J=3,8 Hz,C3'-H), 5.64(1H,d,J=7 Hz,C2-H), 5.66(1H,s), 6.18(1H,t,J=8 Hz,C13-H), 6.79(1H,d,J=9 Hz,NH), 7.24–7.60(8H,m,ArH), 8.09(2H,d,J=7 Hz,ArH). SI-MS m/z: 919 [M+H]$^+$

Example 76

13-O-[2-Hydroxy-3-{3-(4-isopropylaminocarbonylmethylpiperazinocarbonyl)propionylamino}-3-phenylpropionyl]-7-O-triethylsilylbaccatin III (Compound 77)

Using 3-(4-isopropylaminocarbonylmethylpiperazinocarbonyl)propionic acid (33 mg, 0.12 mmol), the title compound (25 mg, 23%) was obtained as a colorless solid by conducting a reaction and post-treatment as in Example 62.

$^1$H-NMR (CDCl$_3$)δ: 0.49–0.65(6H,m,Si—CH$_2$X3), 0.92 (9H,t,J=8 Hz,Si—CH$_2$CH$_3$X3), 1.17(6H,d,J=6 Hz,—CH(CH$_3$)$_2$), 1.23(3H,s,C-16 or C-17), 1.24(3H,s,C-16 or C-17), 1.70(3H,s,C-19), 1.82–1.95(1H,m), 2.00(3H,s,C-18), 2.13–2.74(10H,m), 2.19(3H,s,C-10:OCOCH$_3$), 2.39(3H,s,C-4:OCOCH$_3$), 2.80–3.14(3H,m), 2.86(2H,s,—COCH$_2$N═), 3.20–3.30(1H,br-m), 3.44–3.56(1H,br-m), 3.80(1H,d,J=7 Hz,C-3), 4.01–4.15(1H,m,—CH(CH$_3$)$_2$), 4.22(2H,s,C-20), 4.46(1H,dd,J=7,11 Hz,C-7), 4.67(1H,br-s,C-2'), 4.91(1H,dd,J=1,9 Hz,C-5), 5.61(1H,dd,J=2,9 Hz,C-3'), 5.68(1H,d,J=7 Hz,C-2), 6.29(1H,br-t,J=9 Hz,C-13), 6.42 (1H,s,C-10), 6.71(1H,br-d,J=9 Hz), 6.89(1H,br-d,J=9 Hz), 7.27–7.63(8H,m,C-3'-Ph and C-2-Bz(m,p)), 8.13(2H,dd,J=1,9 Hz,C-2-Bz(o)).

Example 77

13-O-[2-Hydroxy-3-{3-(4-isopropylaminocarbonylmethylpiperazinocarbonyl)propionylamino}-3-phenylpropionyl]baccatin III (Compound 78)

The compound (25 mg, 0.022 mmol) of Example 66 was dissolved in ethanol (2.5 ml), followed by the addition of 0.1 N hydrochloric acid (2.5 ml) at 0° C. under stirring. The resulting mixture was stirred for 4 days. Post-treatment and purification were conducted as in Example 53, whereby the title compound (20 mg, 90%) was obtained as a colorless solid.

$^1$H-NMR (CDCl$_3$)δ: 1.16(3H,s,C-16 or C-17), 1.17(6H, d,J=7 Hz,—CH(CH$_3$)$_2$), 1.30(3H,s,C-17), 1.69(3H, s,C-19), 1.82–1.94(1H,m), 1.88(3H,d,J=1 Hz,C-18), 2.19–2.74(11H,m), 2.24(3H,s,C-10:OCOCH$_3$), 2.40(3H,s, C-4:OCOCH$_3$), 2.87(2H,s,—COCH$_2$N═), 2.91–3.29(4H, m), 3.40–3.51(1H,br-m), 3.73–3.96(1H,br), 3.79(1H,d,J=7 Hz,C-3), 4.00–4.15(1H,m,—CH(CH$_3$)$_2$), 4.21(1H,d,J=9 Hz,C-20a), 4.25(1H,d,J=9 Hz,C-20b), 4.40(1H,br-t,J=8 Hz,C-7), 4.67(1H,d,J=2 Hz,c-2'), 4.92(1H,dd,J=2,10 Hz,C-5), 5.61(1H,dd,J=2,9 Hz,C-3'), 5.67(1H,d,J=7 Hz,C-2), 6.29(1H,s,C-10), 6.34(1H,br-t,J=9 Hz,C-13), 6.70(1H,br-d, J=8 Hz), 6.84(1H,d,J=9 Hz), 7.29–7.43(5H,m,c-3'-Ph), 7.48–7.63(3H,m,C-2-Bz(m,p)), 8.13(2H,dd,J=2,9 Hz,C-2-Bz(o)). SI-MS m/z: 1017 [M+H]$^+$

Example 78

13-O-[2-Hydroxy-3-{(4-isopropylaminocarbonylmethylpiperazinocarbonyloxy)acetylamino}-3-phenylpropionyl]-7-O-triethylsilylbaccatin III (Compound 79)

Using (4-isopropylaminocarbonylmethylpiperazinocarbonyloxy) acetic acid (33 mg, 0.12 mmol), the title compound (39 mg, 35%) was obtained as a colorless solid by conducting a reaction and post-treatment as in Example 62.

$^1$H-NMR (CDCl$_3$)δ: 0.42–0.59(6H,m,Si—CH$_2$CH$_3$X3), 0.85(9H,t,J=8 Hz,Si—CH$_2$CH$_3$X3), 1.07(3H,d,J=6 Hz,—CH(CH$_3$)$_2$), 1.08(3H,d,J=6 Hz,—CH(CH$_3$)$_2$), 1.15(3H,s,C-16 or C-17), 1.17(3H,s,C-16 or C-17), 1.63(3H,s,C-19), 1.77–1.98(1H,m), 1.84(3H,s,C-18), 2.08–2.50(8H,m), 2.11 (3H,s,C-10:OCOCH$_3$), 2.32(3H,s,C-4:OCOCH$_3$), 2.83(2H, s,—COCH$_2$N═), 2.97–3.58(4H,br-m), 3.71(1H,d,J=7 Hz,C-3), 3.92–4.05(1H,m,—CH(CH$_3$)$_2$), 4.15(1H,d,J=7 Hz,C-20a), 4.18(1H,d,J=7 Hz,C-20b), 4.36(1H,dd,J=7,11 Hz,C-7), 4.43(1H,d,J=15 Hz,—COOCH(H)CONH—), 4.56 (1H,d,J=15 Hz,—COOCH(H)CONH—), 4.66(1H,d,J=2 Hz,C-2'), 4.83(1H,d,J=8 Hz,C-5), 5.57(1H,dd,J=2,9 Hz,C-3'), 5.61(1H,d,J=7 Hz,C-2), 6.17(1H,br-t,J=9 Hz,c-13), 6.34 (1H,s,C-10), 6.65(1H,br-d,J=7 Hz), 6.88(1H,d,J=9 Hz), 7.20–7.59(8H,m,C-3'-Ph and C-2-Bz(m,p)), 8.05(2H,d,J=7 Hz,C-2-Bz(o)).

Example 79

13-O-[2-Hydroxy-3-{(4-isopropylaminocarbonylmethylpiperazinocarbonyloxy)acetylamino}-3-phenylpropionyl]baccatin III (Compound 80)

The compound (39 mg, 0.034 mmol) of Example 78 was dissolved in ethanol (3.9 ml), followed by the addition of 0.1 N hydrochloric acid (3.9 ml) at 0° C. under stirring. The resulting mixture was stirred for 4 days. Post-treatment and purification were conducted as in Example 53, whereby the title compound (30 mg, 87%) was obtained as a colorless solid.

$^1$H-NMR (CDCl$_3$)δ: 1.15(3H,d,J=7 Hz,—CH(CH$_3$)$_2$), 1.16(3H,d,J=7 Hz,—CH(CH$_3$)$_2$), 1.17(3H,s,C-16 or C-17), 1.28(3H,s,C-16 or C-17), 1.69(3H,s,C-19), 1.88(3H,d,J=1 Hz,C-18), 1.83–1.93(1H,m), 2.24(3H,s,C-10:OCOCH$_3$), 2.25–2.44(6H,m), 2.39(3H,s,C-4:OCOCH$_3$), 2.48–2.63(2H, m), 2.68(1Hfs), 2.90(2H,s,—COCH$_2$N═), 3.00–3.58(4H, m), 3.78(1H,d,J=7 Hz,C-3), 4.00–4.11(1H,m,—CH(CH$_3$)$_2$), 4.25(2H,s,C-20), 4.39(1H,br-m,C-7), 4.49(1H,d,J=15 Hz,—COOCH(H)CONH—), 4.63(1H,d,J=15 Hz,—COOCH(H)CONH—), 4.74(1H,d,J=2 Hz,C-2'), 4.92(1H,dd,J=2,10Hz, C-5), 5.65(1H,dd,J=2,10 Hz,C-3'), 5.68(1H,d,J=7 Hz,C-2), 6.28(1H,s,C-10), 6.30(1H,br-t,J=8 Hz,C-13), 6.71(1H,br-d, J=7 Hz), 6.91(1H,d,J=9 Hz), 7.30–7.64(8H,m,C-3'-Ph and C-2-Bz(m,p)), 8.13(2H,dd,J=2,9 Hz,C-2-Bz(o)). SI-MS m/z: 1019 [M+H]$^+$ Alternative Synthesis Process for Compound 80

Formic acid (3 ml) was added to 13-O-[3-(tert-butoxycarbonyl)-2,2-dimethyl-4-phenyl-5- oxazolidinecarbonyl]-7-O-triethylsilylbaccatin III (0.07 g, 0.07 mmol). The resulting mixture was stirred at room temperature for 3 hours. Subsequent to confirmation of full consumption of the raw material by TLC, chloroform was added to the reaction mixture, and the thus-obtained mixture was washed with a saturated aqueous solution of sodium hydrogencarbonate. The organic layer was dried over anhydrous magnesium sulfate and the solvent was distilled off under reduced pressure. The residue was dissolved in methylene chloride, followed by the addition of [4-(isopropylaminocarbonylmethyl)piperazinocarbonyloxy]acetic acid (32 mg, 0.11 mmol) and DCC (23 mg, 0.11 mmol). The resulting mixture was stirred under reflux for 20 hours. The reaction mixture was filtered. After the filtrate was concentrated, chloroform was added. The thus-obtained mixture was washed with a saturated aqueous solution of sodium hydrogencarbonate. The organic layer was dried over anhydrous magnesium sulfate and the solvent was distilled off under reduced pressure. The residue was preliminarily purified by chromatography on a silica gel column (chloroform-methanol mixed solvent [97:3→19:1]). Further purification was conducted by reverse-phase high-performance liquid column chromatography (eluent: acetonitrile-water mixed solvent [1:1], whereby the title compound (5 mg, 7%) was obtained.

Example 80

13-O-[2-Hydroxy-3-phenyl-3-(N,N,N'-trimethylethylenediaminocarbonylamino)propionyl]-7-O-triethylsilylbaccatin III (Compound 81)

13-O-(3-Amino-2-hydroxy-3-phenylpropionyl)-7-O-triethylsilylbaccatin III (57 mg, 0.07 mmol), which had been prepared by conducting a reaction and post-treatment as in Example 52, was dissolved in dry pyridine (20 ml), to which N,N,N'-trimethylethylenediaminocarbonyl chloride hydrochloride (20 mg, 0.10 mmol) and triethylamine (14 at, 0.1 mmol) were added. The resulting mixture was stirred at 50° C. for 2 days. Carbonyl chloride and triethylamine were added further, and were reacted likewise. A precipitate was filtered off, and the solvent was distilled off under reduced pressure. The residue was purified by chromatography on an ODS column (eluent: 10 mM potassium dihydrogenphosphate-acetonitrile mixed solvent [1:2], detection: 225 nm). Fractions containing the target compound were combined together, followed by the addition of chloroform and a 7% aqueous solution of sodium hydrogencarbonate. The thus-obtained mixture was allowed to separate into layers. The chloroform layer was washed with a saturated aqueous solution of sodium chloride, dried over anhydrous sodium sulfate, and then concentrated to dryness under reduced pressure, thereby the title compound (8 mg, 12%) was obtained as a colorless solid.

¹H-NMR (CDCl₃)δ: 0.50–0.65(6H,m,Si—CH₂X3), 0.92 (9H,t,J=8 Hz,Si—CH₂CH₃X3), 1.20(3H,s,C-16 or C-17), 1.26(3H,s,C-16 or C-17), 1.68(3H,s,C-19), 1.82–1.92(1H, m,C-6a), 1.97(3H,s,C-18), 2.18(3H,s,C-10:OCOCH₃), 2.22–2.38(2H,m,C-14), 2.32(3H,s,C-4:OCOCH₃), 2.45–2.55(1H,m,C-6b), 2.68(6H,br-s,N(CH₃)₂), 2.94–3.14 (2H,br-m), 3.02(3H,s,CONCH₃), 3.28–3.36(1H,br-m), 3.80 (1H,d,J=7 Hz,C-3), 4.00–4.12(1H,br-m), 4.15(1H,d,J=8 Hz,C-20a), 4.27(1H,d,J=8 Hz,C-20b), 4.45(1H,dd,J=7,10 Hz,C-7), 4.67(1H,d,J=3 Hz,C-2'), 4.91(1H,dd,J=1,10Hz,C-5), 5.40(1H,dd,J=3,9 Hz,C-3'), 5.67(1H,d,J=7 Hz,C-2), 5.98 (1H,br,CONH), 6.17(1H,br-t,J=9 Hz,C-13), 6.43(1H,s,C-10), 7.25–7.65(8H,m,C-31-Ph and C-2-Bz(m,p)), 8.12(2H, dd,J=1,9 Hz,C-2-Bz(o)).

Example 81

13-O-[2-Hydroxy-3-phenyl-3-(N,N,N'-trimethylethylenediaminocarbonylamino)propionyl] baccatin III (Compound 82)

The compound (8 mg, 0.008 mmol) of Example 80 was dissolved in ethanol (0.8 ml), followed by the addition of 0.1 N hydrochloric acid (0.8 ml) at 0° C. under stirring. The resulting mixture was stirred for 4 days. Post-treatment and purification were conducted as in Example 53, whereby the title compound (1 mg, 16%) was obtained as a slightly yellow solid.

¹H-NMR (CDCl₃)δ: 1.21(3H,s,C-16 or C-17), 1.23(3H, s,C-16 or C-17), 1.70(3H,s,C-19), 1.80–1.90(1H,m,C-6a), 1.97(3H,d,J=1 Hz,C-18), 2.04–2.15(2H,m,C-14), 2.22(3H, s,C-10:OCOCH₃), 2.40(3H,s,C-4:OCOCH₃), 2.47–2.54 (1H,m,C-6b), 3.01(3H,s,CONCH₃), 3.39(6H,s,N(CH₃)₂), 3.69(2H,br-s), 3.88(1H,d,J=7 Hz,C-3), 4.05(1H,dd,J=2,6 Hz), 4.23(2H,s,C-20), 4.26(1H,dd,J=2,6 Hz), 4.37(1H,dd,J=7,11 Hz,C-7), 4.66(1H,d,J=5 Hz,C-2'), 5.04(1H,dd,J=2,10Hz,C-5), 5.34–5.42(2H,m,C-3' and CONH), 5.70(1H,d, J=7 Hz,C-2), 6.21(1H,br-t,J=9 Hz,C-13), 6.51(1H,s,C-10, 7.27–7.80(8H,m,C-31-Ph and C-2-Bz(m,p)), 8.15(2H,dd,J= 1,9 Hz,C-2-Bz(o)). SI-MS m/z: 878 [M+H]⁺

Compounds 53–82 obtained above in Examples 52–81 are shown in the following Tables 8–12.

TABLE 8

| Comp'd No. | B—A— | Y | Z |
|---|---|---|---|
| 53 | H₃C\N-piperidinyl-N— / H₃C | Ac | TES |

TABLE 8-continued
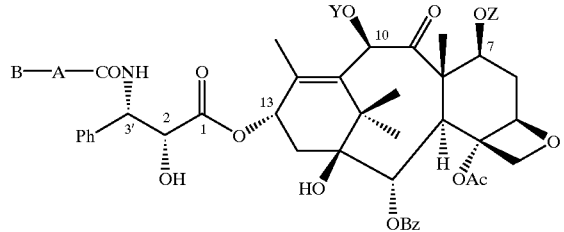
| Comp'd No. | B—A— | Y | Z |
|---|---|---|---|
| 55 | 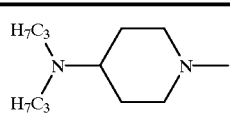 | Ac | TES |
| 57 | 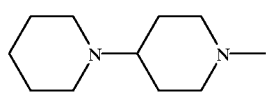 | Ac | TES |
| 59 | 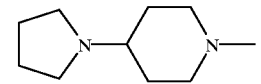 | Ac | TES |
| 61 | 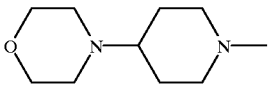 | Ac | TES |
| 63 | 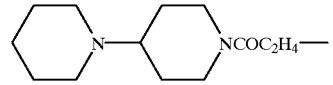 | Ac | TES |
| 67 | 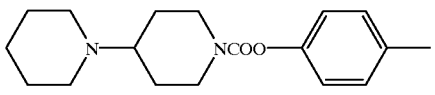 | Troc | Troc |
| 69 | 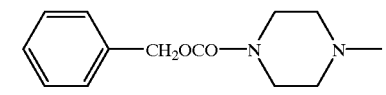 | Ac | TES |
TABLE 9
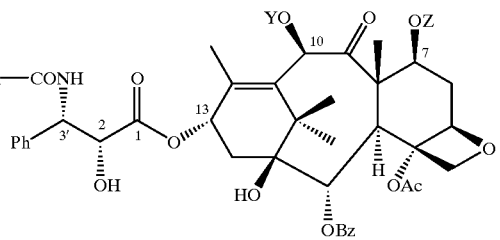
| Comp'd No. | B—A— | Y | Z |
|---|---|---|---|
| 71 | 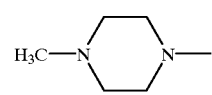 | Ac | TES |
TABLE 9-continued
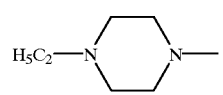
| Comp'd No. | B—A— | Y | Z |
|---|---|---|---|
| 73 | (H5C2—N piperazine N—) | Ac | TES |

TABLE 10

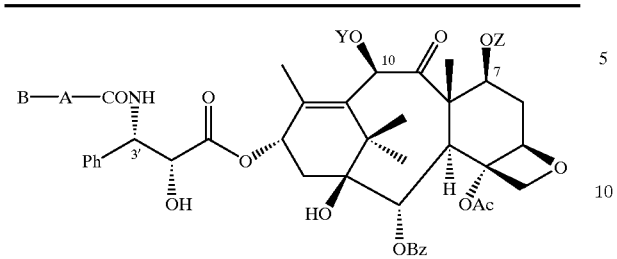

| Comp'd No. | B—A— | Y | Z |
|---|---|---|---|
| 54 | (CH$_3$)$_2$N-piperidine-N-CH$_3$ (4-dimethylamino-1-methylpiperidinyl) | Ac | H |
| 56 | (C$_3$H$_7$)$_2$N-piperidine-N-CH$_3$ (4-dipropylamino-1-methylpiperidinyl) | Ac | H |
| 58 | piperidinyl-piperidine-N-CH$_3$ | Ac | H |
| 60 | pyrrolidinyl-piperidine-N-CH$_3$ | Ac | H |

TABLE 10-continued

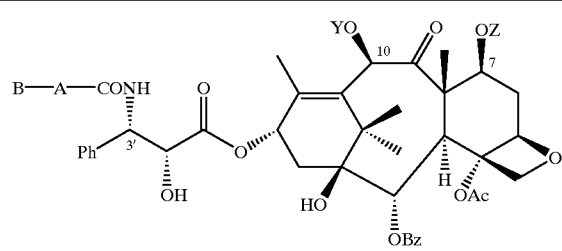

| Comp'd No. | B—A— | Y | Z |
|---|---|---|---|
| 62 | morpholinyl-piperidine-N-CH$_3$ | Ac | H |
| 64 | piperidinyl-piperidine-N-COC$_2$H$_4$— | Ac | H |
| 65 | piperidinyl-piperidine-N-COC$_3$H$_6$— | H | H |
| 66 | piperidinyl-piperidine-N-COOCH$_2$— | H | H |

TABLE 11

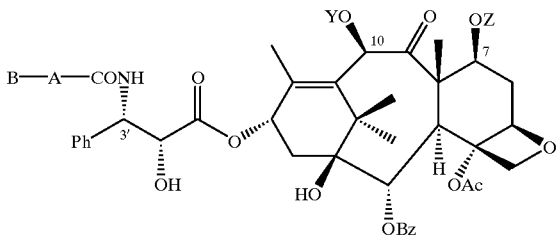

| Comp'd No. | B—A— | Y | Z |
|---|---|---|---|
| 68 | piperidinyl-piperidine-N-COO-C$_6$H$_4$-CH$_3$ | H | H |
| 79 | HN-piperazine-N-CH$_3$ | Ac | H |
| 72 | H$_3$C-N-piperazine-N-CH$_3$ | Ac | H |

TABLE 11-continued
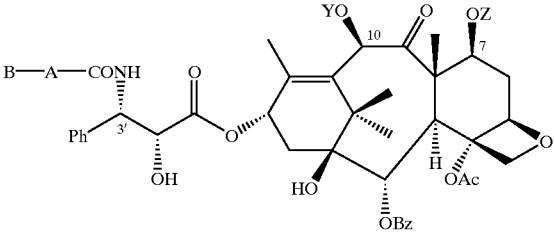
| Comp'd No. | B—A— | Y | Z |
|---|---|---|---|
| 74 | H₅C₂—N⌒N—CH₂— (ethyl-piperazine-methyl) | Ac | H |
| 76 | (H₃C)₂CHNHCOCH₂—N⌒N—CH₃ | H | H |
| 78 | (H₃C)₂CHNHCOCH₂—N⌒N—NCOC₂H₄— | Ac | H |
| 80 | (H₃C)₂CHNHCOCH₂—N⌒N—NCOOCH₂— | Ac | H |
| 82 | (H₃C)(H₃C)NCH₂CH₂N(CH₃)(CH₃) | Ac | H |
TABLE 12
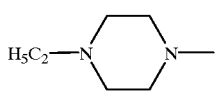
| Comp'd No. | B—A— | Y | Z |
|---|---|---|---|
| 75 | (H₃C)₂CHNHCOCH₂—N⌒N—CH₃ | Troc | Troc |
| 77 | (H₃C)₂CHNHCOCH₂—N⌒N—NCOC₂H₄— | Ac | TES |
| 79 | (H₃C)₂CHNHCOCH₂—N⌒N—NCOOCH₂— | Ac | TES |
| 81 | (H₃C)(H₃C)NCH₂CH₂N(CH₃)(CH₃) | Ac | TES |

Solubilities of Taxane Derivatives (1) in Water

I) Preparation of calibration curves:

Compounds (3) and (42) were weighed in amounts of 1.16 mg and 0.65 mg, to which acetonitrile was added in amounts of 2.0 ml and 1.30 ml so that the compounds were dissolved to provide standard solutions. Using 20 µl portions of the standard solutions, tests were conducted by HPLC (operation conditions 1). Peak areas of the compounds (3) and (42), which had been obtained from chromatograms of their standard solutions, were measured by automated integration. Areas obtained as averages of three measurements were plotted against the amounts (11.6 µg and 10.0 µg) of the compounds (3) and (42) per 20 µl, whereby calibration curves were prepared.

Calibration curve for the compound (3): $Y=1.2\times10^{-4}X$, calibration curve for the compound (42): $Y=1.19\times10^{-4}X$ [X: peak areas, Y: amounts of the compounds (3) and (42) (µg)]

[HPLC operation conditions 1]

Column: Inertsil ODS-2 (5–250), 40 deg.

Mobile phase: 0.01 M $KH_2PO_4$—$CH_3CN$ (5:4).

Flow rate: 1.0 ml/min.

Detection: Ultraviolet absorption photometer (225 nm), 0.08AUFS.

II) Solubility tests of the compounds (3) and (42):

The compounds (3) and (42) were weighed in amounts of 3.10 mg and 2.70 mg and then suspended in 2.0 ml portions of purified water, respectively. To the respective suspensions, 0.1 N hydrochloric acid was added in amounts of 35 λl and 30 µl (1.1 eq.). By ultrasonication the resulting mixtures were formed into uniform suspensions, which were then shaken at room temperature for 2 hours. The thus-obtained mixtures were filtered through membrane filters (0.22 pm), and the filtrates were provided as test solutions. Using 5 µl portions of the test solutions, tests were conducted by HPLC (operation conditions 1). From areas obtained as averages of three measurements, the solubilities of the compounds (3) and (42) were determined.

Area (X) of the compound (3) obtained as an average of three measurements: 52570

Dissolved amount (Y) of the compound (3): 6.31 µg/5 µl (1.26 mg/ml)

Area (X) of the compound (42) obtained as an average of three measurements: 49558

Dissolved amount (Y) of the compound (42): 5.90 µg/5 µl (1.18 mg/ml)

Measurement of Solubility of Taxol in Water

I) Preparation of calibration curve:

Taxol was weighed in an amount of 1.20 mg, to which acetonitrile was added so that Taxol was dissolved to give 20.0 ml precisely, whereby a standard solution was provided. By conducting operations in a similar manner as in the case of the compound (3), a calibration curve was prepared. Calibration curve: $Y=5.20\times10^{-5}X$ [X: peak area, Y: Amount of Taxol (µg))

II) Solubility test of Taxol:

Taxol was weight in an amount of 3.15 mg and then suspended in 30.0 ml of purified water. By ultra-sonication the suspension was formed into a uniform suspension, which was then shaken at room temperature for 2 hours. By conducting operations in a similar manner as in the case of the compound (3), its solubility was determined (injected amount: 100 µl).

Area (X) obtained as an average of three measurements: 677

Dissolved amount (Y) of Taxol: 0.04 µg/100 µl (0.4 µg/ml)

TABLE 13

| Compound | Solubility (µg/ml) |
| --- | --- |
| Taxol | 0.4 |
| Compound 3 | 1260 |
| Compound 42 | 1180 |

Test 2

Solubility of Taxane Derivative (1) in Water

I) Preparation of calibration curves:

Compound (58) was weighed in an amount of 2.50 mg, to which acetonitrile was added in an amount of 2.5 ml so that the compound was dissolved to provide a standard solution. Using 20 At of the standard solution, a test was conducted by HPLC (operation conditions 1). A peak area of the compound (58) obtained from a chromatogram of the standard solution was measured by automated integration. The area obtained as an average of three measurements was plotted against the amounts (20 µg) of the compound (58) per 20 µl, whereby calibration curve was prepared.

Calibration curve: $Y=1.10\times10^{-4}X$ (X: peak area, Y: amount of compound (58) (µg)].

Operation conditions for the HPLC operation were set as in Test 1.

II) Solubility test of the compound (58):

The compound (58) was weighed in an amount of 4.20 mg and then suspended in purified water (2.0 ml). To the suspension, 0.1 N hydrochloric acid (47 µl, 1.06 eq.) was added. By ultrasonication the resulting mixture was formed into a uniform suspension, which was then shaken at room temperature for 2 hours. The mixture was filtered through a membrane filter (0.22 pm), and the filtrate was provided as a test solution. Using 5 µl of the test solution, a test was conducted by HPLC (the above operation conditions). From an area obtained as an average of three measurements, the solubility of the compound (58) was determined.

Area (X) obtained as an average of three measurements: 71999

Dissolved amount (Y) of the compound (58): 7.95 µg/5 µl (1.59 mg/ml)

The solubility of Taxol in water was measured in a similar manner as in Test 1.

TABLE 14

| Compound | Solubility (µg/ml) |
| --- | --- |
| Taxol | 0.4 |
| Compound 58 | 1590 |

Test 3

Growth Inhibitory Activities of Taxane Derivatives (1)

Materials and procedures

Cells

As a cell strain KB derived from a human mouth cancer, one purchased from Dainippon Pharmaceutical Co., Ltd. and stored in a lyophilized form at The Central Research Center, Yakult Honsha Co., Ltd. was used. In Dulbeccols modefied Earglets medium containing 10% fetal bovine serum (product of NISSUI PHARMACEUTICAL CO., LTD.), the KB was maintenance-cultured under the following conditions: 5%, $CO_2$-air, 37° C.

Drugs

Each compound was used by dissolving it at a concentration of 10 mg/ml in DMSO.

Drug Treatment (1) KB

On Day-1, cells which were in a logarithmic growth phase were inoculated at 2,000 cells/100 μl/well on 96-well microtiter plates (Falcon #3072) by using a phenol-red-free culture medium with 10% fetal bovine serum contained therein (Dulbecco's molefied Eargle's medium (Sigma)), and were cultured overnight. On Day 0, the compounds each of which had been diluted to 0.03 to 10,000 ng/ml with the same culture medium were added in 100 μl aliquots to the individual wells, and the cells were cultured for 3 days. Three wells were used per each drug concentration. Each plate was provided with three blank wells containing only the culture medium and also with eight wells as a drug-untreated control.

XTT Assay

Before use, XTT (Sigma) was dissolved at a concentration of 1 mg/me in each culture media which as free of serum. Phenodin methosulfate (Sigma) dissolved at a concentration of 5 mM in PBS was added to the resulting solution at a volume ratio of 1/200. To each well, the solution so prepared was added in an amount of 50 μl per well. Subsequent to culture for 4 hours, OD was measured at 450 nm by ELISA.

Calculation of 50% Growth Inhibitory Concentration ($GI_{50}$)

$GI_{50}$ was calculated by interpolation from a concentration-growth inhibition rate (GIR). GIR was determined in accordance with the following formula:

$$GIR = 100 - \frac{OD_{Treated(Day3)} - OD_{Control(Day0)}}{OD_{Control(Day3)} - OD_{Control(Day0)}} \times 100$$

Bibiography

Scudiero D A, et al., Cacer Res., 48, 4827–4833, 1988.

1994 Report of The Anticancer Agent Screening Special Committee, "Cancers and Chemotherapy", 21, 1306–1307.

Test results are shown in the following table.

TABLE 15

Growth Inhibitory Activity of Taxane Derivatives

| Compound | KB | |
| --- | --- | --- |
| No. | $GI_{50}$ (ng/ml) | Activity ratio |
| 6 | 0.73 | 2.7 |
| 9 | 0.78 | 2.6 |
| 39 | 0.59 | 3.4 |
| 42 | 0.65 | 3.1 |
| 45 | 0.86 | 2.3 |
| Taxol | 2.0 | 1.0 |

Capability of Exploitation in Industry

The taxane derivatives according to the present invention have very high solubility in water, namely, water solubility as high as 1,000 times or more of Taxol, so that they can be formulated into liquid preparations such as injections without using any special solvent. In addition, there are also excellent in antitumor activities.

We claim:

1. A taxane derivative represented by the following formula (1):

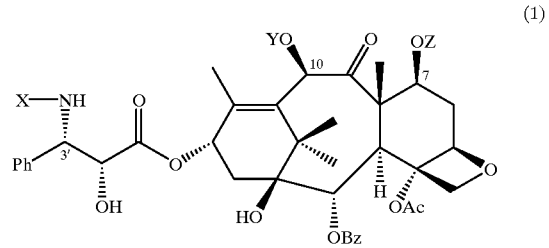

wherein at least one of X and Y represents a group —CO—A—B in which A represents a single bond, a group —R—CO—, a group —R—OCO— or a group —R—NHCO—, R representing a lower alkylene group or a phenylene group, B represents a group

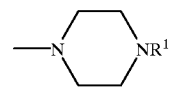

in which $R^1$ represents a hydrogen atom, a substituted or unsubstituted alkyl group or an aralkyloxycarbonyl group, a group

in which $R^2$ represents an amino group, a mono or di-alkylamino group, a piperidino group, a pyrrolidino group or a morpholino group, or a group

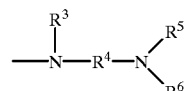

in which $R^3$, $R^5$ and $R^6$ each independently represent a hydrogen atom or a lower alkyl group and $R^4$ represents a lower alkylene group, and the other represents a hydrogen atom, a lower alkanoyl group, a benzoyl group, an alkoxycarbonyl group or a trihalogenoalkoxycarbonyl group; Z represents a hydrogen atom, a trialkylsilyl group or a trihalogenoalkoxycarbonyl group; Ac represents an acetyl group, Bz represents a benzoyl group, and Ph represents a phenyl group; or a salt thereof.

2. A taxane derivative represented by the following formula (2):

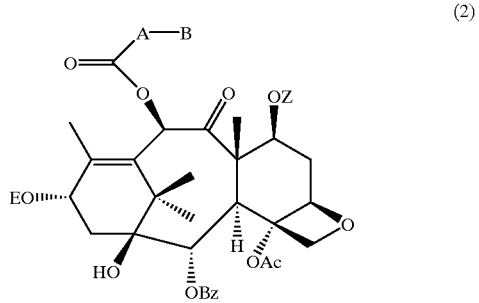

wherein A represents a single bond, a group —R—CO—, a group —R—OCO— or a group —R—NHCO—, R representing a lower alkylene group or a phenylene group, B represents a group

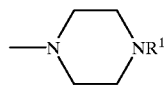

in which $R^1$ represents a hydrogen atom, a substituted or unsubstituted alkyl group or an aralkyloxycarbonyl group, a group

in which $R^2$ represents an amino group, a mono or di-alkylamino group, a piperidino group, a pyrrolidino group or a morpholino group, or a group

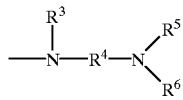

in which $R^3$, $R^5$ and $R^6$ each independently represent a hydrogen atom or a lower alkyl group and $R^4$ represents a lower alkylene group;

Z represents a hydrogen atom, a trialkylsilyl group or a trihalogenoalkoxycarbonyl group;

E represents a hydrogen atom or a group

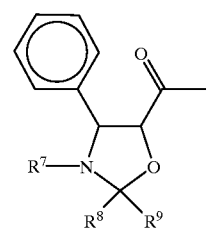

wherein $R^7$ represents a hydrogen atom, an alkoxycarbonyl group or an aralkyloxycarbonyl group, $R^8$ and $R^9$ each independently represent a hydrogen atom, an alkyl group, a halogenoalkyl group or an alkoxyphenyl group with the proviso that $R^8$ and $R^9$ do no represent hydrogen atoms at the same time and, when one of $R^8$ and $R^9$ is a halogenoalkyl group or an alkoxyphenyl group, the other is a hydrogen atom, Ac represents an acetyl group, and Bz represents a benzoyl group; or a salt thereof.

3. A drug composition comprising the taxane derivative or the salt thereof as defined in claim 1 and a pharmacologically acceptable carrier.

4. A method the treatment of a tumor, which comprises administering the taxane derivative or the salt thereof as defined in claim 1.

5. The drug composition according to claim 3, which is an antitumor agent.

* * * * *

UNITED STATES PATENT AND TRADEMARK OFFICE
CERTIFICATE OF CORRECTION

PATENT NO. : 6,025,385

DATED : February 15, 2000

INVENTOR(S): Hideaki SHIMIZU, et al

It is certified that an error appears in the above-identified patent and that said Letters Patent is hereby corrected as shown below:

Column 72, line 18, "do no represent" should read --do not represent--

Signed and Sealed this

Twenty-fourth Day of April, 2001

Attest:

NICHOLAS P. GODICI

Attesting Officer

Acting Director of the United States Patent and Trademark Office